US012696901B2

(12) United States Patent
Sikervar et al.

(10) Patent No.: US 12,696,901 B2
(45) Date of Patent: Aug. 4, 2026

(54) PESTICIDALLY ACTIVE HETEROCYCLIC DERIVATIVES WITH SULFUR CONTAINING SUBSTITUENTS

(71) Applicant: SYNGENTA CROP PROTECTION AG, Basel (CH)

(72) Inventors: Vikas Sikervar, Bracknell (GB); Indira Sen, Goa (IN); Michel Muehlebach, Stein (CH); Sebastian Rendler, Basel (CH); André Stoller, Stein (CH); Daniel Emery, Stein (CH); Benedikt Kurtz, Stein (CH); Anke Buchholz, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 991 days.

(21) Appl. No.: 17/791,083

(22) PCT Filed: Jan. 6, 2021

(86) PCT No.: PCT/EP2021/050132

§ 371 (c)(1),
(2) Date: Jul. 6, 2022

(87) PCT Pub. No.: WO2021/140122

PCT Pub. Date: Jul. 15, 2021

(65) Prior Publication Data

US 2023/0088968 A1 Mar. 23, 2023

(30) Foreign Application Priority Data

Jan. 6, 2020 (IN) ............................ 202011000541

(51) Int. Cl.

| | |
|---|---|
| ***A01N 43/90*** | (2006.01) |
| ***A01P 5/00*** | (2006.01) |
| ***A01P 7/02*** | (2006.01) |
| ***A01P 7/04*** | (2006.01) |
| ***A01P 9/00*** | (2006.01) |
| ***C07D 471/04*** | (2006.01) |
| ***C07D 519/00*** | (2006.01) |

(52) U.S. Cl.

CPC ................ *A01N 43/90* (2013.01); *A01P 5/00* (2021.08); *A01P 7/02* (2021.08); *A01P 7/04* (2021.08); *A01P 9/00* (2021.08); *C07D 471/04* (2013.01); *C07D 519/00* (2013.01)

(58) Field of Classification Search

CPC ..................................................... A01N 43/90
USPC ......................................................... 514/300
See application file for complete search history.

(56) References Cited

U.S. PATENT DOCUMENTS

| | | | |
|---|---|---|---|
| 10,464,950 B2 | 11/2019 | Kudo et al. | |
| 2023/0303565 A1* | 9/2023 | Sikervar | ................ A01N 43/90 |

FOREIGN PATENT DOCUMENTS

| | | | |
|---|---|---|---|
| CN | 107207506 | A | 9/2017 |
| EP | 3257853 | A1 | 12/2017 |
| EP | 3539958 | A1 | 9/2019 |
| EP | 3564241 | A1 | 11/2019 |
| JP | 2020189891 | A | 11/2020 |
| WO | 2018052136 | A1 | 3/2018 |

OTHER PUBLICATIONS

Written Opinion of the International Searching Authority and International Search Report for International Application No. PCT/EP2021/050132 mailed Mar. 15, 2021.

* cited by examiner

*Primary Examiner* — Niloofar Rahmani
(74) *Attorney, Agent, or Firm* — BakerHostetler; Toni-Junell Herbert

(57) ABSTRACT

Compounds of the formula (I) wherein the substituents are as defined in claim 1. Furthermore, the present invention relates to agrochemical compositions which comprise compounds of formula (I), to preparation of these compositions, and to the use of the compounds or compositions in agriculture or horticulture for combating, preventing or controlling animal pests, including arthropods and in particular insects, nematodes, molluscs or representatives of the order Acarina.

(I)

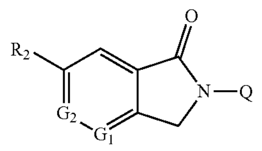

21 Claims, No Drawings

PESTICIDALLY ACTIVE HETEROCYCLIC DERIVATIVES WITH SULFUR CONTAINING SUBSTITUENTS

CROSS-REFERENCE TO RELATED APPLICATIONS

This application is a 371 National Stage application of International Application No. PCT/EP2021/050132 filed Jan. 6, 2021, which claims the benefit of IN 202011000541, filed Jan. 6, 2020, the entire contents of these applications are hereby incorporated by reference.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order Acarina.

Heterocyclic benzannulated dihydropyrrolone and phtalimide derivatives with sulfur-containing substituents have been described in the literature, for example in J. Org. Chem. 2003, 62, 8240 and Bull. Chem Soc. Chim. Belg. 1997, 106, 151. However, no compounds mentioned in these references have been described to exert a pesticidal effect. Pesticidally active heterocyclic derivatives with sulfur-containing substituents have been described, for example in WO 2012/012086848, WO 2013/018928 and WO 2020/171077.

It has now surprisingly been found that certain novel pesticidally active derivatives with sulfur containing substitutents have favourable properties as pesticides.

The present invention therefore provides compounds of formula I, (I)

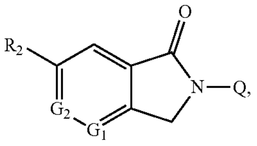

wherein $G_1$ and $G_2$ are, independently from each other, CH or N;

$R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

Q is a radical selected from the group consisting of formula Qa and Qb

Qa

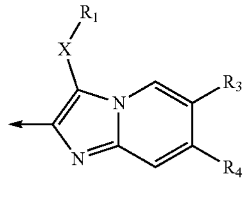

Qb

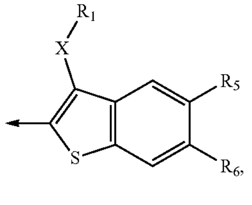

wherein the arrow denotes the point of attachment to the nitrogen atom of the bicyclic ring; and wherein, X is S, SO, or $SO_2$;

$R_1$ is $C_1$-$C_4$ alkyl or $C_3$-$C_6$ cycloalkyl-$C_1$-$C_4$ alkyl;

$R_3$, $R_4$, $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, $C_3$-$C_6$ cyanocycloalkyl$C_1$-$C_4$ alkoxy, cyano, $C_1$-$C_4$ alkoxy, $C_1$-$C_6$ haloalkoxy, —$N(R_7)_2$, or —$N(R_7)C(=O)R_8$; and $R_7$ and $R_8$ are, independently from each other, hydrogen, $C_1$-$C_4$ alkyl, $C_1$-$C_6$ haloalkyl, or $C_3$-$C_6$ cycloalkyl.

The present invention also provides agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$ alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$ alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

Where substituents are indicated as being itself further substituted, this means that they carry one or more identical or different substituents, e.g. one to four substituents. Normally not more than three such optional substituents are present at the same time. Preferably not more than two such substituents are present at the same time (i.e. the group is substituted by one or two of the substituents indicated). Where the additional substituent group is a larger group, such as cycloalkyl or phenyl, it is most preferred that only one such optional substituent is present. Where a group is indicated as being substituted, e.g. alkyl, this includes those groups that are part of other groups, e.g. the alkyl in alkylthio.

The term "$C_1$-$C_n$ alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethyl-propyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$ haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2, 3,3, 3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$-fluoroalkyl" would refer to a $C_1$-$C_2$-alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or penta-fluoroethyl.

The term "$C_1$-$C_n$ alkoxy" as used herein refers to a straight-chain or branched saturated alkyl radical having 1 to n carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1,1-dimethylethoxy.

The term "$C_1$-$C_n$ haloalkoxy" as used herein refers to a $C_1$-$C_n$ alkoxy radical as mentioned above which is partially or fully substituted by fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroeth-oxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2, 3,3, 3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, or 4-bromobutoxy.

The term "$C_1$-$C_n$ haloalkylsulfanyl" as used herein refers to a $C_1$-$C_n$ alkylthio radical as mentioned above which is partially or fully substituted by fluorine, chlorine, bromine and/or iodine, i.e., for example, any one of fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, or 4-bromobutylthio.

The term "$C_1$-$C_n$ haloalkylsulfinyl" and "$C_1$-$C_n$ haloalkylsulfonyl" refers to the groups above but with the sulfur in oxidations state 1 or 2 respectively.

The term "$C_1$-$C_n$ cyanoalkyl" as used herein refers to a straight chain or branched saturated alkyl radicals having 1 to n carbon atoms (as mentioned above) which is substituted by a cyano group, for example cyanomethylene, cyanoethylene, 1,1-dimethylcyanomethyl, cyanomethyl, cyanoethyl, cyanisopropyl and 1-dimethylcyanomethyl.

The term "$C_1$-$C_n$ cyanoalkoxy" refers to the groups above but which is attached via an oxygen atom.

The suffix "—$C_1$-$C_n$ alkyl" after terms such as "$C_3$-$C_n$ cycloalkyl", wherein n is an integer from 1-6, as used herein refers to a straight chain or branched saturated alkyl radicals which is substituted by $C_3$-$C_n$ cycloalkyl. An example of $C_3$-$C_n$ cycloalkyl-$C_1$-$C_n$ alkyl is for example, cyclopropylmethyl.

The term "$C_3$-$C_6$ cycloalkyl" as used herein refers to 3-6 membered cycloalkyl groups such as cyclopropane, cyclobutane, cyclopropane, cyclopentane and cyclohexane.

Halogen is generally fluorine, chlorine, bromine or iodine. This also applies, correspondingly, to halogen in combination with other meanings, such as haloalkyl.

Certain embodiments according to the invention are provided as set out below.

Embodiment 1 provides compounds of formula I, or an agrochemically acceptable salt, stereoisomer, enantiomer, tautomer or N-oxide thereof, as defined above.

Embodiment 2 provides compounds, or an agrochemically acceptable salt, stereoisomer, enantiomer, tautomer or N-oxide thereof, according to embodiment 1 wherein Q is Qa and having preferred values of $R_2$, $G_1$, $G_2$, X, $R_1$, $R_3$, $R_4$, $R_7$ and $R_8$ as set out below.

Embodiment 3 provides compounds, or an agrochemically acceptable salt, stereoisomer, enantiomer, tautomer or N-oxide thereof, according to embodiment 1 wherein Q is Qb and having preferred values of $R_2$, $G_1$, $G_2$, X, $R_1$, $R_5$, $R_6$, $R_7$ and $R_8$ as set out below.

With respect to embodiments 1-3, preferred values of $R_2$, $G_1$, $G_2$, X, $R_1$, $R_3$, $R_4$, $R_5$, $R_6$, $R_7$ and $R_8$ are, in any combination thereof, as set out below:

Preferably $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy.

More preferably $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy.

Even more preferably $R_2$ is $—CF_3$, $—CF_2CF_3$, $—SCF_3$, $—SOCF_3$, $—SO_2CF_3$, $—OCHF_2$, $—OCF_3$ or $—OSO_2CF_3$.

Most preferably $R_2$ is $—CF_3$, $—OCHF_2$, $—OCF_3$ or $—SO_2CF_3$.

Preferably either $G_1$ is N and $G_2$ is CH, or $G_1$ is CH and $G_2$ is N.

Also preferred is when both $G_1$ and $G_2$ are N.

Also preferred is when both $G_1$ and $G_2$ are CH.

Most preferably $G_1$ is N and $G_2$ is CH.

Preferably X is S or $SO_2$.

Most preferably X is $SO_2$.

Preferably $R_1$ is $C_1$-$C_4$ alkyl or cyclopropyl-$C_1$-$C_4$ alkyl.

More preferably $R_1$ is ethyl or cyclopropylmethyl.

Most preferably $R_1$ is ethyl.

Preferably $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$.

More preferably $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

Even more preferably $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy or —$NHC(O)CH_3$.

Most preferably $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$.

Utmost preferably $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy or —$NHC(O)CH_3$; or $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy or —$NHC(O)CH_3$.

Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —$NHC(O)CH_3$.

Preferably $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$.

More preferably $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

Even more preferably $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy or —$NHC(O)CH_3$.

Most preferably $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$. Utmost preferably $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy or —$NHC(O)CH_3$; or $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy or —$NHC(O)CH_3$.

Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —$NHC(O)CH_3$.

Preferably $R_7$ and $R_8$ are, independently from each other, hydrogen or $C_1$-$C_4$ alkyl.

More preferably $R_7$ and $R_8$ are, independently from each other, hydrogen or methyl.

Most preferably $R_7$ is hydrogen or methyl, and $R_8$ is methyl.

Utmost preferably $R_7$ is hydrogen, and $R_8$ is methyl.

Further embodiments according to the invention are provided as set forth below.

A preferred group of compounds of formula I is represented by the compounds of formula I-1

(I-1)

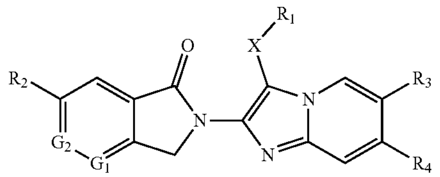

wherein $R_2$, $G_1$, $G_2$, X, $R_1$, $R_3$, $R_4$, $R_7$ and $R_8$ are as defined under formula I above.

In one preferred group of compounds of formula I-1, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-1, $R_1$ is ethyl or cyclopropylmethyl; X is S or $SO_2$; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C(O)CH_3$.

In a further preferred group of compounds of formula I-1, $R_1$ is ethyl; X is $SO_2$; $R_2$ is —$CF_3$, —$CF_2CF_3$, —$SCF_3$, —$SOCF_3$, —$SO_2CF_3$, —$OCHF_2$, —$OCF_3$ or —$OSO_2CF_3$; and $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C(O)CH_3$. Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

In a further preferred group of compounds of formula I-1, $R_1$ is ethyl; X is $SO_2$; $R_2$ is —$CF_3$, —$SO_2CF_3$, —$OCHF_2$, or —$OCF_3$; and $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —NHC(O)$CH_3$.

One preferred group of compounds according to this embodiment are compounds of formula (I-1a) which are compounds of formula (I-1), or of any of the preferred embodiments of the compounds of formula (I-1), wherein $R_2$ is —$CF_3$, —$OCHF_2$, —$OCF_3$ or —$SO_2CF_3$, preferably $R_2$ is —$CF_3$; X is S or $SO_2$; preferably X is $SO_2$; and $R_1$ is ethyl or cyclopropylmethyl; preferably $R_1$ is ethyl.

Another preferred group of compounds according to this embodiment are compounds of formula (I-1 b) which are compounds of formula (I-1), or of any of the preferred embodiments of the compounds of formula (I-1), wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C(O)CH_3$.

Another preferred group of compounds according to this embodiment are compounds of formula (I-1b-1) which are compounds of formula (I-1), or of any of the preferred embodiments of the compounds of formula (I-1), wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

A further preferred group of compounds according to this embodiment are compounds of formula (I-1c) which are compounds of formula (I-1), or of any of the preferred embodiments of the compounds of formula (I-1), wherein $G_1$ is N and $G_2$ is CH.

One preferred group of compounds according to this embodiment are compounds of formula (I-1d) which are compounds of formula (I-1), or of any of the preferred embodiments of the compounds of formula (I-1), wherein $G_1$ is CH and $G_2$ is N.

Another preferred group of compounds according to this embodiment are compounds of formula (I-1e) which are compounds of formula (I-1), or of any of the preferred embodiments of the compounds of formula (I-1), wherein both $G_1$ and $G_2$ are N.

Another preferred group of compounds according to this embodiment are compounds of formula (I-1f) which are compounds of formula (I-1), or of any of the preferred embodiments of the compounds of formula (I-1), wherein both $G_1$ and $G_2$ are CH.

The present invention also provides agrochemically acceptable salts, stereoisomers, enantiomers, tautomers and N-oxides of the compounds of formula I-1.

Another preferred group of compounds of formula I is represented by the compounds of formula I-2

(I-2)

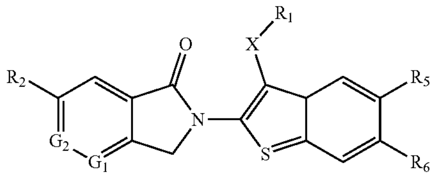

wherein $R_2$, $G_1$, $G_2$, X, $R_1$, $R_5$, $R_6$, $R_7$ and $R_8$ are as defined under formula I above.

In one preferred group of compounds of formula I-2, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-2, $R_1$ is ethyl or cyclopropylmethyl; X is S or $SO_2$; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C(O)CH_3$.

In a further preferred group of compounds of formula I-2, $R_1$ is ethyl; X is $SO_2$; $R_2$ is —$CF_3$, —$CF_2CF_3$, —$SCF_3$, —$SOCF_3$, —$SO_2CF_3$, —$OCHF_2$, —$OCF_3$ or —$OSO_2CF_3$; and $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C(O)CH_3$.

In a further preferred group of compounds of formula I-2, $R_1$ is ethyl; X is $SO_2$; $R_2$ is —$CF_3$, —$SO_2CF_3$, —$OCHF_2$, or —$OCF_3$; and $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —NHC(O)$CH_3$. Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

One preferred group of compounds according to this embodiment are compounds of formula (I-2a) which are compounds of formula (I-2), or of any of the preferred embodiments of the compounds of formula (I-2), wherein $R_2$ is —$CF_3$, —$OCHF_2$, —$OCF_3$ or —$SO_2CF_3$, preferably $R_2$ is —$CF_3$; X is S or $SO_2$; preferably X is $SO_2$; and $R_1$ is ethyl or cyclopropylmethyl; preferably $R_1$ is ethyl.

Another preferred group of compounds according to this embodiment are compounds of formula (I-2b) which are compounds of formula (I-2), or of any of the preferred embodiments of the compounds of formula (I-2), wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$.

Another preferred group of compounds according to this embodiment are compounds of formula (I-2b-1) which are compounds of formula (I-2), or of any of the preferred embodiments of the compounds of formula (I-2), wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

A further preferred group of compounds according to this embodiment are compounds of formula (I-2c) which are compounds of formula (I-2), or of any of the preferred embodiments of the compounds of formula (I-2), wherein $G_1$ is N and $G_2$ is CH.

One preferred group of compounds according to this embodiment are compounds of formula (I-2d) which are compounds of formula (I-2), or of any of the preferred embodiments of the compounds of formula (I-2), wherein $G_1$ is CH and $G_2$ is N.

Another preferred group of compounds according to this embodiment are compounds of formula (I-2e) which are compounds of formula (I-2), or of any of the preferred embodiments of the compounds of formula (I-2), wherein both $G_1$ and $G_2$ are N.

Another preferred group of compounds according to this embodiment are compounds of formula (I-20 which are compounds of formula (I-2), or of any of the preferred embodiments of the compounds of formula (I-2), wherein both $G_1$ and $G_2$ are CH.

The present invention also provides agrochemically acceptable salts, stereoisomers, enantiomers, tautomers and N-oxides of the compounds of formula I-2.

Another preferred group of compounds of formula I is represented by the compounds of formula I-3

(I-3)

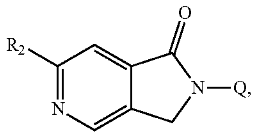

wherein Q is a radical selected from the group consisting of formula Qa and Qb

Qa

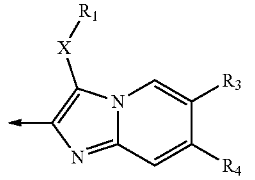

Qb

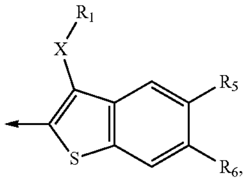

wherein the arrow denotes the point of attachment to the nitrogen atom of the bicyclic ring; and $R_2$, X, $R_1$, $R_3$, $R_4$, $R_5$, $R_6$, $R_7$ and $R_8$ are as defined under formula I above.

In one preferred group of compounds of formula I-3, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; and X is S or $SO_2$.

In another preferred group of compounds of formula I-3, $R_1$ is ethyl or cyclopropylmethyl; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and X is S or $SO_2$.

In a further preferred group of compounds of formula I-3, $R_1$ is ethyl; X is $SO_2$; and $R_2$ is —$CF_3$, —$CF_2CF_3$, —$SCF_3$, —$SOCF_3$, —$SO_2CF_3$, —$OCHF_2$, —$OCF_3$ or —$OSO_2CF_3$.

In a further preferred group of compounds of formula I-3, $R_1$ is ethyl; X is $SO_2$; and $R_2$ is —$CF_3$, —$SO_2CF_3$, —$OCHF_2$, or —$OCF_3$.

One preferred group of compounds according to this embodiment are compounds of formula (I-3a) which are compounds of formula (I-3), or of any of the preferred embodiments of the compounds of formula (I-3), wherein Q is Qa.

In one preferred group of compounds of formula I-3a, $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-3a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

In another preferred group of compounds of formula I-3a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —$NHC(O)CH_3$. Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —$NHC(O)CH_3$.

A further preferred group of compounds of formula I-3a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$.

A further preferred group of compounds of formula I-3a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$.

Another preferred group of compounds according to this embodiment are compounds of formula (I-3b) which are compounds of formula (I-3), or of any of the preferred embodiments of the compounds of formula (I-3), wherein Q is Qb.

In one preferred group of compounds of formula I-3b, $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-3b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

In another preferred group of compounds of formula I-3b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —$NHC(O)CH_3$. Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —$NHC(O)CH_3$.

A further preferred group of compounds of formula I-3b are those compounds wherein RB is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$.

A further preferred group of compounds of formula I-3b are those compounds wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$.

An outstanding group of compounds of formula I-3b are the compounds of formula (I-3b-2) wherein:

$R_2$ is —$CF_3$, —$OCHF_2$, —$OCF_3$ or —$SO_2CF_3$; preferably $R_2$ is —$CF_3$;

X is S or $SO_2$; preferably X is $SO_2$;

$R_1$ is ethyl or cyclopropylmethyl; preferably $R_1$ is ethyl; and $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$.

Another outstanding group of compounds of formula I-3b-2 are those wherein:

$R_5$ is hydrogen; and $R_6$ is methyl, trifluoromethyl, cyclopropyl, 1-cyanocyclopropyl, 1-cyano-1-methyl-ethyl, cyano, methoxy, isopropoxy, 2,2,2-trifluoroethoxy, —$NHC(O)CH_3$ or —$NCH_3C(O)CH_3$; preferably $R_6$ is trifluoromethyl.

Another outstanding group of compounds of formula I-3b-2 are those wherein:

$R_5$ is hydrogen; and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; preferably $R_6$ is trifluoromethyl.

The present invention also provides agrochemically acceptable salts, stereoisomers, enantiomers, tautomers and N-oxides of the compounds of formula I-3.

Another preferred group of compounds of formula I is represented by the compounds of formula I-4

(I-4)

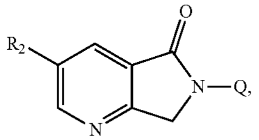

wherein Q is a radical selected from the group consisting of formula Qa and Qb

Qa

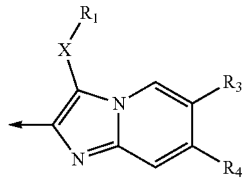

Qb

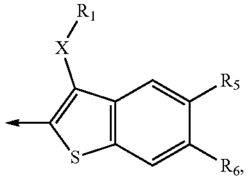

wherein the arrow denotes the point of attachment to the nitrogen atom of the bicyclic ring; and $R_2$, X, $R_1$, $R_3$, $R_4$, $R_5$, $R_6$, $R_7$ and $R_8$ are as defined under formula I above.

In one preferred group of compounds of formula I-4, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; and X is S or $SO_2$.

In another preferred group of compounds of formula I-4, $R_1$ is ethyl or cyclopropylmethyl; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and X is S or $SO_2$.

In a further preferred group of compounds of formula I-4, $R_1$ is ethyl; X is $SO_2$; and $R_2$ is $-CF_3$, $-CF_2CF_3$, $-SCF_3$, $-SOCF_3$, $-SO_2CF_3$, $-OCHF_2$, $-OCF_3$ or $-OSO_2CF_3$.

In a further preferred group of compounds of formula I-4, $R_1$ is ethyl; X is $SO_2$; and $R_2$ is $-CF_3$, $-SO_2CF_3$, $-OCHF_2$, or $-OCF_3$.

One preferred group of compounds according to this embodiment are compounds of formula (I-4a) which are compounds of formula (I-4), or of any of the preferred embodiments of the compounds of formula (I-4), wherein Q is Qa.

In one preferred group of compounds of formula I-4a, $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or $-N(R_7)C(=O)R_8$;

and $R_7$ and $R_8$ are, independently from each other, hydrogen or $C_1$-$C_4$ alkyl.

In another preferred group of compounds of formula I-4a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, $-NHC(O)CH_3$ or $-NCH_3C(O)CH_3$.

In another preferred group of compounds of formula I-4a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or $-NHC(O)CH_3$. Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and $-NHC(O)CH_3$.

A further preferred group of compounds of formula I-4a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, $-NHC(O)CH_3$ or $-NCH_3C(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, $-NHC(O)CH_3$ or $-NCH_3C(O)CH_3$.

A further preferred group of compounds of formula I-4a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or $-NHC(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or $-NHC(O)CH_3$.

An outstanding group of compounds of formula I-4a are the compounds of formula (I-4a-2) wherein:

$R_2$ is $-CF_3$ or $-SO_2CF_3$; preferably $R_2$ is $-CF_3$;

X is S or $SO_2$; preferably X is $SO_2$;

$R_1$ is ethyl or cyclopropylmethyl; preferably $R_1$ is ethyl; and $R_4$ is hydrogen and $R_3$ is hydrogen, methyl, trifluoromethyl, cyclopropyl, 1-cyanocyclopropyl, 1-cyano-1-methyl-ethyl, cyano, methoxy, isopropoxy, 2,2,2-trifluoroethoxy, $-NHC(O)CH_3$ or $-NCH_3C(O)CH_3$; preferably $R_3$ is trifluoromethyl; or $R_3$ is hydrogen and $R_4$ is methyl, trifluoromethyl, cyclopropyl, 1-cyanocyclopropyl, 1-cyano-1-methyl-ethyl, cyano, methoxy, isopropoxy, 2,2,2-trifluoroethoxy, $-NHC(O)CH_3$ or $-NCH_3C(O)CH_3$; preferably $R_4$ is trifluoromethyl or 1-cyanocyclopropyl.

An outstanding group of compounds of formula I-4a-2 are those wherein:

$R_3$ is hydrogen; and $R_4$ is trifluoromethyl or 1-cyanocyclopropyl.

Another outstanding group of compounds of formula I-4a-2 are those wherein:

$R_4$ is hydrogen and $R_3$ is trifluoromethyl.

Another outstanding group of compounds of formula I-4a are the compounds of formula (I-4a-3) wherein:

$R_2$ is —$CF_3$, —$OCHF_2$, —$OCF_3$ or —$SO_2CF_3$; preferably $R_2$ is —$CF_3$;

X is S or $SO_2$; preferably X is $SO_2$;

$R_1$ is ethyl; and $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; preferably $R_3$ is bromo, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; preferably $R_4$ is bromo, methyl, trifluoromethyl, 1,1-difluoroethyl, cyclopropyl, 1-cyanocyclopropyl, methoxy, or 2,2,2-trifluoroethoxy.

An outstanding group of compounds of formula I-4a-3 are those wherein:

$R_2$ is —$CF_3$;

X is $SO_2$;

$R_3$ is hydrogen; and $R_4$ is bromo, methyl, trifluoromethyl, 1,1-difluoroethyl, cyclopropyl, 1-cyanocyclopropyl, methoxy or 2,2,2-trifluoroethoxy.

Another outstanding group of compounds of formula I-4a-3 are those wherein:

$R_2$ is —$CF_3$;

X is $SO_2$;

$R_4$ is hydrogen; and $R_3$ is bromo, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy or —NHC(O)$CH_3$.

Another preferred group of compounds according to this embodiment are compounds of formula (I-4b) which are compounds of formula (I-4), or of any of the preferred embodiments of the compounds of formula (I-4), wherein Q is Qb.

In one preferred group of compounds of formula I-4b, $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-4b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C(O)CH_3$.

In another preferred group of compounds of formula I-4b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —NHC(O)$CH_3$. Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

A further preferred group of compounds of formula I-4b are those compounds wherein RB is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C(O)CH_3$.

A further preferred group of compounds of formula I-4b are those compounds wherein RB is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

The present invention also provides agrochemically acceptable salts, stereoisomers, enantiomers, tautomers and N-oxides of the compounds of formula I-4.

Another preferred group of compounds of formula I is represented by the compounds of formula I-5

(I-5)

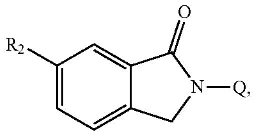

wherein Q is a radical selected from the group consisting of formula Qa and Qb

Qa

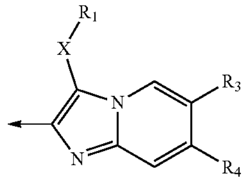

Qb

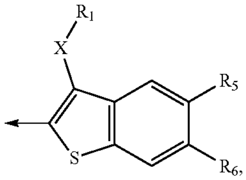

wherein the arrow denotes the point of attachment to the nitrogen atom of the bicyclic ring; and $R_2$, X, $R_1$, $R_3$, $R_4$, $R_5$, $R_6$, $R_7$ and $R_8$ are as defined under formula I above.

In one preferred group of compounds of formula I-5, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; and X is S or $SO_2$.

In another preferred group of compounds of formula I-5, $R_1$ is ethyl or cyclopropylmethyl; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and X is S or $SO_2$.

In a further preferred group of compounds of formula I-5, $R_1$ is ethyl; X is $SO_2$; and $R_2$ is —$CF_3$, —$CF_2CF_3$, —$SCF_3$, —$SOCF_3$, —$SO_2CF_3$, —$OCHF_2$, —$OCF_3$ or —$OSO_2CF_3$.

In a further preferred group of compounds of formula I-5, $R_1$ is ethyl; X is $SO_2$; and $R_2$ is —$CF_3$, —$SO_2CF_3$, —$OCHF_2$, or —$OCF_3$.

One preferred group of compounds according to this embodiment are compounds of formula (I-5a) which are compounds of formula (I-5), or of any of the preferred embodiments of the compounds of formula (I-5), wherein Q is Qa.

In one preferred group of compounds of formula I-5a, $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-5a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

In another preferred group of compounds of formula I-5a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —$NHC(O)CH_3$. Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —$NHC(O)CH_3$.

A further preferred group of compounds of formula I-5a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —$NHC(O)CH_3$ or —$NCH_3C(O)CH_3$.

A further preferred group of compounds of formula I-5a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$.

An outstanding group of compounds of formula I-5a are the compounds of formula (I-5a-2) wherein:

$R_2$ is —$CF_3$, —$OCHF_2$, —$OCF_3$ or —$SO_2CF_3$;

X is S or $SO_2$; preferably X is $SO_2$;

$R_1$ is ethyl; and $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; preferably $R_3$ is bromo, trifluoromethyl, 1,1-difluoroethyl, 1-cyanocyclopropyl, 1-cyano-1-methyl-ethoxy or methoxy; or $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —$NHC(O)CH_3$; preferably $R_4$ is trifluoromethyl, 1-cyanocyclopropyl, or 2,2,2-trifluoroethoxy.

An outstanding group of compounds of formula I-5a-2 are those wherein:

X is $SO_2$;

$R_3$ is hydrogen; and $R_4$ is trifluoromethyl, 1-cyanocyclopropyl or 2,2,2-trifluoroethoxy.

Another outstanding group of compounds of formula I-5a-2 are those wherein:

X is $SO_2$;

$R_4$ is hydrogen; and $R_3$ is bromo, trifluoromethyl, 1,1-difluoroethyl, 1-cyanocyclopropyl, 1-cyano-1-methyl-ethoxy or methoxy.

Another preferred group of compounds according to this embodiment are compounds of formula (I-5b) which are compounds of formula (I-5), or of any of the preferred embodiments of the compounds of formula (I-5), wherein Q is Qb.

In one preferred group of compounds of formula I-5b, $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —$N(R_7)C(=O)R_8$; and $R_7$ and $R_8$ are, independently from each other, hydrogen or $C_1$-$C_4$ alkyl.

In another preferred group of compounds of formula I-5b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —$NHC(O)CH_3$ or —$NCH_3C(O)CH_3$.

In another preferred group of compounds of formula I-5b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —$NHC(O)CH_3$. Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

A further preferred group of compounds of formula I-5b are those compounds wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$.

A further preferred group of compounds of formula I-5b are those compounds wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

The present invention also provides agrochemically acceptable salts, stereoisomers, enantiomers, tautomers and N-oxides of the compounds of formula I-5.

Another preferred group of compounds of formula I is represented by the compounds of formula I-6

(I-6)

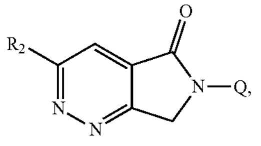

wherein Q is a radical selected from the group consisting of formula Qa and Qb

Qa

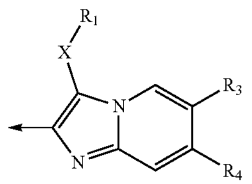

Qb

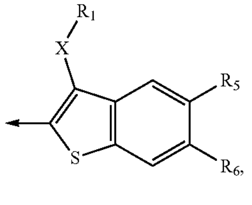

wherein the arrow denotes the point of attachment to the nitrogen atom of the bicyclic ring; and $R_2$, X, $R_1$, $R_3$, $R_4$, $R_5$, $R_6$, $R_7$ and $R_8$ are as defined under formula I above.

In one preferred group of compounds of formula I-6, $R_1$ is $C_1$-$C_4$ alkyl or cyclopropyl-$C_1$-$C_4$ alkyl; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; $R_2$ is $C_1$-$C_2$ haloalkyl, $C_1$-$C_2$ haloalkylsulfanyl, $C_1$-$C_2$ haloalkylsulfinyl, $C_1$-$C_2$ haloalkylsulfonyl, $C_1$-$C_2$ haloalkoxy or $C_1$-$C_2$ haloalkylsulfonyloxy; and X is S or $SO_2$.

In another preferred group of compounds of formula I-6, $R_1$ is ethyl or cyclopropylmethyl; $R_2$ is $C_1$-$C_2$ fluoroalkyl, $C_1$-$C_2$ fluoroalkylsulfanyl, $C_1$-$C_2$ fluoroalkylsulfinyl, $C_1$-$C_2$ fluoroalkylsulfonyl, $C_1$-$C_2$ fluoroalkoxy or $C_1$-$C_2$ fluoroalkylsulfonyloxy; and X is S or $SO_2$.

In a further preferred group of compounds of formula I-6, $R_1$ is ethyl; X is $SO_2$; and $R_2$ is —$CF_3$, —$CF_2CF_3$, —$SCF_3$, —$SOCF_3$, —$SO_2CF_3$, —$OCHF_2$, —$OCF_3$ or —$OSO_2CF_3$.

In a further preferred group of compounds of formula I-6, $R_1$ is ethyl; X is $SO_2$; and $R_2$ is —$CF_3$, —$SO_2CF_3$, —$OCHF_2$, or —$OCF_3$.

One preferred group of compounds according to this embodiment are compounds of formula (I-6a) which are compounds of formula (I-6), or of any of the preferred embodiments of the compounds of formula (I-6), wherein Q is Qa.

In one preferred group of compounds of formula I-6a, $R_3$ and $R_4$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —N($R_7$)C(═O)$R_8$; and $R_7$ and $R_8$ are, independently from each other, hydrogen or $C_1$-$C_4$ alkyl.

In another preferred group of compounds of formula I-6a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3C$(O)$CH_3$.

In another preferred group of compounds of formula I-6a, $R_3$ and $R_4$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —NHC(O)$CH_3$. Also preferred is when one of $R_3$ or $R_4$ is hydrogen and the other one of $R_3$ or $R_4$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

A further preferred group of compounds of formula I-6a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3C$(O)$CH_3$.

A further preferred group of compounds of formula I-6a are those compounds wherein $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

Another preferred group of compounds according to this embodiment are compounds of formula (I-6b) which are compounds of formula (I-6), or of any of the preferred embodiments of the compounds of formula (I-6), wherein Q is Qb.

In one preferred group of compounds of formula I-6b, $R_5$ and $R_6$ are, independently from each other, hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ cyanoalkoxy, cyano, $C_1$-$C_4$ alkoxy, $C_1$-$C_6$ haloalkoxy, or —N($R_7$)C(═O)$R_8$; and $R_7$ and $R_8$ are, independently from each other, hydrogen or $C_1$-$C_4$ alkyl.

In another preferred group of compounds of formula I-6b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, cyano, methoxy, isopropoxy, difluoromethoxy, trifluoroethoxy, difluoroethoxy, —NHC(O)$CH_3$ or —$NCH_3$C(O)$CH_3$.

In another preferred group of compounds of formula I-6b, $R_5$ and $R_6$ are, independently from each other, hydrogen, bromo, methyl, trifluoromethyl, difluoroethyl, cyclopropyl, cyanocyclopropyl, cyanisopropyl, cyanoisopropoxy, methoxy, isopropoxy, difluoromethoxy, trifluoroethoxy, difluoroethoxy, or —NHC(O)$CH_3$. Also preferred is when one of $R_5$ or $R_6$ is hydrogen and the other one of $R_5$ or $R_6$ is selected from bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy and —NHC(O)$CH_3$.

A further preferred group of compounds of formula I-6b are those compounds wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3$C(O)$CH_3$; or wherein $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, cyano, methoxy, isopropoxy, difluoromethoxy, 2,2,2-trifluoroethoxy, 2,2-difluoroethoxy, —NHC(O)$CH_3$ or —$NCH_3$C(O)$CH_3$.

A further preferred group of compounds of formula I-6b are those compounds wherein $R_6$ is hydrogen and $R_5$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or wherein $R_5$ is hydrogen and $R_6$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

The present invention also provides agrochemically acceptable salts, stereoisomers, enantiomers, tautomers and N-oxides of the compounds of formula I-6.

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile, improved physico-chemical properties, or increased biodegradability or environmental profile). In particular, it has been surprisingly found that certain compounds of formula (I) may show an advantageous safety profile with respect to non-target arthropods, in particular pollinators such as honey bees, solitary bees, and bumble bees. Most particularly, *Apis mellifera*.

In another aspect the present invention provides a composition comprising an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I), (1-1), (1-2), (1-3), (1-4), (1-5) and (1-6) (above), and, optionally, an auxiliary or diluent.

In a further aspect the present invention provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I), (I-1), (I-2), (I-3), (I-4), (I-5) and (I-6) (above) or a composition as defined above.

In a yet further aspect, the present invention provides a method for the protection of plant propagation material from the attack by insects, acarines, nematodes or molluscs, which comprises treating the propagation material or the site, where the propagation material is planted, with a composition as defined above.

The process according to the invention for preparing compounds of formula I is carried out in principle by methods known to those skilled in the art. More specifically, and as described in schemes A and B, the subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of the sulfide compounds I to produce the sulfone compounds I. Such oxidation reactions are disclosed, for example, in WO 2013/018928.

Scheme A

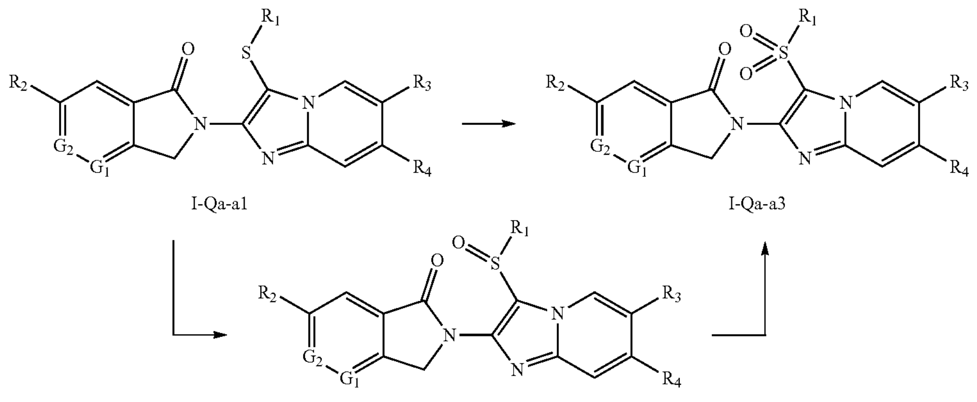

I-Qa-a1 I-Qa-a3

I-Qa-a2

The chemistry described previously in scheme A to access compounds of formula I-Qa-a2 and I-Qa-a3 from compounds of formula I-Qa-a1, wherein $G_1$, $G_2$, $R_1$, $R_2$, $R_3$ and $R_4$ are as defined in formula I, can be applied analogously (scheme B) for the preparation of compounds of formula I-Qb-b2 and I-Qb-b3 from compounds of formula I-Qb-b1, wherein $G_1$, $G_2$, $R_1$, $R_2$, $R_5$ and $R_6$ are as defined in formula I.

Scheme B

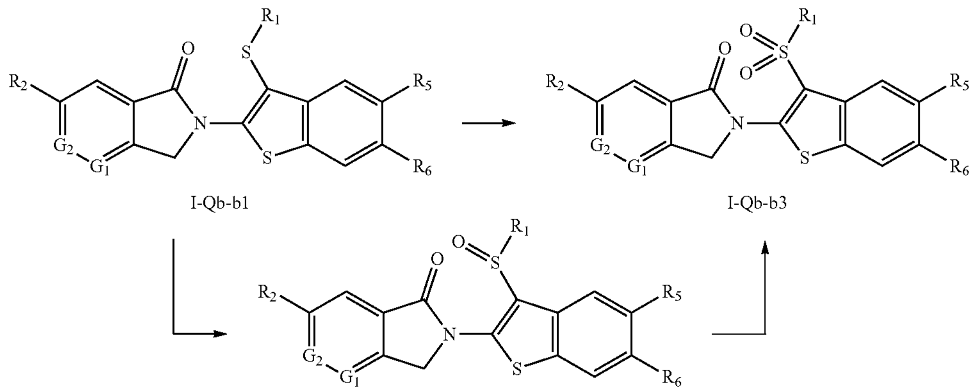

I-Qb-b1 I-Qb-b3

I-Qb-b2

Compounds of formula I wherein $R_1$, $G_1$, $G_2$ and Q are defined as under formula I above may be prepared (scheme 1)

Scheme 1

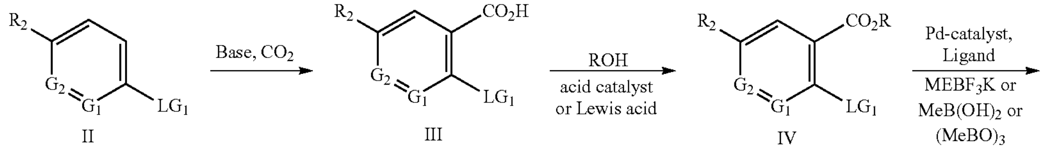

II III IV $LG_1$ = Cl, Br, I

-continued

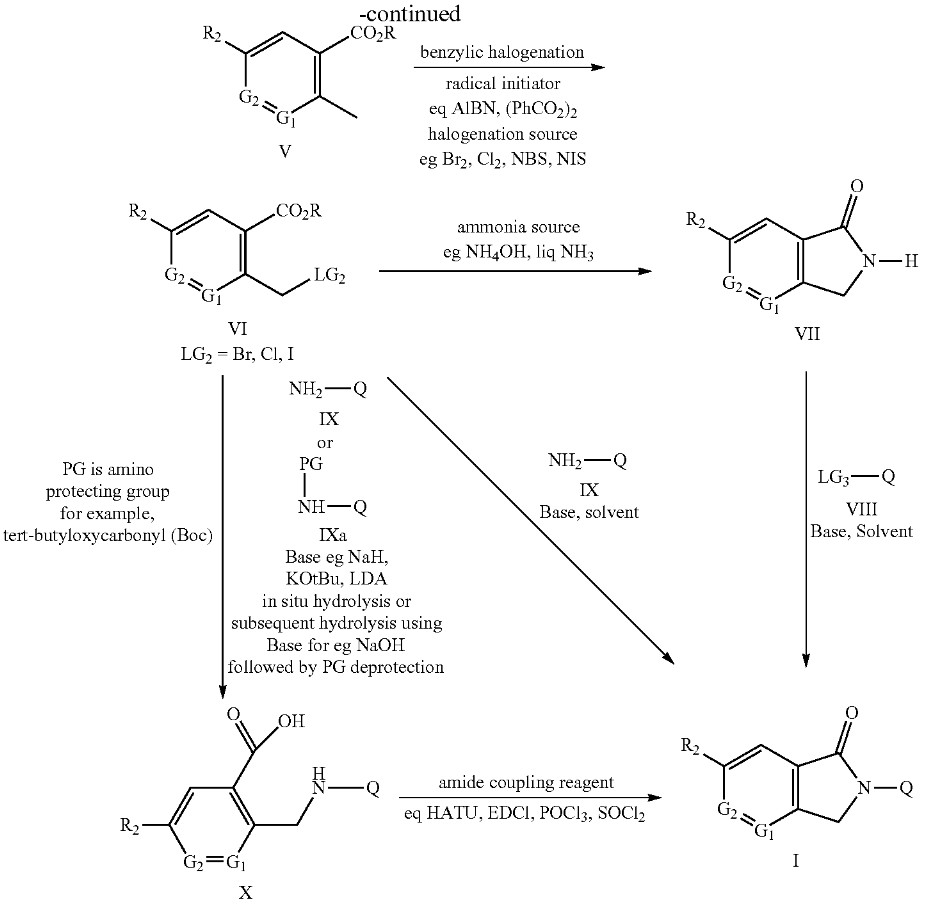

by reacting compounds of formula VII, wherein $R_2$, $G_1$ and $G_2$ are defined in formula I above, with compounds of formula VIII, wherein Q is as defined in formula I above, and in which $LG_3$ is a halogen (or a pseudo-halogen leaving group, such as a triflate), in the presence of a base, such as sodium carbonate, potassium carbonate or cesium carbonate, or sodium hydride, in an appropriate solvent such as for example tetrahydrofuran, dioxane, N,N-dimethylformamide, N,N-dimethylacetamide or acetonitrile, at temperatures between 0 and 150° C., optionally under microwave irradiation.

Alternatively, compounds of formula I wherein $R_2$, $G_1$, $G_2$ and Q are defined as under formula I above may be prepared by reacting compounds of formula VII, wherein $R_2$, $G_1$ and $G_2$ are defined as formula I above, with compounds of formula VIII, wherein Q is as defined in formula I above, and in which $LG_3$ is a halogen (or a pseudo-halogen leaving group, such as a triflate), preferably bromo or iodo, in the presence of a base, such as sodium carbonate, potassium carbonate or cesium carbonate, or potassium tert-butoxide, in the presence of a metal catalyst, either a copper catalyst, for example copper(I) iodide, optionally in the presence of a ligand, for example a diamine ligands (e.g. N,N'-dimethylethylenediamine or trans-cyclohexyldiamine) or dibenzylideneacetone (dba), or 1,10-phenanthroline, at temperatures between 30-180° C., optionally under microwave irradiation, or a palladium catalyst, for example palladium (II)acetate, bis(dibenzylideneacetone)palladium(0) (Pd(dba)$_2$) or tris(dibenzylideneacetone)dipalladium(0) ($Pd_2(dba)_3$ (optionally in form of a chloroform adduct), or a palladium pre-catalyst such as for example tert-BuBrettPhos Pd $G_3$ [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd $G_3$ [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation. The above reaction may be carried out in the presence of a solvent such as toluene, N,N-dimethylformamide DMF, N-methyl pyrrolidone NMP, dimethyl sulfoxide DMSO, dioxane, tetrahydrofuran THF, and are described in the literature, for example in WO2012031004, WO2009042907 and Synthetic Communications 2011, 41: 67-72.

Alternatively, compounds of formula I wherein $R_2$, $G_1$, $G_2$ and Q are defined as under formula I above may be prepared (scheme 1) by reacting compounds of formula VI, wherein $R_2$, $G_1$ and $G_2$ are as defined in formula I above, and $LG_2$ is a leaving group, for example bromo Br, chloro Cl or iodo I (preferably bromo), and R is $C_1$-$C_6$ alkyl, benzyl or a phenyl group, with compounds of formula IX, wherein Q is as defined in formula I above, in the presence of a base, such as sodium carbonate, potassium carbonate or cesium carbonate, or sodium hydride, or N,N-diisopropylethylamine or potassium tert-butoxide KOtBu, and in the presence of a solvent such as ethanol, methanol, dioxane, toluene, acetonitrile, DMF, N,N-dimethylacetamide DMA, DMSO, or THF, at temperatures between 0 and 150° C., optionally under microwave irradiation. Such reactions proceed via nucleophilic substitution and subsequent cyclization and are also reported in the literature, for example in WO2009042907.

Alternatively, compounds of formula I wherein $R_2$, $G_1$, $G_2$ and Q are defined as under formula I above can be prepared (scheme 1) by cyclizing compounds of formula X, wherein $R_2$, $G_1$, $G_2$ and Q are as defined in formula I, for example in the presence of phosphorus oxychloride (other amide coupling reagent may also be used, such as thionyl chloride $SOCl_2$, HATU or EDCl), optionally in the presence of a base, such as triethylamine, pyridine or Hunig's base, optionally in the presence of a solvent or diluent, such as toluene or xylene, at temperatures between 0 and 180° C., preferably between 20 and 120° C.

Compounds of formula I, wherein $R_2$, $G_1$, $G_2$ and Q are defined as under formula I above, can also be prepared (scheme 2)

Scheme 2

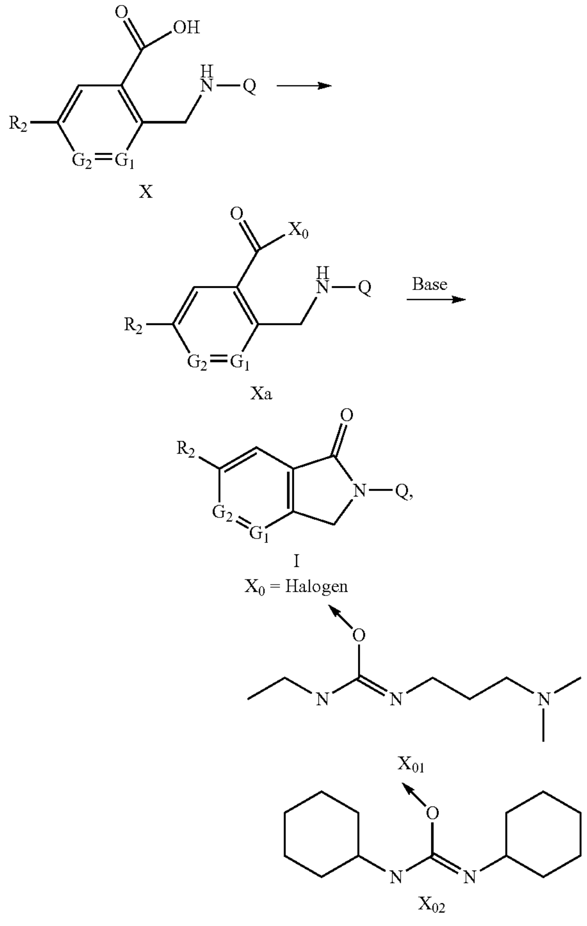

X

Xa

I $X_{01}$ $X_{02}$ by cyclization of the formula Xa wherein $R_2$, $G_1$, $G_2$ and Q are defined as under formula I above, and in which $X_0$ is halogen, preferably chlorine, or $X_0$ is either $X_{01}$ or $X_{02}$, in the presence of a base, such as triethylamine, N,N-diisopropyl-ethylamine or pyridine, optionally in the presence of a catalyst (such as 4-dimethylaminopyridine DMAP), in inert solvents such as dichloromethane, tetrahydrofuran, dioxane, N,N-dimethylformamide, N,N-dimethylacetamide, acetonitrile, ethyl acetate or toluene, at temperatures between 0 and 50° C. Certain bases, such as pyridine and triethylamine, may be employed successfully as both base and solvent.

Compounds of formula Xa, wherein $R_2$, $G_1$, $G_2$ and Q are defined as under formula I above, and in which $X_0$ is halogen, preferably chlorine, or $X_0$ is either $X_{01}$ or $X_{02}$, can be prepared by activation of compound of formula X, wherein $R_2$, $G_1$, $G_2$ and Q are defined as under formula I above, by methods known to those skilled in the art and described in, for example, Tetrahedron, 2005, 61 (46), 10827-10852. Preferred is the formation of an activated species Xa, wherein $R_2$, $G_1$, $G_2$ and Q are defined as under formula I above, and in which $X_0$ is halogen, preferably chlorine. For example, compounds Xa where $X_0$ is halogen, preferably chlorine, are formed by treatment of X with, for example, oxalyl chloride $(COCl)_2$ or thionyl chloride $SOCl_2$, in the presence of catalytic quantities of N,N-dimethylformamide DMF in inert solvents, such as methylene chloride $CH_2Cl_2$ or tetrahydrofuran THF, at temperatures between 20 to 100° C., preferably around 25° C. Alternatively, treatment of compounds of formula X with, for example, 1-ethyl-3-(3-dimethylaminopropyl)carbo-diimide EDC or dicyclohexyl carbodiimide DCC will generate an activated species Xa, wherein $X_0$ is $X_{01}$ or $X_{02}$ respectively, in an inert solvent, such as pyridine or tetrahydrofuran THF, optionally in the presence of a base, such as triethylamine, at temperatures between 50-180° C.

Compounds of formula VII, wherein $R_2$, $G_1$ and $G_2$ are as defined in formula I above can be prepared (scheme 1) by reacting compounds of formula VI, wherein $R_2$, $G_1$ and $G_2$ are as defined in formula I above, and $LG_2$ is a leaving group, for example Br, Cl or I (preferably bromo), and R is $C_1$-$C_6$ alkyl, benzyl or a phenyl group, with ammonia or surrogates of ammonia, for example $NH_4OH$, in the presence of a solvent such as ethanol, methanol, dioxane, toluene, DMF, DMA, DMSO, and THF, at temperatures between 0 and 150° C., optionally under microwave irradiation.

Compounds of formula X, wherein $R_2$, $G_1$, $G_2$ and Q are defined as under formula I above, can be prepared (scheme 1) by nucleophilic substitution reaction of compound of formula VI, wherein $R_2$, $G_1$ and $G_2$ are as defined in formula I above, and $LG_2$ is a leaving group, for example Br, Cl or I (preferably bromo), and R is $C_1$-$C_6$ alkyl, benzyl or a phenyl group, with an amino compound of formula IX, wherein Q is as defined in formula I above, under conditions described above, followed by in situ hydrolysis of the formed intermediate ester of formula XVII, wherein $R_2$, $G_1$, $G_2$ and Q are defined as under formula I above, and in which R is $C_1$-$C_6$ alkyl, benzyl or a phenyl group.

(XVII)

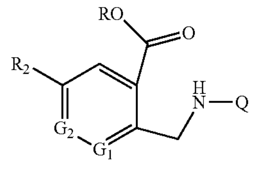

The in situ generated unhydrolyzed ester compound of formula XVII may be isolated and can also be converted via saponification reaction, in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), to form the carboxylic acid of formula X. Alternatively, Krapcho-type conditions (e.g. heating the substrate XVII in the presence of sodium or lithium chloride in N-methyl pyrrolidone or aqueous dimethylsulfoxide DMSO, optionally under microwave irradiation) can also be used to convert compounds of formula XVII into compounds of formula X. The direct conversion of compound of formula VI to compound of formula X can be carried out in the presence of base, such as sodium hydride, KOtBu, butyllithium, or lithium diisopropylamide amongst others, and in the presence of a solvent such as dioxane, DMF, DMA, DMSO, or THF, at temperatures between −30 and 150° C.

The above reaction for the preparation of compounds of formula X can also be carried out by reacting compounds of formula VI, with compounds of formula IXa, wherein Q is as defined in formula I above, and PG is an amino protecting group, for example tert-butyloxycarbonyl (BOC), under similar conditions as described above (as for the preparation of compounds of formula X by reacting compounds of formula VI and compounds of formula IX), followed by deprotection of the amino protecting group PG. The deprotection of the amino protecting groups is well known to those skilled in the art, for example BOC protecting groups can be removed in the presence of acids, such as hydrochloric acid, or trifluoroacetic acid, optionally in the presence of an inert solvent, such as dichloromethane, tetrahydrofuran, dioxane or benzotrifluoride, at temperatures between 0 and 70° C.

This process of forming compounds of formula X (and I) from compounds of formula VI and IXa is detailed in scheme 2a and reflecting the particular situation wherein the group PG of IXa is tert-butyloxycarbonyl (BOC), defining compounds of formula XIX, wherein Q is as defined in formula I above.

Scheme 2a (substituent definitions mentioned previously remain valid)

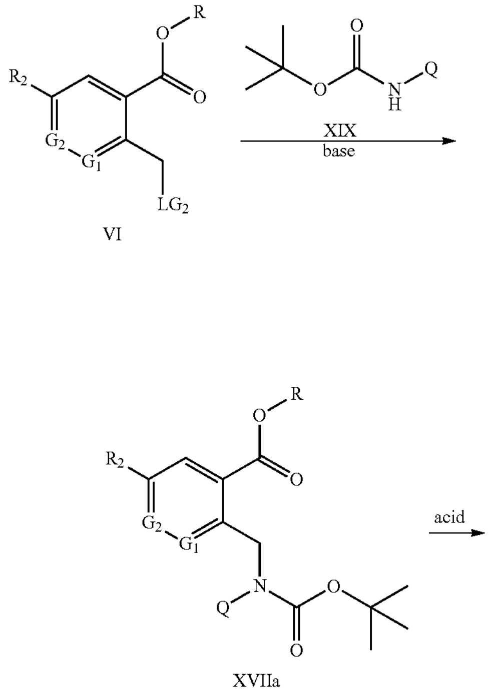

VI XIX XVIIa

-continued

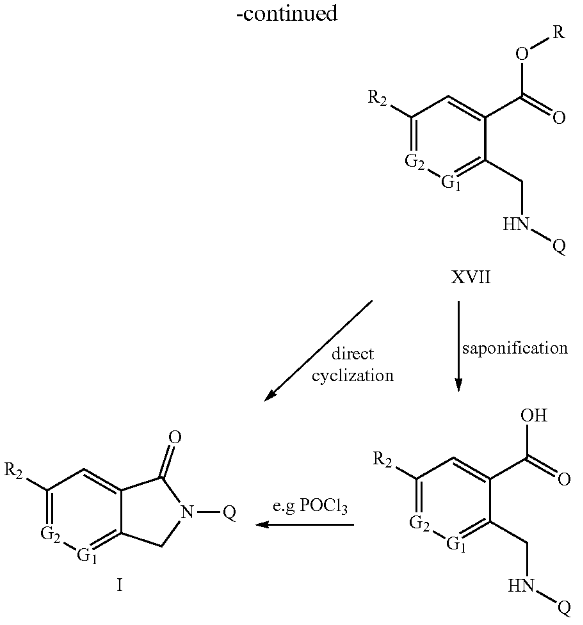

XVII I X

Compounds of formula VI and compounds of formula XIX react to compounds of formula XVIIa, in the presence of a base, such as sodium carbonate, potassium carbonate or cesium carbonate, or sodium hydride, or N,N-diisopropylethylamine or potassium tert-butoxide KOtBu, in the presence of a solvent such as ethanol, methanol, dioxane, toluene, acetonitrile, DMF, N,N-dimethylacetamide DMA, DMSO, or THF, at temperatures between 0 and 150° C., optionally under microwave irradiation.

tert-Butyloxycarbonyl (BOC) group removal in compounds of formula XVIIa, mediated by acids, such as hydrochloric acid, or trifluoroacetic acid, optionally in the presence of an inert solvent, such as dichloromethane, tetrahydrofuran, dioxane or benzotrifluoride, at temperatures between 0 and 70° C., generates compounds of formula XVII. Saponification of compounds of formula XVII in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), forms the carboxylic acids of formula X (alternatively, Krapcho-type conditions as described above may be used). Cyclization of compounds of formula X to compounds of formula I is achieved, for example, in the presence of phosphorus oxychloride (other amide coupling reagent may also be used, such as thionyl chloride $SOCl_2$, HATU or EDCI), optionally in the presence of a base, such as triethylamine, pyridine or Hunig's base, optionally in the presence of a solvent or diluent, such as toluene or xylene, at temperatures between 0 and 180° C. preferably between 20 and 120° C.

Alternatively, a direct cyclization of compounds of formula XVII into compounds of formula I may be achieved under conditions mentioned below in scheme 6.

The subgroup of compounds of formula I, wherein $G_1$, $G_2$ and $R_2$ are as defined in formula I and wherein Q is defined as Qa, in which $R_3$, $R_4$, X and $R_1$ are as defined in formula I, may be defined as compounds of formula I-Qa (scheme 2b). Similarly, the subgroup of reactants of formula IXa, wherein PG is a tert-butyloxycarbonyl (BOC) group, and wherein Q is defined as Qa, in which $R_3$, $R_4$, X and $R_1$ are as defined in formula I, may be defined as compounds of formula XIX-Qa.

either known (see preparation descriptions disclosed in WO20/174094) or may be prepared by methods known to a person skilled in the art.

Scheme 2b

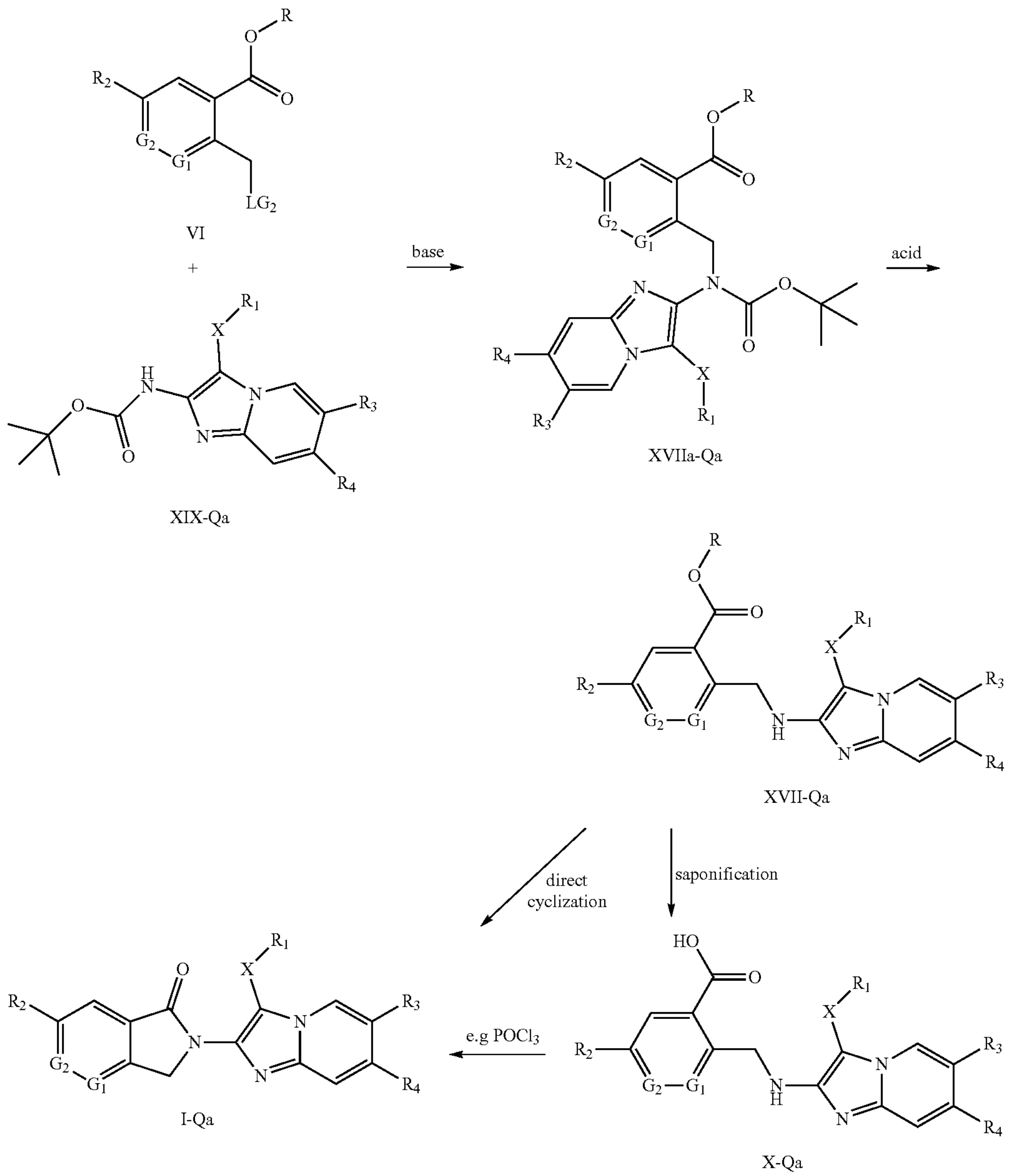

VI

XIX-Qa

XVIIa-Qa

XVII-Qa

I-Qa

X-Qa

The chemistry described previously in schemes 1, 2 and 2a to access compounds of formula I from compounds of formula VI and compounds of formula IXa via compounds of formula X, can be applied analogously (scheme 2b) for the preparation of compounds of formula I-Qa from compounds of formula VI and compounds of formula XIXa-Qa via compounds of the formula X-Qa, wherein all substituent definitions mentioned previously remain valid.

Compounds of formula VI, wherein $R_2$, $G_1$ and $G_2$ are as defined in formula I above, and $LG_2$ is a halogen leaving group, for example bromo Br, chloro Cl or iodo I (preferably bromo), and R is $C_1$-$C_6$ alkyl, benzyl or a phenyl group, are For example, compounds of formula VI, wherein $R_2$, $G_1$ and $G_2$ are as defined in formula I above, and $LG_2$ is a leaving group for example Br, Cl or I (preferably bromo), and R is $C_1$-$C_6$ alkyl, benzyl or a phenyl group, can be prepared by a radical induced benzylic halogenation of compounds of formula V, wherein $R_2$, $G_1$ and $G_2$ are as defined in formula I above, and R is $C_1$-$C_6$ alkyl, benzyl or a phenyl group. Such reaction are well known to those skilled in the art and may be carried out in the presence of electrophilic halogenating reagents, such as $Br_2$, NBS, $Cl_2$, NIS amongst others, and in the presence of radical initiator, for example AIBN (azobisisobutyronitrile), benzoyl peroxide or under photochemical conditions, and in the presence of a solvent such as toluene, xylene, acetonitrile, hexane, dichloroethane, or carbon tetrachloride, at temperatures ranging from 20° C. to the boiling point of the reaction mixture. Such reactions are known by the name of Wohl-Ziegler bromination and are reported in literature, for example in Synthesis 2015, 47:1280-1290 and J. Am. Chem. Soc. 1963, 85 (3):354-355.

Compounds of formula V, wherein $R_2$, $G_1$ and $G_2$ are as defined in formula I above, and R is $C_1$-$C_6$ alkyl, benzyl or a phenyl group, can be prepared (scheme 1) by a Suzuki reaction, which involves for example, reacting compounds of formula IV, wherein $R_2$, $G_1$ and $G_2$ are as defined in formula I above, and $LG_1$ is a halogen Br, Cl, I (preferably Cl), and R is $C_1$-$C_6$ alkyl, benzyl or a phenyl group, with trimethylboroxine or potassium methyltrifluoroborate amongst other methyl boronic acid equivalent. The reaction may be catalyzed by a palladium based catalyst, for example tetrakis(triphenyl-phosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)] palladium(II) (XPhos palladacycle), in the presence of a base, such as sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 1999, 576:147-168.

Compounds of formula IV, wherein $R_2$, $G_1$ and $G_2$ are as defined in formula I above, and $LG_1$ is a halogen Br, Cl, I (preferably Cl), and R is $C_1$-$C_6$ alkyl, benzyl or a phenyl group, can be prepared (scheme 1) by reacting compounds of formula III, wherein $R_2$, $G_1$ and $G_2$ are as defined in formula I above, and $LG_1$ is a halogen Br, Cl, I (preferably Cl), and ROH, wherein R is $C_1$-$C_6$ alkyl, benzyl or a phenyl group, in the presence of acid catalyst, for example sulfuric acid, or a Lewis acid such as for example $Sc(OTf)_3$ or $FeCl_3$. Such reactions are well known to those skilled in the state of art and known by the name of Fischer esterification reaction, and are reported in literature for example in J. Org. Chem. 2006, 71:3332-3334, Chem. Commun. 1997, 351-352 and Synthesis 2008, 3407-3410. Such esterification reaction can also be carried out by reacting compounds of formula III with $TMSCHN_2$ to form compounds of formula IV, wherein $R_2$, $G_1$ and $G_2$ are as defined in formula I above, and $LG_1$ is halogen Br, Cl, I (preferably Cl), and in which R is methyl, and are reported in Angew. Chem. Int. Ed. 2007, 46:7075.

Compounds of formula III, wherein $R_2$, $G_1$ and $G_2$ are as defined in formula I above, and $LG_1$ is a halogen Br, Cl, I (preferably Cl), can be prepared (scheme 1) by a metalation reaction of compounds of formula 11, wherein $R_2$, $G_1$ and $G_2$ are as defined in formula I above, and $LG_1$ is a halogen Br, Cl, I (preferably Cl), with a suitable base, and subsequent reaction with carbon dioxide. Such a metalation reaction can be performed using bases such as, for example, organolithium compounds, such as lithium tetramethylpiperidide, lithium diisopropylamide, or sec-BuLi amongst others, at temperatures ranging from −78 to 40° C., in the presence of a solvent, such as THF, DMPU, dioxane, or 2-methyl tetrahydrofuran. Such reactions are reported in literature, for example in Tetrahedron 2004, 60(51):11869-11874.

Alternatively, compounds of formula I, wherein $G_1$, $G_2$, $R_2$ and Q are defined as under formula I above, can be prepared by performing an amidation reaction on compounds of formula X, wherein $G_1$, $G_2$, $R_2$ and Q are defined as under formula I above, following scheme 3.

Scheme 3

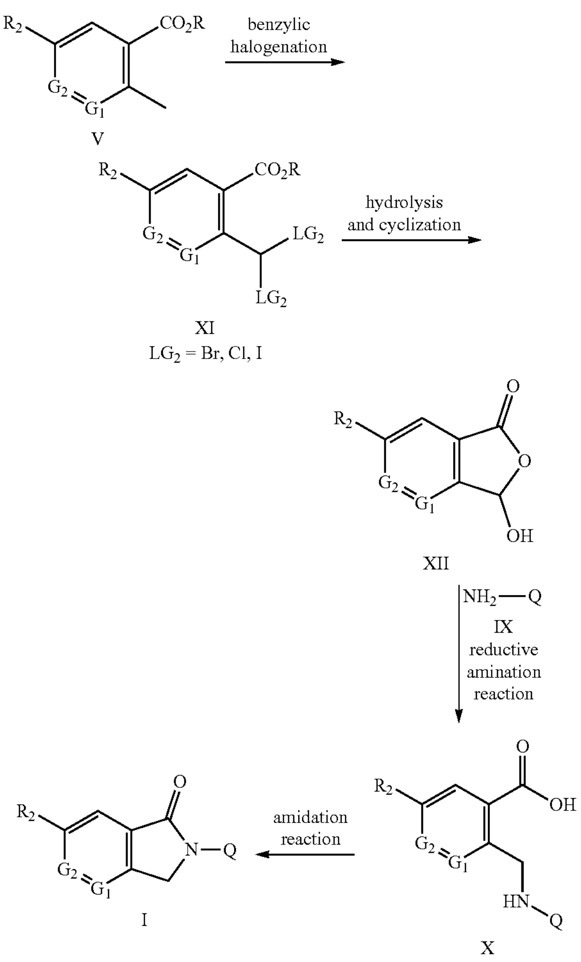

V

XI $LG_2$ = Br, Cl, I

XII

X

I

The reaction details for the transformation of compounds of formula X, wherein $G_1$, $G_2$, $R_2$ and Q are defined as under formula I, into compounds of formula I, wherein $G_1$, $G_2$, $R_2$ and Q are defined as under formula I above, are illustrated in scheme 4, and follow methods and conditions already described in scheme 2 above.

Scheme 4

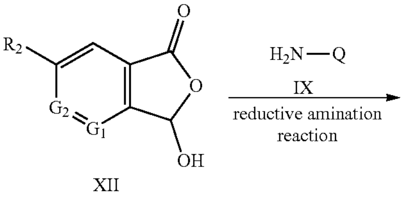

XII

-continued

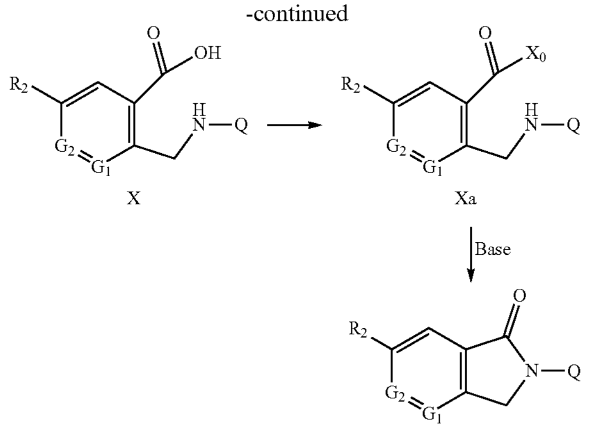

X Xa I $X_0$ = Halogen,

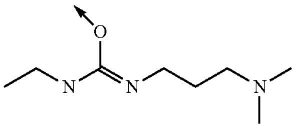

$X_{01}$

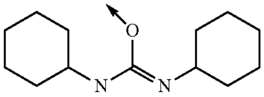

$X_{02}$

Compounds of formula X can be prepared by reacting compounds of formula XII, wherein $G_1$, $G_2$ and $R_2$ are as defined in formula I above, with compounds of formula IX, wherein Q is as defined in formula I above, under reductive amination conditions (see scheme 4). The reaction can be carried out in the presence of a reducing agent, for example sodium cyanoborohydride or sodium triacetoxyborohydride amongst others, and optionally in the presence of an acid, such as trifluoroacetic acid, formic acid or acetic acid amongst others, and at temperatures ranging from 0° C. to the boiling point of the reaction mixture. The reaction can be carried out in the presence of inert solvents such as ethanol, methanol, dioxane or tetrahydrofuran. Such reactions involving two step conversion from compounds of formula XII to compounds of formula I have been described in literature for example in Bioorganic & Medicinal Chemistry Letters 2016, 26:5947-5950.

Compounds of formula XII, wherein $G_1$, $G_2$ and $R_2$ are as defined in formula I above, can be prepared from compound of formula XI, wherein $G_1$, $G_2$ and $R_2$ are as defined in formula I above, and $LG_2$ is chloro, bromo or iodo (preferably bromo), and R is $C_1$-$C_6$ alkyl, benzyl or a phenyl group, by a hydrolysis reaction. The reaction can be carried out either under basic conditions, using metal hydroxide, for example using aqueous sodium hydroxide, in the presence of a solvent such as dioxane, tetrahydrofuran or water, and at temperature ranging from 20 to 150° C., as reported in Synlett 1992, (6), 531-533, or under aqueous acidic conditions, for example using acetic acid, hydrochloric acid or sulfuric acid, in the presence of a solvent such as water, dioxane, or halogenate solvents, such as dichloroethane, as reported in Tetrahedron 2006, 62:9589-9602. Compounds of formula XI, wherein $G_1$, $G_2$ and $R_2$ are as defined in formula I above, and $LG_2$ is chloro, bromo or iodo (preferably bromo), and R is $C_1$-$C_6$ alkyl, benzyl or a phenyl group, can be prepared from compounds of formula V, wherein $G_1$, $G_2$ and $R_2$ are as defined in formula I above, and R is $C_1$-$C_6$ alkyl, benzyl or a phenyl group, by methods and conditions similar to those described in scheme 1, for the conversion of compounds of formula V to compounds of formula VI.

Alternatively compounds of formula I, wherein $G_1$, $G_2$, $R_2$ and Q are defined as under formula I, above may be prepared Scheme 5

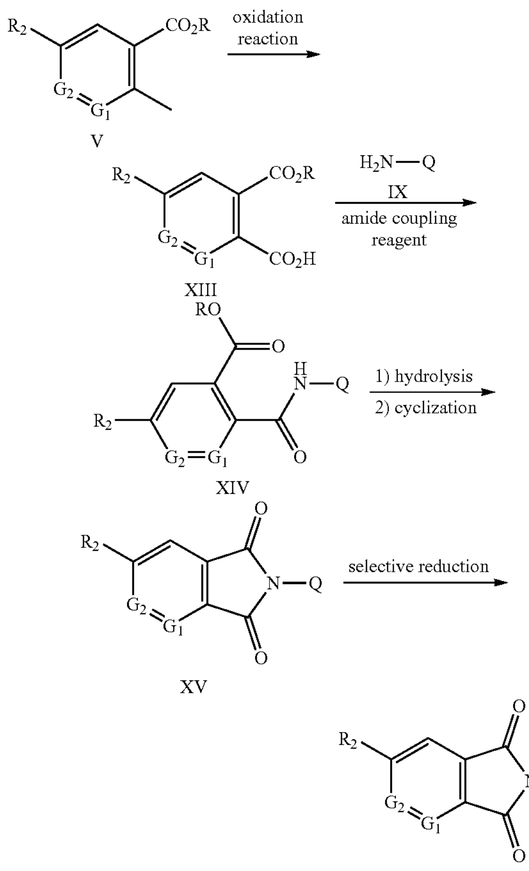

V XIII XIV XV I from compounds of formula XV, wherein $G_1$, $G_2$, $R_2$ and Q are defined as under formula I, above via selective reduction of the carbonyl functional group (scheme 5). The reaction may be carried out in the presence of a reducing agent, for example $NaBH_4$, $LiAlH_4$, palladium on carbon in the presence of hydrogen, or a combination of two reducing agent, for example $NaBH_4$ followed by triethylsilane. Such reactions have been described for example in US20100160303A1.

Compounds of formula XV, wherein $G_1$, $G_2$, $R_2$ and Q are defined as under formula I above, may be prepared from compounds of formula XIV, wherein $G_1$, $G_2$, $R_2$ and Q are defined as under formula I above, and R is $C_1$-$C_6$ alkyl, benzyl or a phenyl group, by a hydrolysis reaction and a subsequent cyclization reaction, as described in scheme 1 for the conversion of compounds of formula X to compounds of formula I.

Compounds of formula XIV, wherein $G_1$, $G_2$, $R_2$ and Q are defined as under formula I above, and R is $C_1$-$C_6$ alkyl, benzyl or a phenyl group, may be prepared by reacting compounds of formula XIII, wherein $R_2$, $G_1$ and $G_2$ are as described in formula I above, and R is $C_1$-$C_6$ alkyl, benzyl or a phenyl group, with compounds of formula IX, wherein Q is as defined in formula I above, under amidation reaction conditions already described in scheme 1.

Compounds of formula XIII, wherein $R_2$, $G_1$ and $G_2$ are as described in formula I above, and R is $C_1$-$C_6$ alkyl, benzyl or a phenyl group, may be prepared by benzylic oxidation of compounds of formula V, wherein $R_2$, $G_1$ and $G_2$ are as described in formula I above, and R is $C_1$-$C_6$ alkyl, benzyl or a phenyl group. The reaction can be carried out in the presence of oxidative reagents, such as $KMNO_4$, $nBu_4MnO_4$, or $K_2S_2O_8$, in the presence of oxygen, or under photochemical conditions in the presence of oxygen, and at temperature ranging from 20° C. to the boiling point of the reaction mixture. The reaction is carried out in the presence of inert solvent such as acetonitrile, ethyl acetate, DMSO or dichloroethane. Such reactions are known in the literature, for example in Synthesis 2017, 49:4007-4016, Synthesis 2006, 1757-1759 and IOSR Journal of Applied Chemistry 2014, 7:16-27.

Alternatively, compounds of formula I, wherein $R_2$, $G_1$, $G_2$ and Q are as defined in formula I above, Scheme 6

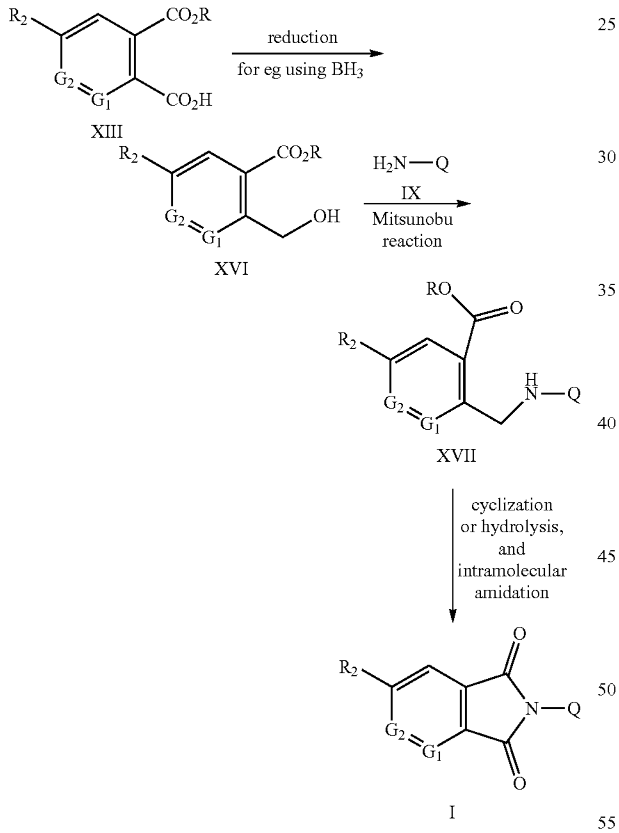

may be prepared (scheme 6) by a cyclization reaction of compounds of formula XVII, wherein $R_2$, $G_1$, $G_2$ and Q are as defined in formula I above, and R is $C_1$-$C_6$ alkyl, benzyl or a phenyl group. This reaction may be carried out in the presence of a base, such as potassium tert-butoxide, lithium diisopropylamide or sodium hydride amongst others, and at temperatures ranging from −20° C. to the boiling point of the reaction mixture, and in the presence of an inert solvent, such as tetrahydrofuran, dioxane, DMA, DMSO or DMF. Such reactions are reported, for example, in Synlett 2006 (4):591-594.

Compounds of formula XVII, wherein $R_2$, $G_1$, $G_2$ and Q are as defined in formula I above, and R is $C_1$-$C_6$ alkyl, benzyl or a phenyl group, may be prepared by reacting compounds of formula XVI, wherein $R_2$, $G_1$ and $G_2$ are as defined in formula I above, and R is $C_1$-$C_6$ alkyl, benzyl or a phenyl group, with compounds of formula IX, wherein Q is as defined in formula I above, under Mitsunobu conditions.

Such reactions are well known to those skilled in the art, and can be carried out in the presence of a phosphine reagent, such as triphenylphosphine, tributylphosphine, or polymer supported triphenyl phosphine amongst others, and in the presence of an azodicarboxylate reagent, such as diethyl azodicarboxylate or diisopropyl azodicarboxylate, and at temperature ranging from 0° C. and 100° C., in the presence of inert solvent such as acetonitrile, dichloromethane, tetrahydrofuran, or toluene. Such reactions are reported for example in Synthesis 1981(1):1-28.

Compounds of formula XVI, wherein $R_2$, $G_1$ and $G_2$ are as defined in formula I above, and R is $C_1$-$C_6$ alkyl, benzyl or a phenyl group, may be prepared by reacting compounds of formula XIII, wherein $R_2$, $G_1$ and $G_2$ are as defined in formula I above, and R is $C_1$-$C_6$ alkyl, benzyl or a phenyl group, with reducing agents, such as, for example, metal hydrides like lithium aluminumhydride, DIBAL-H, or boranes (such as diborane, or borane tetrahydrofuran complex amongst others), at temperatures ranging from 0° C. and 150° C., and in the presence of an inert solvent, such as tetrahydrofuran or dioxane. Such reactions have been reported, for example, in Tetrahedron Letters 1982, 23:2475-2478.

The compounds of formula XVII-Qa-1

(XVII-Qa-1)

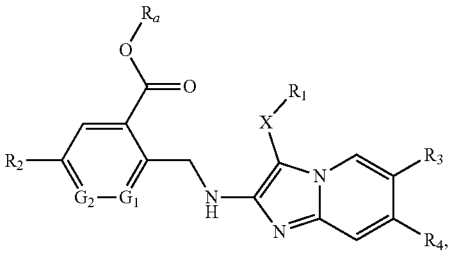

wherein $R_2$, $G_1$, $G_2$, $R_3$, $R_4$, $R_1$ and X are as defined under formula I above, and $R_a$ is hydrogen, $C_1$-$C_6$ alkyl, benzyl or phenyl are novel, especially developed for the preparation of the compounds of formula I according to the invention and therefore represent a further object of the invention. The preferences and preferred embodiments of the substituents of the compounds of formula I are also valid for the compounds of formula XVII-Qa-1. Preferably, $R_a$ is hydrogen or $C_1$-$C_6$ alkyl; even more preferably, $R_a$ is hydrogen, methyl or ethyl; most preferably $R_a$ is hydrogen.

Compounds of formula IX, wherein Q is as defined in formula I above, can be prepared Scheme 7

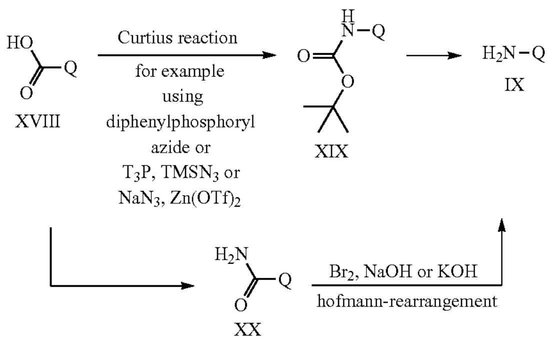

XVIII XIX IX XX by performing a deprotection reaction (BOC group removal) on compounds of formula XIX, wherein Q is as defined in formula I above (scheme 7). The reaction can be carried out in the presence of acids, such as trifluoroacetic acid, hydrochloric acid or sulfuric acid amongst others, under conditions already described above.

Compounds of formula XIX, wherein Q is as defined in formula I above, may be prepared by the reaction of compounds of formula XVIII, wherein Q is as defined in formula I above, with an organo-azide, in the presence of a suitable base and tert-butanol t-BuOH, in the presence of a coupling agent, optionally in the presence of a Lewis acid, and in the presence of an inert solvent, at temperatures between 50° C. and the boiling point of the reaction mixture. The reaction can be carried out in the presence of a coupling agent such as $T_3P$, or via activation of the carboxylic acid with $SOCl_2$ or oxalyl chloride, or other coupling agent as described in scheme 2 for the conversion of compounds of formula X into compounds of formula Xa. Examples of an organo-azide include $TMSN_3$, sodium azide, or tosyl azide, and a suitable solvent may be toluene, xylene, THE or acetonitrile. Examples of a suitable Lewis acid may include $Zn(OTf)_2$, $Sc(OTf)_2$, or $Cu(OTf)_2$ amongst others.

Compounds of formula XIX can also be prepared by reacting compounds of formula XVIII with diphenylphosphorylazide, in the presence of an organic base, such as triethylamine or diisopropylethylamine amongst others, in the presence of tert-butanol t-BuOH and an inert solvent, for example a halogenated solvent such as dichloromethane, dichloroethane, or cyclic ethers such as tetrahydrofuran amongst others, at temperatures ranging from 50° C. to the boiling point of the reaction mixture. Such reactions of converting carboxylic acids to BOC protected amines are well known to those skilled in the art by the name of Curtius reaction, and are reported, for example, in Org. Lett. 2005, 7:4107-4110; J. Med. Chem 2006, 49(12):3614-3627; J. Am. Chem. Soc. 1972, 94(17):6203-6205.

Compounds of formula IX, wherein Q is as defined in formula I above, may also be prepared from compounds of formula XX, wherein Q is as defined in formula I above, by a Hofmann-rearrangement reaction. The reaction can be carried out in the presence of a base, for example metal hydroxides, such as aqueous sodium hydroxide or potassium hydroxide, or organic bases such as DBU (1,8-diazabicyclo (5.4.0)undec-7-ene), and in the presence of electrophilic halogenating reagents, such as chlorine, bromine or N-bromosuccinimide, and at temperatures ranging from 20° C. to the boiling point of the reaction mixture. Such reactions are known by the name of Hofmann-rearrangement and are reported in literature, for example in Chem. Ber. 1881, 14:2725.

Compounds of formula XX, wherein Q is as defined in formula I above, can be prepared by the reaction of compounds of formula XVIII, wherein Q is as defined in formula I above, with ammonia, for example $NH_4OH$, $NH_3$, or other ammonia surrogates, in the presence of a carboxylic acid activating agent as described in scheme 2 above.

The subgroup of compounds of formula XIX, wherein Q is Qa, in which $R_3$, $R_4$, X and $R_1$ are as defined in formula I, can be defined as compounds of formula XIX-Qa. Such compounds of formula XIX-Qa (XIX-Qa)

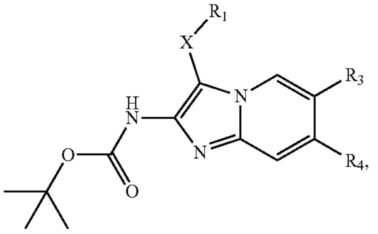

wherein $R_3$, $R_4$, $R_1$ and X are as defined under formula I above, are novel, especially developed for the preparation of the compounds of formula I according to the invention and therefore represent a further object of the invention. The preferences and preferred embodiments of the substituents of the compounds of formula I are also valid for the compounds of formula XIX-Qa. Most preferably X is $SO_2$, $R_1$ is ethyl and $R_3/R_4$ are as described in table Q.

The subgroup of compounds of formula XVIII, wherein Q is Qa, in which $R_3$, $R_4$, X and $R_1$ are as defined in formula I, can be defined as compounds of formula XVIII-a (scheme 8). Such compounds of formula XVIII-a are either known in the literature, or they can be prepared by following scheme 8 using analogous methods and conditions as described in, for example, WO2017/061497, WO2018/052136, WO2019/201921, WO2019/175046, WO2019/068572.

Scheme 8

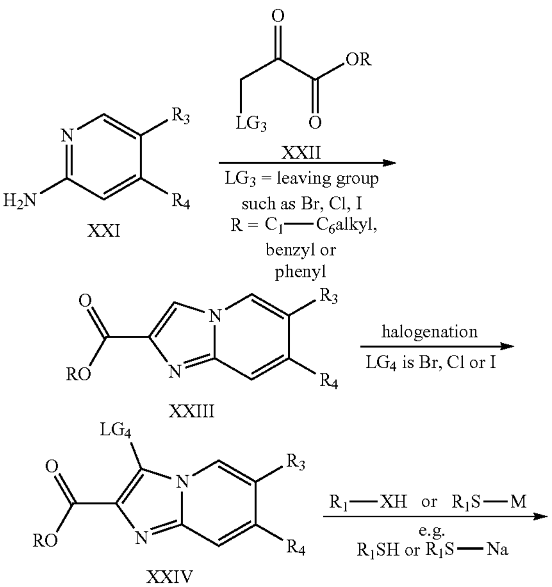

XXI XXII XXIII XXIV

-continued

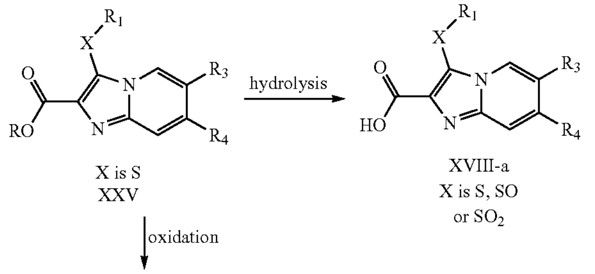

X is S
XXV

XVIII-a
X is S, SO or $SO_2$

-continued

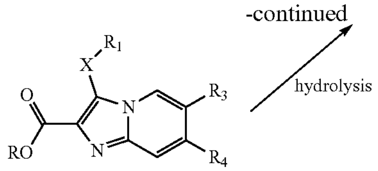

X is SO or $SO_2$
XXVI

The subgroup of compounds of formula XVIII, wherein Q is Qb, in which $R_5$, $R_6$, X and $R_1$ are as defined in formula I, can be defined as compounds of formula XVIII-b (scheme 9). Such compounds of formula XVIII-b are either known in the literature, or they can be prepared by following scheme 9 using analogous methods and conditions as described in, for example, WO2016/142327, WO2017/001311, Organic & Biomolecular Chemistry 2016, 14(3):895-904, Future Medicinal Chemistry 2017, 9(5):443-468, J. Org. Chem. 1975, 40(21), 3037-3045 and Bioorganic Chemistry 2017, 72:102-115.

Scheme 9

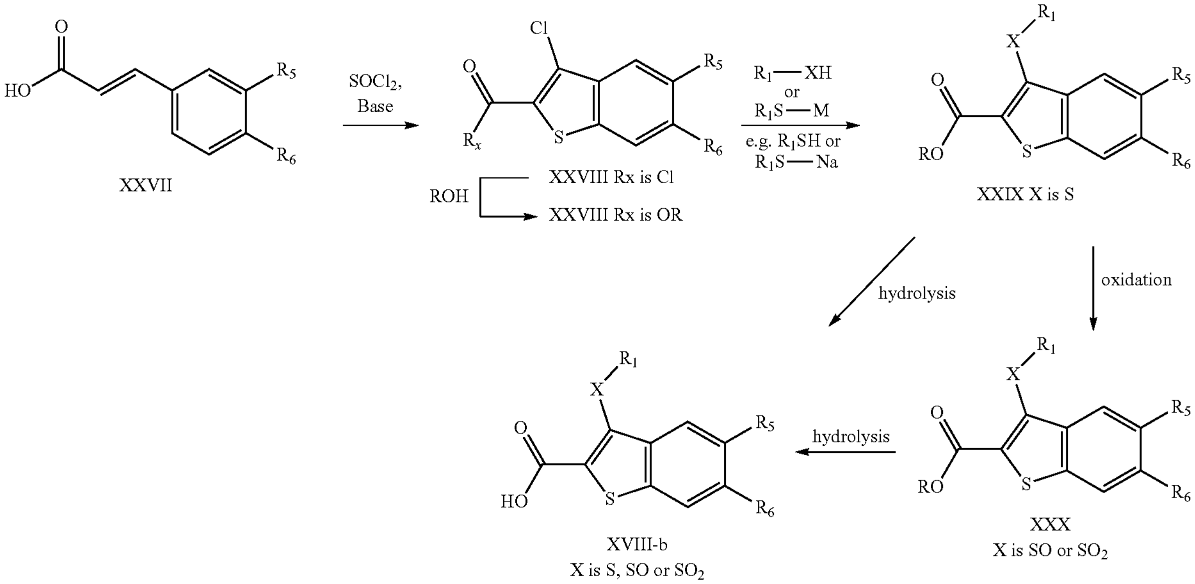

XXVII

XXIX X is S

XVIII-b
X is S, SO or $SO_2$

XXX
X is SO or $SO_2$

The subgroup of compounds of formula I, wherein $G_1$, $G_2$ and $R_2$ are as defined in formula I above, and wherein Q is defined as Qa, in which $R_3$, $R_4$, X and $R_1$ are as defined in formula I, may be defined as compounds of formula I-Qa (scheme 10).

Scheme 10

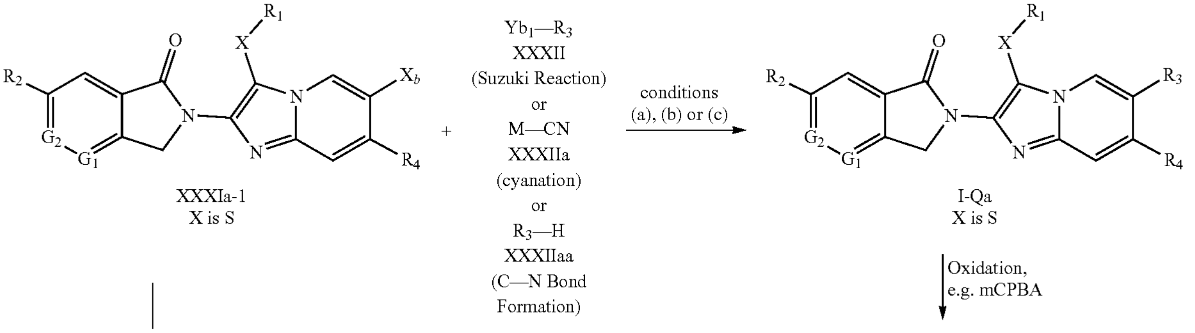

XXXIa-1
X is S

I-Qa
X is S

-continued

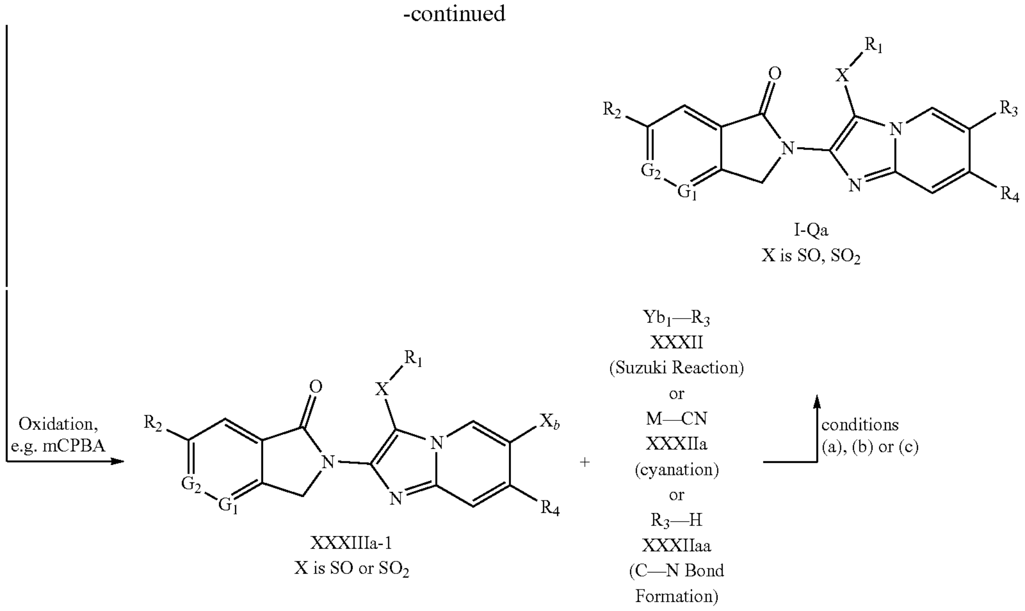

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

(b) Cyanation: cyanating reagent (e.g. NaCN, $Zn(CN)_2$, $K_4[Fe(CN)_6]$, Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

In the particular situation within scheme 10 when $R_3$ is —$N(R_7)COR_8$, wherein $R_7$ and $R_8$ are as defined in formula I, then compounds of formula I-Qa, wherein X is SO or $SO_2$, may be prepared from compounds of formula XXXIIIa-1, wherein $R_1$, $R_2$, $G_1$, $G_2$ and $R_4$ are as defined in formula I, and in which X is SO or $SO_2$, and wherein $X_b$ is a leaving group like, for example, chlorine, bromine or iodine (preferably chlorine or bromine), or an aryl- or alkylsulfonate such as trifluoromethanesulfonate, by reaction (C—N bond formation) with a reagent $R_3$—H (XXXIIaa) equivalent to $HN(R_7)COR_8$, wherein $R_7$ and $R_8$ are as defined in formula I. Such a reaction is performed in the presence of a base, such as potassium carbonate, cesium carbonate, sodium hydroxide, in an inert solvent, such as toluene, dimethylformamide DMF, N-methyl pyrrolidone NMP, dimethyl sulfoxide DMSO, dioxane, tetrahydrofuran THF, and the like, optionally in the presence of a catalyst, for example palladium(II)acetate, bis(dibenzylideneacetone)palladium(0) (Pd $(dba)_2$) or tris(dibenzylidene-acetone)dipalladium(0) ($Pd_2(dba)_3$, optionally in form of a chloroform adduct), or a palladium pre-catalyst such as for example tert-BuBrettPhos Pd $G_3$ [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd $G_3$ [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

In the particular situation within scheme 10 when $R_3$ is —$N(R_7)_2$, wherein $R_7$ is as defined in formula I, then compounds of formula I-Qa, wherein X is SO or $SO_2$, may be prepared from compounds of formula XXXIIIa-1, wherein $R_1$, $R_2$, $G_1$, $G_2$ and $R_4$ are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $R_3$—H (XXXIIaa) equivalent to $HN(R_7)_2$, or a salt thereof (such as a hydrohalide salt, preferably a hydrochloride or a hydrobromide salt, or a trifluoroacetic acid salt, or any other equivalent salt), wherein $R_7$ is as defined in formula I. Such a reaction is commonly performed in an inert solvent such as alcohols, amides, esters, ethers, nitriles and water, particularly preferred are methanol, ethanol, 2,2,2-trifluoroethanol, propanol, isopropanol, N,N-dimethylformamide, N,N-dimethylacetamide, dioxane, tetrahydrofuran, dimethoxyethane, acetonitrile, ethyl acetate, toluene, water or mixtures thereof, at temperatures between 0-150° C., optionally under microwave irradiation or pressurized conditions using an autoclave, optionally in the presence of a copper catalyst, such as copper powder, copper(I) iodide or copper sulfate (optionally in form of a hydrate), or mixtures thereof, optionally in presence a ligand, for example diamine ligands (e.g. N,N'-dimethylethylenediamine or trans-cyclohexyldiamine) or dibenzylideneacetone (dba), or 1,10-phenanthroline, and optionally in presence of a base such as potassium phosphate.

Reagents $HN(R_7)_2$ or $HN(R_7)COR_8$, wherein $R_7$ and $R_8$ are as defined in formula I, are either known, commercially available or may be prepared by methods known to a person skilled in the art.

Alternatively, compounds of formula I-Qa, wherein X is SO or $SO_2$, may be prepared by a Suzuki reaction, which involves for example, reacting compounds of formula XXXIIIa-1, wherein $R_1$, $R_2$, $G_1$, $G_2$ and $R_4$ are as defined in formula I, and in which X is SO or $SO_2$, and wherein $X_b$ is a leaving group like, for example, chlorine, bromine or iodine (preferably chlorine or bromine), or an aryl- or alkylsulfonate such as trifluoromethanesulfonate, with compounds of formula (XXXII), wherein $R_3$ is as defined in formula I, and wherein $Y_{b1}$ can be a boron-derived functional group, such as for example $B(OH)_2$ or $B(OR_{b1})_2$ wherein $R_{b1}$ can be a $C_1$-$C_4$ alkyl group or the two groups $OR_{b1}$ can form together with the boron atom a five membered ring, as for example a pinacol boronic ester. The reaction may be catalyzed by a palladium based catalyst, for example tetrakis(triphenyl-phosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 576, 1999, 147-168.

When $R_3$ is a cyano group, then compounds of formula I-Qa, wherein X is SO or $SO_2$, may be prepared from compounds of formula XXXIIIa-1, wherein $R_1$, $R_2$, $G_1$, $G_2$ and $R_4$ are as defined in formula I, and in which X is SO or $SO_2$, and wherein $X_b$ is a leaving group like, for example, chlorine, bromine or iodine (preferably chlorine or bromine), or an aryl- or alkylsulfonate such as trifluoromethanesulfonate, by reaction with M-CN XXXIIa, wherein M is a metal coordinated to the cyanide. Examples of cyanating reagent include NaCN, $Zn(CN)_2$, potassium ferrocyanide amongst others. The reaction may be catalyzed by a palladium based catalyst, for example tetrakis(triphenyl-phosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such reactions are well known to those skilled in the art and are described for example in Org. Lett. 2011, 13:648-651, J. Org. Chem. 2017, 82:7040-7044.

Oxidation of compounds of formula XXXIa-1, wherein $R_1$, $R_2$, $G_1$, $G_2$ and $R_4$ are as defined in formula I, and in which X is S, and wherein $X_b$ is a leaving group like, for example, chlorine, bromine or iodine (preferably chlorine or bromine), or an aryl- or alkylsulfonate such as trifluoromethanesulfonate, with a suitable oxidizing agent, into compounds of formula XXXIIIa-1, wherein X is SO or $SO_2$ may be achieved under conditions already described above.

A large number of compounds of the formula (XXXII), (XXXIIa) and (XXXIIaa) are commercially available or can be prepared by those skilled in the art.

Alternatively, compounds of formula I-Qa, wherein X is SO or $SO_2$, may be prepared from compounds of formula XXXIa-1, wherein X is S (sulfide) by involving the same chemistry as described above, but by changing the order of the steps (i.e. by running the sequence XXXIa-1 (X is S) to I-Qa (X is S) via Suzuki, cyanation or C—N bond formation, followed by an oxidation step to form I-Qa (X is SO or $SO_2$).

The subgroup of compounds of formula I, wherein $G_1$, $G_2$ and $R_2$ are as defined in formula I above, and wherein Q is defined as Qa, in which $R_3$, $R_4$, X and $R_1$ are as defined in formula I, may be defined as compounds of formula I-Qa (scheme 11).

Scheme 11

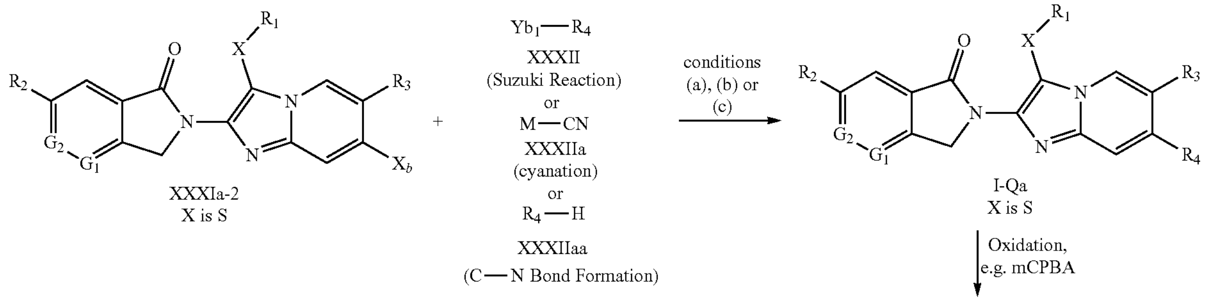

-continued

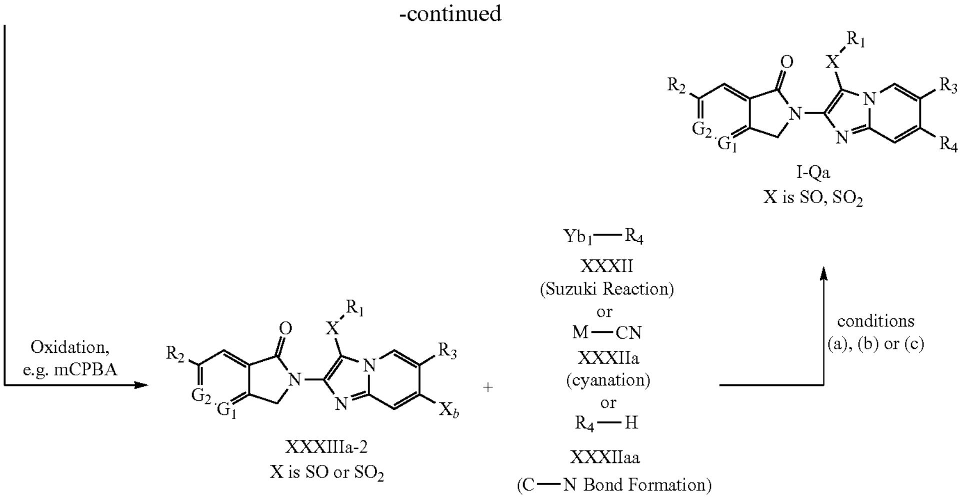

a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

b) Cyanation: cyanating reagent (e.g. NaCN, $Zn(CN)_2$, $K_4[Fe(CN)_6]$, Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

The chemistry described previously in scheme 10 to access compounds of formula I-Qa from compounds of formula XXXIa-1, can be applied analogously (scheme 11) for the preparation of compounds of formula I-Qa from compounds of formula XXXIa-2, wherein all substituent definitions mentioned previously remain valid.

The subgroup of compounds of formula I, wherein $G_1$, $G_2$ and $R_2$ are as defined in formula I above, and wherein Q is defined as Qb, in which $R_5$, $R_6$, X and $R_1$ are as defined in formula I, may be defined as compounds of formula I-Qb (scheme 12).

Scheme 12

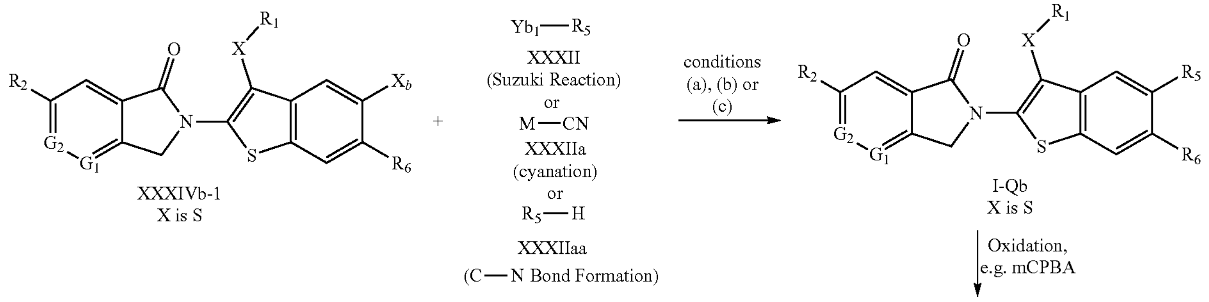

-continued

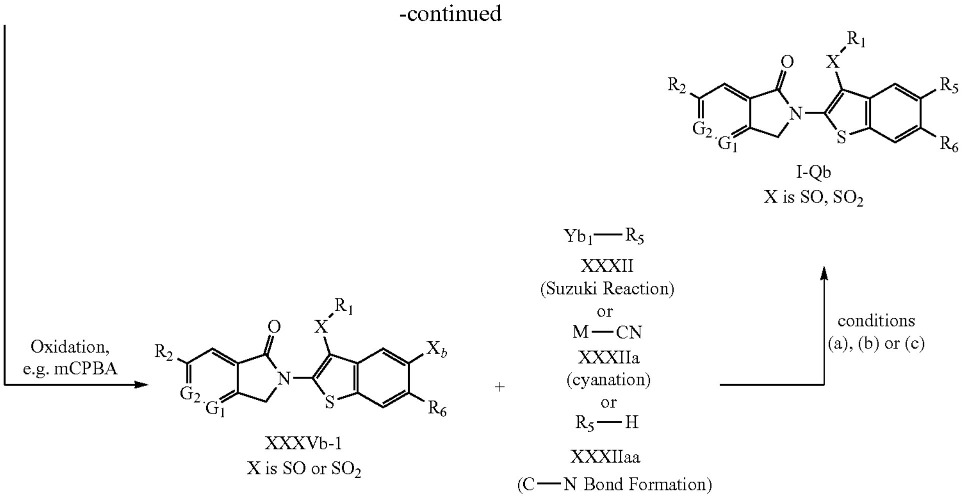

XXXVb-1
X is SO or $SO_2$

I-Qb
X is SO, $SO_2$ a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
b) Cyanation: cyanating reagent (e.g. NaCN, $Zn(CN)_2$, $K_4[Fe(CN)_6]$, Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

The chemistry described previously in scheme 10 to access compounds of formula I-Qa from compounds of formula XXXIa-1, can be applied analogously (scheme 12) for the preparation of compounds of formula I-Qb from compounds of formula XXXIVb-1, wherein all substituent definitions mentioned previously remain valid.

The subgroup of compounds of formula I, wherein $G_1$, $G_2$ and $R_2$ are as defined in formula I above, and wherein Q is defined as Qb, in which $R_5$, $R_6$, X and $R_1$ are as defined in formula I, may be defined as compounds of formula I-Qb (scheme 13).

Scheme 13

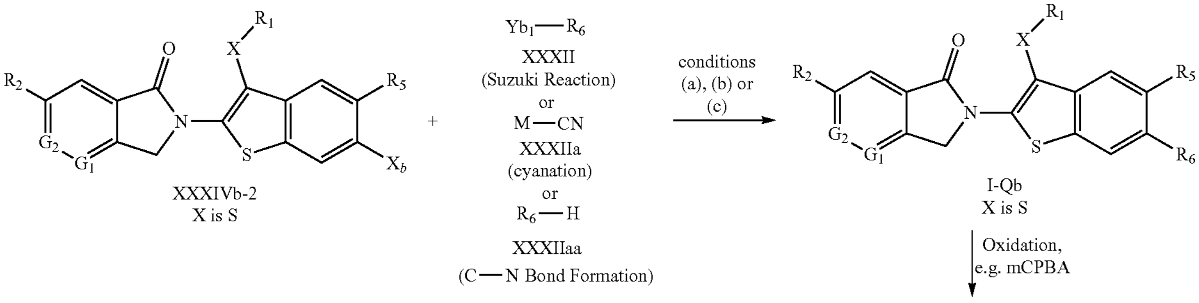

XXXIVb-2
X is S

I-Qb
X is S

-continued

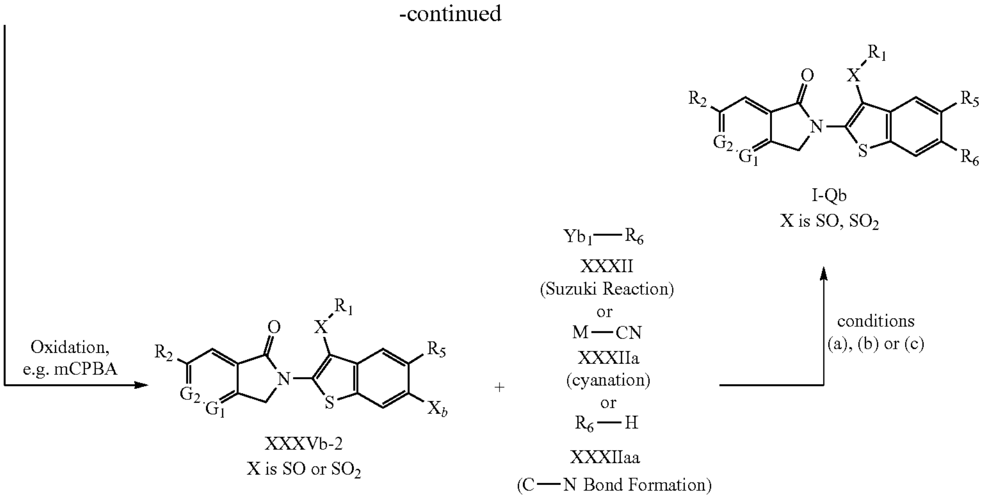

XXXVb-2
X is SO or $SO_2$

I-Qb
X is SO, $SO_2$ a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

b) Cyanation: cyanating reagent (e.g. NaCN, $Zn(CN)_2$, $K_4[Fe(CN)_6]$, Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

The chemistry described previously in scheme 11 to access compounds of formula I-Qa from compounds of formula XXXIa-2, can be applied analogously (scheme 13) for the preparation of compounds of formula I-Qb from compounds of formula XXXIVb-2, wherein all substituent definitions mentioned previously remain valid.

The subgroup of compounds of formula I, wherein $G_1$, $G_2$ and $R_2$ are as defined in formula I and wherein Q is defined as Qa, in which $R_4$, X and $R_1$ are as defined in formula I, and wherein $R_3$ is $C_1$-$C_4$ alkoxy or $C_1$-$C_6$ haloalkoxy, may be defined as compounds of formula I-Qa-O3, wherein Ry is $C_1$-$C_4$ alkyl or $C_1$-$C_6$ haloalkyl (scheme 14). Similarly, the subgroup of compounds of formula I, wherein $G_1$, $G_2$ and $R_2$ are as defined in formula I and wherein Q is defined as Qa, in which $R_4$, X and $R_1$ are as defined in formula I, and wherein $R_3$ is 1-cyano-1-methyl-ethoxy, may be defined as compounds of formula I-Qa-O5.

Scheme 14

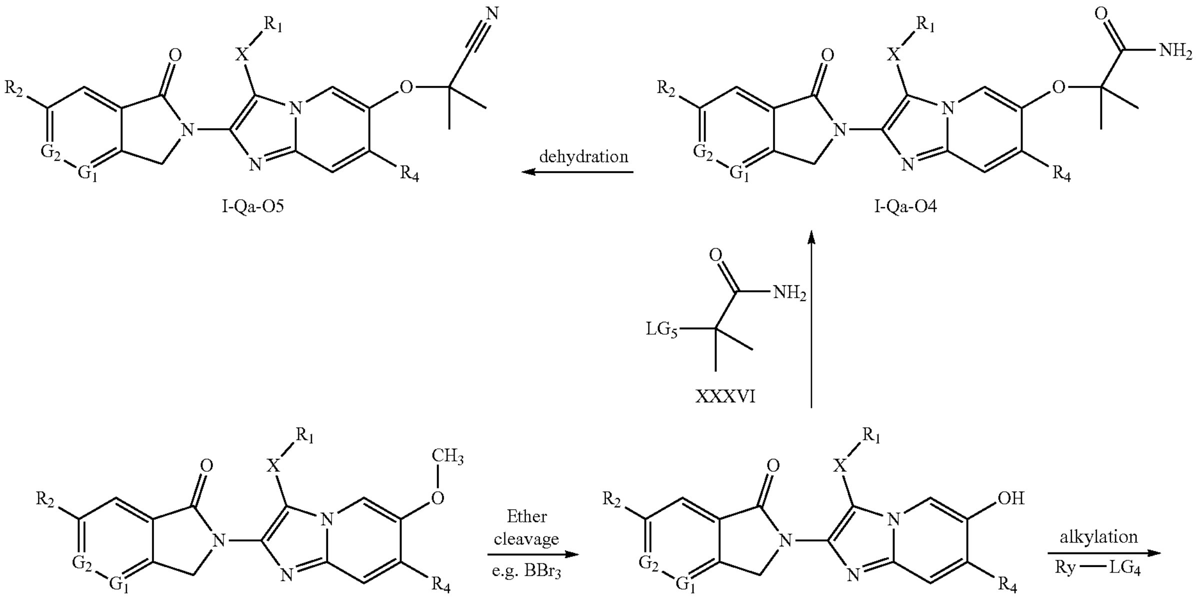

I-Qa-O5

I-Qa-O4

XXXVI

I-Qa-O1

I-Qa-O4

-continued

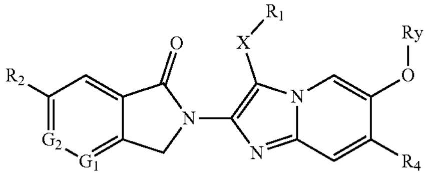

I-Qa-O3

Compounds of formula I-Qa-O3, wherein $R_4$, X, $R_1$, $G_1$, $G_2$ and $R_2$ are as defined in formula I, and in which Ry is $C_1$-$C_4$ alkyl or $C_1$-$C_6$ haloalkyl, can be prepared by reacting compounds of formula I-Qa-O2, wherein $R_4$, X, $R_1$, $G_1$, $G_2$ and $R_2$ are as defined in formula I, with alkylating reagents of formula Ry-$LG_4$, wherein Ry is $C_1$-$C_4$ alkyl or $C_1$-$C_5$ haloalkyl and $LG_4$ is a halogen, preferably iodine, bromine or chlorine (or a pseudo-halogen leaving group, such as a triflate), in the presence of a base such as sodium hydride, potassium carbonate, or cesium carbonate, in an inert solvent such as dioxane, tetrahydrofuran, N,N-dimethylformamide or acetonitrile, at temperatures between 0° C. and 120° C., preferably between 20° C. and 80° C., as described, for example, in WO18/197315. Known to a person skilled in the art, the alkylating reagent of formula Ry-$LG_4$ can be replaced by sodium 2-chloro-2,2-difluoroacetate (and the like) as difluoromethylating agent when performing a difluoromethylation to generate compounds of formula I-Qa-O3, wherein Ry is $CHF_2$.

Compounds of formula I-Qa-O2, wherein $R_4$, X, $R_1$, $G_1$, $G_2$ and $R_2$ are as defined in formula I, can be prepared by ether cleavage (O-demethylation) of compounds of formula I-Qa-O1, wherein $R_4$, X, $R_1$, $G_1$, $G_2$ and $R_2$ are as defined in formula I, in the presence of hydrogen bromide or hydrogen iodide in acetic acid, or concentrated hydrobromic or hydroiodic acid, or alternatively in the presence of a Lewis acid such as boron tribromide $BBr_3$, in an inert solvent such as pentane, hexane or dichloromethane, and at temperatures between −80° C. and 40° C., preferably between −20° C. and 30° C., as described, for example, in Organic Syntheses 49:13; Collective Volume, 5, p. 412.

Compounds of formula I-Qa-O1, wherein $R_4$, X, $R_1$, $G_1$, $G_2$ and $R_2$ are as defined in formula I, represent a subgroup of compounds of formula I, wherein $R_4$, X, $R_1$, $G_1$, $G_2$ and $R_2$ are as defined in formula I, and in which $R_3$ is —$OCH_3$. Such compounds of formula I-Qa-O1 can be prepared by methods already described herein above.

Reagents of formula Ry-$LG_4$, wherein Ry is $C_1$-$C_4$ alkyl or $C_1$-$C_6$ haloalkyl and $LG_4$ is a halogen, preferably iodine, bromine or chlorine (or a pseudo-halogen leaving group, such as a triflate), and surrogates thereof, such as sodium 2-chloro-2,2-difluoroacetate, are either known, commercially available or may be prepared by methods known to a person skilled in the art.

Compounds of formula I-Qa-O5, wherein $R_4$, X, $R_1$, $G_1$, $G_2$ and $R_2$ are as defined in formula I, can be prepared (scheme 14) under dehydration conditions by reacting compounds of formula I-Qa-O4, wherein $R_4$, X, $R_1$, $G_1$, $G_2$ and $R_2$ are as defined in formula I, with a dehydrating agent such as trifluoroacetic acid, trifluoroacetic anhydride, phosphorus pentoxide, thionyl chloride or phosphorus oxychloride, optionally in presence of a base such as triethylamine or pyridine, in an appropriate solvent such as for example dichloromethane, tetrahydrofuran, dioxane or N,N-dimethylformamide, at temperatures between 0° C. and 180° C., preferably between 5° C. and 80° C., as described, for example, in WO20/084075.

Compounds of formula I-Qa-O4, wherein $R_4$, X, $R_1$, $G_1$, $G_2$ and $R_2$ are as defined in formula I, can be prepared by reacting compounds of formula I-Qa-O2, wherein $R_4$, X, $R_1$, $G_1$, $G_2$ and $R_2$ are as defined in formula I, with reagents of formula XXXVI, wherein $LG_5$ is a halogen leaving group, such as iodine, bromine or chlorine (preferably bromine), in the presence of a base such as, for example, lithium, sodium or potassium hydroxide, sodium hydride, potassium or cesium carbonate, in a suitable solvent such as acetone, dioxane, acetonitrile, N,N-dimethylformamide or N,N-dimethylacetamide, at temperatures between −10° C. and 100° C., preferably between 0° C. and 80° C., as described, for example, in WO20/084075.

Reagents of formula XXXVI, wherein $LG_5$ is a halogen leaving group, such as iodine, bromine or chlorine (preferably bromine), are either known, commercially available or may be prepared by methods known to a person skilled in the art.

Similar considerations as shown in scheme 14 can be applied when interverting the substituents at positions $R_3$ and $R_4$ to access isomeric compounds of formula I-Qa-O6 and I-Qa-07, I-Qa-O6

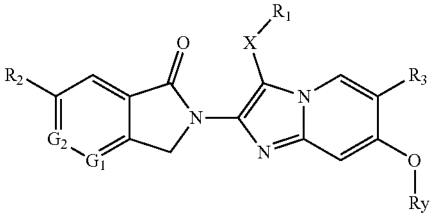

I-Qa-O7

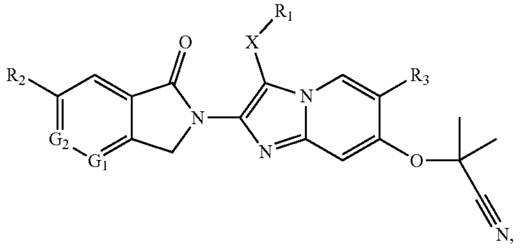

wherein all substituent definitions mentioned previously remain valid.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention, and by post modification of compounds of with reactions such as oxidation, alkylation, reduction, acylation and other methods known by those skilled in the art.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables A-1 to A-12, B-1 to B-12, C-1 to C-18, D-1 to D-18, E-1 to E-12, F-1 to F-12, G-1 to G-18, and H-1 to H-18 below can be prepared according to the methods described above. The examples which follow are intended to illustrate the invention and show preferred compounds of formula I.

The tables A-1 to A-12 below illustrate specific compound of the invention.

(Ia-Qa)

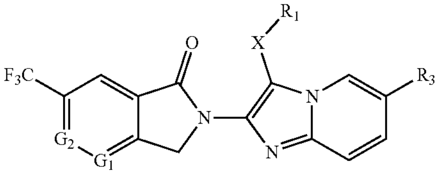

Table A-1 provides 17 compounds A-1.001 to A-1.017 of formula Ia-Qa wherein $G_1$ is N, $G_2$ is N, $R_1$ is ethyl, X is S and $R_3$ is as defined in table Y.

TABLE Y

| Substituent definitions of $R_3$: | |
|---|---|
| Index | $R_3$ |
| 1 | H |
| 2 | Me |
| 3 | $CF_3$ |
| 4 | CN |
| 5 | $—N(CH_3)COCH_3$ |
| 6 | $—NHCOCH_3$ |
| 7 | —OMe |
| 8 | $—OCH_2CF_3$ |
| 9 | —O—iPr |
| 10 | 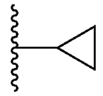 |
| 11 | 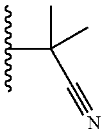 [SMILES: *C(C)(C)C#N] |
| 12 | 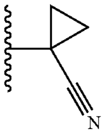 [SMILES: *C1(C#N)CC1] |
| 13 | Br |
| 14 | $—OCHF_2$ |
| 15 | $—OCH_2CHF_2$ |
| 16 | $CF_2CH_3$ |
| 17 | 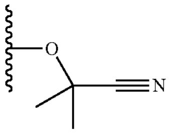 [SMILES: *OC(C)(C)C#N] |

Table A-2 provides 17 compounds A-2.001 to A-2.017 of formula Ia-Qa wherein $G_1$ is N, $G_2$ is N, $R_1$ is ethyl, X is SO and $R_3$ is as defined in table Y.

Table A-3 provides 17 compounds A-3.001 to A-3.017 of formula Ia-Qa wherein $G_1$ is N, $G_2$ is N, $R_1$ is ethyl, X is $SO_2$ and $R_3$ is as defined in table Y.

Table A-4 provides 17 compounds A-4.001 to A-4.017 of formula Ia-Qa wherein $G_1$ is N, $G_2$ is CH, $R_1$ is ethyl, X is S and $R_3$ is as defined in table Y.

Table A-5 provides 17 compounds A-5.001 to A-5.017 of formula Ia-Qa wherein $G_1$ is N, $G_2$ is CH, $R_1$ is ethyl, X is SO and $R_3$ is as defined in table Y.

Table A-6 provides 17 compounds A-6.001 to A-6.017 of formula Ia-Qa wherein $G_1$ is N, $G_2$ is CH, $R_1$ is ethyl, X is $SO_2$ and $R_3$ is as defined in table Y.

Table A-7 provides 17 compounds A-7.001 to A-7.017 of formula Ia-Qa wherein $G_1$ is CH, $G_2$ is N, $R_1$ is ethyl, X is S and $R_3$ is as defined in table Y.

Table A-8 provides 17 compounds A-8.001 to A-8.017 of formula Ia-Qa wherein $G_1$ is CH, $G_2$ is N, $R_1$ is ethyl, X is SO and $R_3$ is as defined in table Y.

Table A-9 provides 17 compounds A-9.001 to A-9.017 of formula Ia-Qa wherein $G_1$ is CH, $G_2$ is N, $R_1$ is ethyl, X is $SO_2$ and $R_3$ is as defined in table Y.

Table A-10 provides 17 compounds A-10.001 to A-10.017 of formula Ia-Qa wherein $G_1$ is CH, $G_2$ is CH, $R_1$ is ethyl, X is S and $R_3$ is as defined in table Y.

Table A-11 provides 17 compounds A-11.001 to A-11.017 of formula Ia-Qa wherein $G_1$ is CH, $G_2$ is CH, $R_1$ is ethyl, X is SO and $R_3$ is as defined in table Y.

Table A-12 provides 17 compounds A-12.001 to A-12.017 of formula Ia-Qa wherein $G_1$ is CH, $G_2$ is CH, $R_1$ is ethyl, X is $SO_2$ and $R_3$ is as defined in table Y.

The tables B-1 to B-12 below illustrate further specific compound of the invention.

(Ib-Qa)

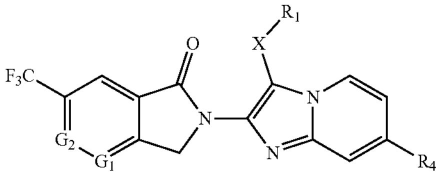

Table B-1 provides 17 compounds B-1.001 to B-1.017 of formula Ib-Qa wherein $G_1$ is N, $G_2$ is N, $R_1$ is ethyl, X is S and $R_4$ is as defined in table Z.

TABLE Z

| Substituent definitions of $R_4$: | |
|---|---|
| Index | $R_4$ |
| 1 | H |
| 2 | Me |
| 3 | $CF_3$ |
| 4 | CN |
| 5 | $—N(CH_3)COCH_3$ |
| 6 | $—NHCOCH_3$ |
| 7 | —OMe |
| 8 | $—OCH_2CF_3$ |
| 9 | —O—iPr |
| 10 | 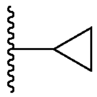 |

TABLE Z-continued

| Substituent definitions of $R_4$: | |
|---|---|
| Index | $R_4$ |
| 11 | 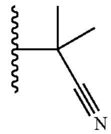 [SMILES: *C(C)(C)C#N] |
| 12 | 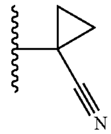 [SMILES: *C1(C#N)CC1] |
| 13 | Br |
| 14 | $—OCHF_2$ |
| 15 | $—OCH_2CHF_2$ |
| 16 | $CF_2CH_3$ |
| 17 | 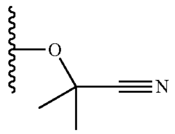 [SMILES: *OC(C)(C)C#N] |

Table B-2 provides 17 compounds B-2.001 to B-2.017 of formula Ib-Qa wherein $G_1$ is N, $G_2$ is N, $R_1$ is ethyl, X is SO and $R_4$ is as defined in table Z.

Table B-3 provides 17 compounds B-3.001 to B-3.017 of formula Ib-Qa wherein $G_1$ is N, $G_2$ is N, $R_1$ is ethyl, X is $SO_2$ and $R_4$ is as defined in table Z.

Table B-4 provides 17 compounds B-4.001 to B-4.017 of formula Ib-Qa wherein $G_1$ is N, $G_2$ is CH, $R_1$ is ethyl, X is S and $R_4$ is as defined in table Z.

Table B-5 provides 17 compounds B-5.001 to B-5.017 of formula Ib-Qa wherein $G_1$ is N, $G_2$ is CH, $R_1$ is ethyl, X is SO and $R_4$ is as defined in table Z.

Table B-6 provides 17 compounds B-6.001 to B-6.017 of formula Ib-Qa wherein $G_1$ is N, $G_2$ is CH, $R_1$ is ethyl, X is $SO_2$ and $R_4$ is as defined in table Z.

Table B-7 provides 17 compounds B-7.001 to B-7.017 of formula Ib-Qa wherein $G_1$ is CH, $G_2$ is N, $R_1$ is ethyl, X is S and $R_4$ is as defined in table Z.

Table B-8 provides 17 compounds B-8.001 to B-8.017 of formula Ib-Qa wherein $G_1$ is CH, $G_2$ is N, $R_1$ is ethyl, X is SO and $R_4$ is as defined in table Z.

Table B-9 provides 17 compounds B-9.001 to B-9.017 of formula Ib-Qa wherein $G_1$ is CH, $G_2$ is N, $R_1$ is ethyl, X is $SO_2$ and $R_4$ is as defined in table Z.

Table B-10 provides 17 compounds B-10.001 to B-10.017 of formula Ia-Qa wherein $G_1$ is CH, $G_2$ is CH, $R_1$ is ethyl, X is S and $R_4$ is as defined in table Z.

Table B-11 provides 17 compounds B-11.001 to B-11.017 of formula Ib-Qa wherein $G_1$ is CH, $G_2$ is CH, $R_1$ is ethyl, X is SO and $R_4$ is as defined in table Z.

Table B-12 provides 17 compounds B-12.001 to B-12.017 of formula Ib-Qa wherein $G_1$ is CH, $G_2$ is CH, $R_1$ is ethyl, X is $SO_2$ and $R_4$ is as defined in table Z.

The tables C-1 to C-18 below illustrate further specific compound of the invention.

(Ic-Qa)

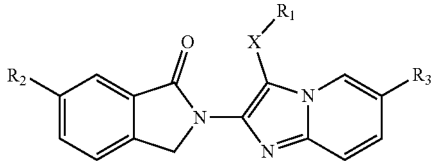

Table C-1 provides 17 compounds C-1.001 to C-1.017 of formula Ic-Qa wherein $R_2$ is $SCF_3$, $R_1$ is ethyl, X is S and $R_3$ is as defined in table Y.

Table C-2 provides 17 compounds C-2.001 to C-2.017 of formula Ic-Qa wherein $R_2$ is $SCF_3$, $R_1$ is ethyl, X is SO and $R_3$ is as defined in table Y.

Table C-3 provides 17 compounds C-3.001 to C-3.017 of formula Ic-Qa wherein $R_2$ is $SCF_3$, $R_1$ is ethyl, X is $SO_2$ and $R_3$ is as defined in table Y.

Table C-4 provides 17 compounds C-4.001 to C-4.017 of formula Ic-Qa wherein $R_2$ is $SOCF_3$, $R_1$ is ethyl, X is S and $R_3$ is as defined in table Y.

Table C-5 provides 17 compounds C-5.001 to C-5.017 of formula Ic-Qa wherein $R_2$ is $SOCF_3$, $R_1$ is ethyl, X is SO and $R_3$ is as defined in table Y.

Table C-6 provides 17 compounds C-6.001 to C-6.017 of formula Ic-Qa wherein $R_2$ is $SOCF_3$, $R_1$ is ethyl, X is $SO_2$ and $R_3$ is as defined in table Y.

Table C-7 provides 17 compounds C-7.001 to C-7.017 of formula Ic-Qa wherein $R_2$ is $SO_2CF_3$, $R_1$ is ethyl, X is S and $R_3$ is as defined in table Y.

Table C-8 provides 17 compounds C-8.001 to C-8.017 of formula Ic-Qa wherein $R_2$ is $SO_2CF_3$, $R_1$ is ethyl, X is SO and $R_3$ is as defined in table Y.

Table C-9 provides 17 compounds C-9.001 to C-9.017 of formula Ic-Qa wherein $R_2$ is $SO_2CF_3$, $R_1$ is ethyl, X is $SO_2$ and $R_3$ is as defined in table Y.

Table C-10 provides 17 compounds C-10.001 to C-10.017 of formula Ic-Qa wherein $R_2$ is $OSO_2CF_3$, $R_1$ is ethyl, X is S and $R_3$ is as defined in table Y.

Table C-11 provides 17 compounds C-11.001 to C-11.017 of formula Ic-Qa wherein $R_2$ is $OSO_2CF_3$, $R_1$ is ethyl, X is SO and $R_3$ is as defined in table Y.

Table C-12 provides 17 compounds C-12.001 to C-12.017 of formula Ic-Qa wherein $R_2$ is $OSO_2CF_3$, $R_1$ is ethyl, X is $SO_2$ and $R_3$ is as defined in table Y.

Table C-13 provides 17 compounds C-13.001 to C-13.017 of formula Ic-Qa wherein $R_2$ is $OCF_3$, $R_1$ is ethyl, X is S and $R_3$ is as defined in table Y.

Table C-14 provides 17 compounds C-14.001 to C-14.017 of formula Ic-Qa wherein $R_2$ is $OCF_3$, $R_1$ is ethyl, X is SO and $R_3$ is as defined in table Y.

Table C-15 provides 17 compounds C-15.001 to C-15.017 of formula Ic-Qa wherein $R_2$ is $OCF_3$, $R_1$ is ethyl, X is $SO_2$ and $R_3$ is as defined in table Y.

Table C-16 provides 17 compounds C-16.001 to C-16.017 of formula Ic-Qa wherein $R_2$ is $OCHF_2$, $R_1$ is ethyl, X is S and $R_3$ is as defined in table Y.

Table C-17 provides 17 compounds C-17.001 to C-17.017 of formula Ic-Qa wherein $R_2$ is $OCHF_2$, $R_1$ is ethyl, X is SO and $R_3$ is as defined in table Y.

Table C-18 provides 17 compounds C-18.001 to C-18.017 of formula Ic-Qa wherein $R_2$ is $OCHF_2$, $R_1$ is ethyl, X is $SO_2$ and $R_3$ is as defined in table Y.

The tables D-1 to D-18 below illustrate further specific compound of the invention.

(Id-Qa)

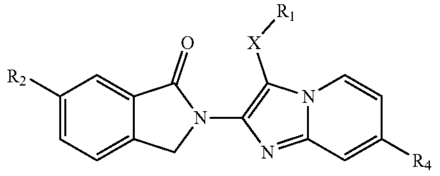

Table D-1 provides 17 compounds D-1.001 to D-1.017 of formula Id-Qa wherein $R_1$ is ethyl, X is S, $R_2$ is $SCF_3$ and $R_4$ is as defined in table Z.

Table D-2 provides 17 compounds D-2.001 to D-2.017 of formula Id-Qa wherein $R_1$ is ethyl, X is S, $R_2$ is $SOCF_3$ and $R_4$ is as defined in table Z.

Table D-3 provides 17 compounds D-3.001 to D-3.017 of formula Id-Qa wherein $R_1$ is ethyl, X is S, $R_2$ is $SO_2CF_3$ and $R_4$ is as defined in table Z.

Table D-4 provides 17 compounds D-4.001 to D-4.017 of formula Id-Qa wherein $R_1$ is ethyl, X is S, $R_2$ is $OSO_2CF_3$ and $R_4$ is as defined in table Z.

Table D-5 provides 17 compounds D-5.001 to D-5.017 of formula Id-Qa wherein $R_1$ is ethyl, X is S, $R_2$ is $OCF_3$ and $R_4$ is as defined in table Z.

Table D-6 provides 17 compounds D-6.001 to D-6.017 of formula Id-Qa wherein $R_1$ is ethyl, X is SO, $R_2$ is $SCF_3$ and $R_4$ is as defined in table Z.

Table D-7 provides 17 compounds D-7.001 to D-7.017 of formula Id-Qa wherein $R_1$ is ethyl, X is SO, $R_2$ is $SOCF_3$ and $R_4$ is as defined in table Z.

Table D-8 provides 17 compounds D-8.001 to D-8.017 of formula Id-Qa wherein $R_1$ is ethyl, X is SO, $R_2$ is $SO_2CF_3$ and $R_4$ is as defined in table Z.

Table D-9 provides 17 compounds D-9.001 to D-9.017 of formula Id-Qa wherein $R_1$ is ethyl, X is SO, $R_2$ is $OSO_2CF_3$ and $R_4$ is as defined in table Z.

Table D-10 provides 17 compounds D-10.001 to D-10.017 of formula Id-Qa wherein $R_1$ is ethyl, X is SO, $R_2$ is $OCF_3$ and $R_4$ is as defined in table Z.

Table D-11 provides 17 compounds D-11.001 to D-11.017 of formula Id-Qa wherein $R_1$ is ethyl, X is $SO_2$, $R_2$ is $SCF_3$ and $R_4$ is as defined in table Z.

Table D-12 provides 17 compounds D-12.001 to D-12.017 of formula Id-Qa wherein $R_1$ is ethyl, X is $SO_2$, $R_2$ is $SOCF_3$ and $R_4$ is as defined in table Z.

Table D-13 provides 17 compounds D-13.001 to D-13.017 of formula Id-Qa wherein $R_1$ is ethyl, X is $SO_2$, $R_2$ is $SO_2CF_3$ and $R_4$ is as defined in table Z.

Table D-14 provides 17 compounds D-14.001 to D-14.017 of formula Id-Qa wherein $R_1$ is ethyl, X is $SO_2$, $R_2$ is $OSO_2CF_3$ and $R_4$ is as defined in table Z.

Table D-15 provides 17 compounds D-15.001 to D-15.017 of formula Id-Qa wherein $R_1$ is ethyl, X is $SO_2$, $R_2$ is $OCF_3$ and $R_4$ is as defined in table Z.

Table D-16 provides 17 compounds D-16.001 to D-16.017 of formula Id-Qa wherein $R_1$ is ethyl, X is S, $R_2$ is $OCHF_2$ and $R_4$ is as defined in table Z.

Table D-17 provides 17 compounds D-17.001 to D-17.017 of formula Id-Qa wherein $R_1$ is ethyl, X is SO, $R_2$ is $OCHF_2$ and $R_4$ is as defined in table Z.

Table D-18 provides 17 compounds D-18.001 to D-18.017 of formula Id-Qa wherein $R_1$ is ethyl, X is $SO_2$, $R_2$ is $OCHF_2$ and $R_4$ is as defined in table Z.

The tables E-1 to E-12 below illustrate further specific compound of the invention.

(Ia-Qb)

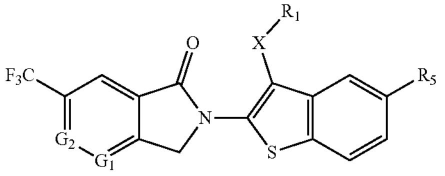

Table E-1 provides 17 compounds E-1.001 to E-1.017 of formula Ia-Qb wherein X is S, $R_1$ is ethyl, $G_1$ is N, $G_2$ is N and $R_5$ is as defined in table V.

TABLE V

Substituent definitions of $R_5$:

| Index | $R_5$ |
|---|---|
| 1 | H |
| 2 | Me |
| 3 | $CF_3$ |
| 4 | CN |
| 5 | $—N(CH_3)COCH_3$ |
| 6 | $—NHCOCH_3$ |
| 7 | —OMe |
| 8 | $—OCH_2CF_3$ |
| 9 | —O—iPr |
| 10 | 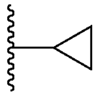 |
| 11 | 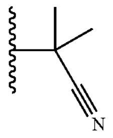 |
| 12 | 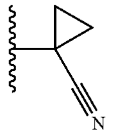 [SMILES: *C1(C#N)CC1] |
| 13 | Br |
| 14 | $—OCHF_2$ |
| 15 | $—OCH_2CHF_2$ |
| 16 | $CF_2CH_3$ |
| 17 | 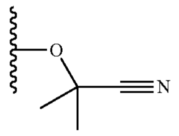 [SMILES: *OC(C)(C)C#N] |

Table E-2 provides 17 compounds E-2.001 to E-2.017 of formula Ia-Qb wherein X is S, $R_1$ is ethyl, $G_1$ is N, $G_2$ is CH and $R_5$ is as defined in table V.

Table E-3 provides 17 compounds E-3.001 to E-3.017 of formula Ia-Qb wherein X is S, $R_1$ is ethyl, $G_1$ is CH, $G_2$ is N and $R_5$ is as defined in table V.

Table E-4 provides 17 compounds E-4.001 to E-4.017 of formula Ia-Qb wherein X is S, $R_1$ is ethyl, $G_1$ is CH, $G_2$ is CH and $R_5$ is as defined in table V.

Table E-5 provides 17 compounds E-5.001 to E-5.017 of formula Ia-Qb wherein X is SO, $R_1$ is ethyl, $G_1$ is N, $G_2$ is N and $R_5$ is as defined in table V.

Table E-6 provides 17 compounds E-6.001 to E-6.017 of formula Ia-Qb wherein X is SO, $R_1$ is ethyl, $G_1$ is N, $G_2$ is CH and $R_5$ is as defined in table V.

Table E-7 provides 17 compounds E-7.001 to E-7.017 of formula Ia-Qb wherein X is SO, $R_1$ is ethyl, $G_1$ is CH, $G_2$ is N and $R_5$ is as defined in table V.

Table E-8 provides 17 compounds E-8.001 to E-8.017 of formula Ia-Qb wherein X is SO, $R_1$ is ethyl, $G_1$ is CH, $G_2$ is CH and $R_5$ is as defined in table V.

Table E-9 provides 17 compounds E-9.001 to E-9.017 of formula Ia-Qb wherein X is $SO_2$, $R_1$ is ethyl, $G_1$ is N, $G_2$ is N and $R_5$ is as defined in table V.

Table E-10 provides 17 compounds E-10.001 to E-10.017 of formula Ia-Qb wherein X is $SO_2$, $R_1$ is ethyl, $G_1$ is N, $G_2$ is CH and $R_5$ is as defined in table V.

Table E-11 provides 17 compounds E-11.001 to E-11.017 of formula Ia-Qb wherein X is $SO_2$, $R_1$ is ethyl, $G_1$ is CH, $G_2$ is N and $R_5$ is as defined in table V.

Table E-12 provides 17 compounds E-12.001 to E-12.017 of formula Ia-Qb wherein X is $SO_2$, $R_1$ is ethyl, $G_1$ is CH, $G_2$ is CH and $R_5$ is as defined in table V.

The tables F-1 to F-12 below illustrate further specific compound of the invention.

(Ib-Qb)

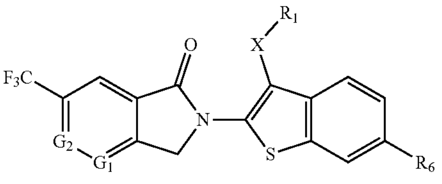

Table F-1 provides 17 compounds F-1.001 to F-1.017 of formula Ib-Qb wherein X is S, $R_1$ is ethyl, $G_1$ is N, $G_2$ is N and $R_6$ is as defined in table W.

TABLE W

| Substituent definitions of $R_6$: | |
|---|---|
| Index | $R_6$ |
| 1 | H |
| 2 | Me |
| 3 | $CF_3$ |
| 4 | CN |
| 5 | $—N(CH_3)COCH_3$ |
| 6 | $—NHCOCH_3$ |
| 7 | —OMe |
| 8 | $—OCH_2CF_3$ |
| 9 | —O—iPr |
| 10 | 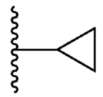 |
| 11 | 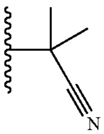 [SMILES: *C(C)(C)C#N] |
| 12 | 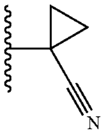 [SMILES: *C1(C#N)CC1] |
| 13 | Br |
| 14 | $—OCHF_2$ |
| 15 | $—OCH_2CHF_2$ |

TABLE W-continued

| Substituent definitions of $R_6$: | |
|---|---|
| Index | $R_6$ |
| 16 | $CF_2CH_3$ |
| 17 | 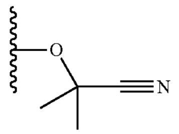 [SMILES: *OC(C)(C)C#N] |

Table F-2 provides 17 compounds F-2.001 to F-2.017 of formula Ib-Qb wherein X is S, $R_1$ is ethyl, $G_1$ is N, $G_2$ is CH and $R_6$ is as defined in table W.

Table F-3 provides 17 compounds F-3.001 to F-3.017 of formula Ib-Qb wherein X is S, $R_1$ is ethyl, $G_1$ is CH, $G_2$ is N and $R_6$ is as defined in table W.

Table F-4 provides 17 compounds F-4.001 to F-4.017 of formula Ib-Qb wherein X is S, $R_1$ is ethyl, $G_1$ is CH, $G_2$ is CH and $R_6$ is as defined in table W.

Table F-5 provides 17 compounds F-5.001 to F-5.017 of formula Ib-Qb wherein X is SO, $R_1$ is ethyl, $G_1$ is N, $G_2$ is N and $R_6$ is as defined in table W.

Table F-6 provides 17 compounds F-6.001 to F-6.017 of formula Ib-Qb wherein X is SO, $R_1$ is ethyl, $G_1$ is N, $G_2$ is CH and $R_6$ is as defined in table W.

Table F-7 provides 17 compounds F-7.001 to F-7.017 of formula Ib-Qb wherein X is SO, $R_1$ is ethyl, $G_1$ is CH, $G_2$ is N and $R_6$ is as defined in table W.

Table F-8 provides 17 compounds F-8.001 to F-8.017 of formula Ib-Qb wherein X is SO, $R_1$ is ethyl, $G_1$ is CH, $G_2$ is CH and $R_6$ is as defined in table W.

Table F-9 provides 17 compounds F-9.001 to F-9.017 of formula Ib-Qb wherein X is $SO_2$, $R_1$ is ethyl, $G_1$ is N, $G_2$ is N and $R_6$ is as defined in table W.

Table F-10 provides 17 compounds F-10.001 to F-10.017 of formula Ib-Qb wherein X is $SO_2$, $R_1$ is ethyl, $G_1$ is N, $G_2$ is CH and $R_6$ is as defined in table W.

Table F-11 provides 17 compounds F-11.001 to F-11.017 of formula Ib-Qb wherein X is $SO_2$, $R_1$ is ethyl, $G_1$ is CH, $G_2$ is N and $R_6$ is as defined in table W.

Table F-12 provides 17 compounds F-12.001 to F-12.017 of formula Ib-Qb wherein X is $SO_2$, $R_1$ is ethyl, $G_1$ is CH, $G_2$ is CH and $R_6$ is as defined in table W.

The tables G-1 to G-18 below illustrate further specific compound of the invention.

(Ic-Qb)

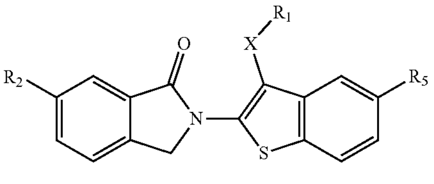

Table G-1 provides 17 compounds G-1.001 to G-1.017 of formula Ic-Qb wherein X is S, $R_1$ is ethyl, $R_2$ is $SCF_3$ and $R_5$ is as defined in table V.

Table G-2 provides 17 compounds G-2.001 to G-2.017 of formula Ic-Qb wherein X is S, $R_1$ is ethyl, $R_2$ is $SOCF_3$ and $R_5$ is as defined in table V.

Table G-3 provides 17 compounds G-3.001 to G-3.017 of formula Ic-Qb wherein X is S, $R_1$ is ethyl, $R_2$ is $SO_2CF_3$ and $R_5$ is as defined in table V.

Table G-4 provides 17 compounds G-4.001 to G-4.017 of formula Ic-Qb wherein X is S, $R_1$ is ethyl, $R_2$ is $OSO_2CF_3$ and $R_5$ is as defined in table V.

Table G-5 provides 17 compounds G-5.001 to G-5.017 of formula Ic-Qb wherein X is S, $R_1$ is ethyl, $R_2$ is $OCF_3$ and $R_5$ is as defined in table V.

Table G-6 provides 17 compounds G-6.001 to G-6.017 of formula Ic-Qb wherein X is SO, $R_1$ is ethyl, $R_2$ is $SCF_3$ and $R_5$ is as defined in table V.

Table G-7 provides 17 compounds G-7.001 to G-7.017 of formula Ic-Qb wherein X is SO, $R_1$ is ethyl, $R_2$ is $SOCF_3$ and $R_5$ is as defined in table V.

Table G-8 provides 17 compounds G-8.001 to G-8.017 of formula Ic-Qb wherein X is SO, $R_1$ is ethyl, $R_2$ is $SO_2CF_3$ and $R_5$ is as defined in table V.

Table G-9 provides 17 compounds G-9.001 to G-9.017 of formula Ic-Qb wherein X is SO, $R_1$ is ethyl, $R_2$ is $OSO_2CF_3$ and $R_5$ is as defined in table V.

Table G-10 provides 17 compounds G-10.001 to G-10.017 of formula Ic-Qb wherein X is SO, $R_1$ is ethyl, $R_2$ is $OCF_3$ and $R_5$ is as defined in table V.

Table G-11 provides 17 compounds G-11.001 to G-11.017 of formula Ic-Qb wherein X is $SO_2$, $R_1$ is ethyl, $R_2$ is $SCF_3$ and $R_5$ is as defined in table V.

Table G-12 provides 17 compounds G-12.001 to G-12.017 of formula Ic-Qb wherein X is $SO_2$, $R_1$ is ethyl, $R_2$ is $SOCF_3$ and $R_5$ is as defined in table V.

Table G-13 provides 17 compounds G-13.001 to G-13.017 of formula Ic-Qb wherein X is $SO_2$, $R_1$ is ethyl, $R_2$ is $SO_2CF_3$ and $R_5$ is as defined in table V.

Table G-14 provides 17 compounds G-14.001 to G-14.017 of formula Ic-Qb wherein X is $SO_2$, $R_1$ is ethyl, $R_2$ is $OSO_2CF_3$ and $R_5$ is as defined in table V.

Table G-15 provides 17 compounds G-15.001 to G-15.017 of formula Ic-Qb wherein X is $SO_2$, $R_1$ is ethyl, $R_2$ is $OCF_3$ and $R_5$ is as defined in table V.

Table G-16 provides 17 compounds G-16.001 to G-16.017 of formula Ic-Qb wherein $R_2$ is $OCHF_2$, $R_1$ is ethyl, X is S and $R_5$ is as defined in table V.

Table G-17 provides 17 compounds G-17.001 to G-17.017 of formula Ic-Qb wherein $R_2$ is $OCHF_2$, $R_1$ is ethyl, X is SO and $R_5$ is as defined in table V.

Table G-18 provides 17 compounds G-18.001 to G-18.017 of formula Ic-Qb wherein $R_2$ is $OCHF_2$, $R_1$ is ethyl, X is $SO_2$ and $R_5$ is as defined in table V.

The tables H-1 to H-18 below illustrate further specific compound of the invention.

(Id-Qb)

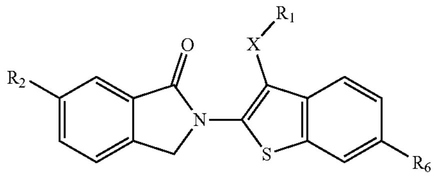

Table H-1 provides 17 compounds H-1.001 to H-1.017 of formula Id-Qb wherein X is S, $R_1$ is ethyl, $R_2$ is $SCF_3$ and $R_6$ is as defined in table W.

Table H-2 provides 17 compounds H-2.001 to H-2.017 of formula Id-Qb wherein X is S, $R_1$ is ethyl, $R_2$ is $SOCF_3$ and $R_6$ is as defined in table W.

Table H-3 provides 17 compounds H-3.001 to H-3.017 of formula Id-Qb wherein X is S, $R_1$ is ethyl, $R_2$ is $SO_2CF_3$ and $R_6$ is as defined in table W.

Table H-4 provides 17 compounds H-4.001 to H-4.017 of formula Id-Qb wherein X is S, $R_1$ is ethyl, $R_2$ is $OSO_2CF_3$ and $R_6$ is as defined in table W.

Table H-5 provides 17 compounds H-5.001 to H-5.017 of formula Id-Qb wherein X is S, $R_1$ is ethyl, $R_2$ is $OCF_3$ and $R_6$ is as defined in table W.

Table H-6 provides 17 compounds H-6.001 to H-6.017 of formula Id-Qb wherein X is SO, $R_1$ is ethyl, $R_2$ is $SCF_3$ and $R_6$ is as defined in table W.

Table H-7 provides 17 compounds H-7.001 to H-7.017 of formula Id-Qb wherein X is SO, $R_1$ is ethyl, $R_2$ is $SOCF_3$ and $R_6$ is as defined in table W.

Table H-8 provides 17 compounds H-8.001 to H-8.017 of formula Id-Qb wherein X is SO, $R_1$ is ethyl, $R_2$ is $SO_2CF_3$ and $R_6$ is as defined in table W.

Table H-9 provides 17 compounds H-9.001 to H-9.017 of formula Id-Qb wherein X is SO, $R_1$ is ethyl, $R_2$ is $OSO_2CF_3$ and $R_6$ is as defined in table W.

Table H-10 provides 17 compounds H-10.001 to H-10.017 of formula Id-Qb wherein X is SO, $R_1$ is ethyl, $R_2$ is $OCF_3$ and $R_6$ is as defined in table W.

Table H-11 provides 17 compounds H-11.001 to H-11.017 of formula Id-Qb wherein X is $SO_2$, $R_1$ is ethyl, $R_2$ is $SCF_3$ and RB is as defined in table W.

Table H-12 provides 17 compounds H-12.001 to H-12.017 of formula Id-Qb wherein X is $SO_2$, $R_1$ is ethyl, $R_2$ is $SOCF_3$ and $R_6$ is as defined in table W.

Table H-13 provides 17 compounds H-13.001 to H-13.017 of formula Id-Qb wherein X is $SO_2$, $R_1$ is ethyl, $R_2$ is $SO_2CF_3$ and $R_6$ is as defined in table W.

Table H-14 provides 17 compounds H-14.001 to H-14.017 of formula Id-Qb wherein X is $SO_2$, $R_1$ is ethyl, $R_2$ is $OSO_2CF_3$ and $R_6$ is as defined in table W.

Table H-15 provides 17 compounds H-15.001 to H-15.017 of formula Id-Qb wherein X is $SO_2$, $R_1$ is ethyl, $R_2$ is $OCF_3$ and $R_6$ is as defined in table W.

Table H-16 provides 17 compounds H-16.001 to H-16.017 of formula Id-Qb wherein $R_1$ is ethyl, X is S, $R_2$ is $OCHF_2$ and $R_6$ is as defined in table W.

Table H-17 provides 17 compounds H-17.001 to H-17.017 of formula Id-Qb wherein $R_1$ is ethyl, X is SO, $R_2$ is $OCHF_2$ and $R_6$ is as defined in table W.

Table H-18 provides 17 compounds H-18.001 to H-18.017 of formula Id-Qb wherein $R_1$ is ethyl, X is $SO_2$, $R_2$ is $OCHF_2$ and $R_6$ is as defined in table W.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the above-mentioned animal pests are:

from the order *Acarina*, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Derma-*

*tophagoides* spp, *Eotetranychus* spp, *Eriophyes* spp., *Hemitarsonemus* spp, *Hyalomma* spp., *Ixodes* spp., *Oligonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., Psylliodes spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order *Diptera*, for example,

*Aedes* spp., *Anopheles* spp, *Antherigona soccata, Bactrocera oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euschistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum*, Adalges spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Liogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Solenopsis invicta, Solenopsis* spp. and *Vespa* spp.;

from the order Isoptera, for example,

*Coptotermes* spp, *Cornitermes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Omiodes indica, Ostrinia nubilalis, Pammene* spp., *Pandemis* spp., *Panolis flammea, Papaipema nebris, Pectinophora gossypiella, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order *Siphonaptera*, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, *Cinnamomum* or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capensis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. oleracea, B. Pekinensis, B. rapa*), *Capsicum annuum, Cicer arietinum, Cichorium endivia, Cichorium* spp. (*C. intybus, C. endivia*), *Citrullus lanatus, Cucumis* spp. (*C. sativus, C. melo*), *Cucurbita* spp. (*C. pepo, C. maxima*), Cyanara spp. (*C. scolymus, C. cardunculus*), *Daucus carota, Foeniculum vulgare, Hypericum* spp., *Lactuca sativa, Lycopersicon* spp. (*L. esculentum, L. lycopersicum*), Mentha spp., *Ocimum basilicum, Petroselinum crispum, Phaseolus* spp. (*P. vulgaris, P. coccineus*), *Pisum sativum, Raphanus sativus, Rheum rhaponticum, Rosmarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johns wort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes,

*Ditylenchus* destructor, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, Hemicycliophora species and *Hemicriconemoides* species; *Hirshmanniella* species; Lance nematodes, *Hoploaimus* species; false rootknot nematodes, Nacobbus species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; Scutellonema species; Stubby root nematodes, *Trichodorus primitivus* and other *Trichodorus* species, Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); Helicelia (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides.*

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as 6-endotoxins, e.g. Cry1Ab, Cry1Ac, Cry1F, Cry1 Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (*Diptera*) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

| Examples of exotic woodborers of economic importance. | | |
|---|---|---|
| Family | Species | Host or Crop Infested |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

| Examples of native woodborers of economic importance. | | |
|---|---|---|
| Family | Species | Host or Crop Infested |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |

TABLE B-continued

| Examples of native woodborers of economic importance. | | |
|---|---|---|
| Family | Species | Host or Crop Infested |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *Ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus* verstitus and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of Such Parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order *Siphonaptera*, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., Trombicula spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirexjuvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances. Many surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers. The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol | 6% |

-continued

| Suspension concentrate | |
|---|---|
| ether (15 mol of ethylene oxide) | |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^{1}$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: Binary pump, heated column compartment and diode-array detector.

Column: Waters UPLC HSS T3 C18, 1.8 μm, 30×2.1 mm, Temp: 40° C., DAD Wavelength range (nm): 210 to 400, Solvent Gradient: A=water+5% Acetonitrile+0.1% HCOOH, B=Acetonitrile+0.05% HCOOH: gradient: 0 min 10% B; 0.-0.2 min 10-50% B; 0.2-0.7 min 50-100% B; 0.7-1.3 min 100% B; 1.3-1.4 min 100-10% B; 1.4-1.6 min 10% B; Flow (mL/min) 0.6.

Method 2:

Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 4.00 kV, Fragmentor: 100 V, Desolvation Temperature: 350° C., Gas Flow: 11 L/min, Nebulizer Gas: 45 psi, Mass range: 110 to 1000 Da) and a 1200 Series HPLC from Agilent: quaternary pump, heated column compartment and diode-array detector. Column: KINETEX EVO C18, 2.6 μm, 50×4.6 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 0% B, 100% A; 0.9-1.8 min 100% B; Flow (mL/min) 1.8.

Method 3:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: Binary pump, heated column compartment and diode-array detector. Column: Waters UPLC HSS T3 C18, 1.8 μm, 30×2.1 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 10% B; 0.-0.2 min 10-50% B; 0.2-0.7 min 50-100% B; Flow (mL/min) 0.8.

Example H1: Preparation of 2-[3-ethylsulfonyl-6-(trifluoromethyl)benzothiophen-2-yl]-6-(trifluoromethyl)-3H-pyrrolo[3,4-c]pyridin-1-one (Compound P1)

(P1)

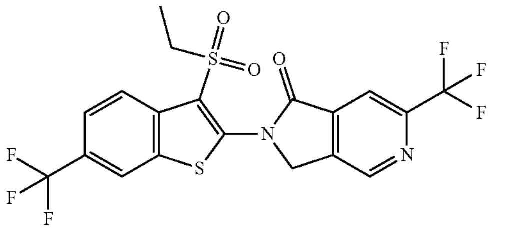

Step 1: Preparation of ethyl 3-chloro-6-(trifluoromethyl)benzothiophene-2-carboxylate (intermediate I-2) via 3-chloro-6-(trifluoromethyl)benzothiophene-2-carbonyl Chloride (Intermediate I-1)

(I-1)

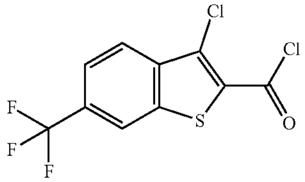

To a solution of (E)-3-[4-(trifluoromethyl)phenyl]prop-2-enoic acid (4.00 g, 19.0 mmol) in N,N-dimethylformamide (1.6 mL) and pyridine (0.80 mL) was added thionyl chloride (6.90 mL, 93.0 mmol) slowly at room temperature. The reaction mixture was heated to 145° C. and stirred for 2 hours. After cooling to room temperature, the reaction mixture was concentrated under reduced pressure to afford crude intermediate I-1.

(I-2)

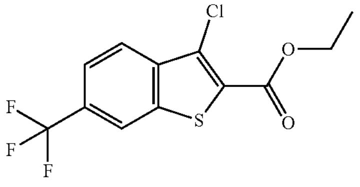

To crude intermediate I-1 was added ethanol (48 mL) slowly at 0° C. The reaction mixture was heated to 80° C. and stirred for 2 hours. After cooling to room temperature, the reaction mixture was concentrated under reduced pressure. Purification of the crude material by flash chromatography over silica gel (100% cyclohexane) afforded the desired product (2.98 g). $^1$H NMR (400 MHz, $CDCl_3$) δ ppm 1.46 (t, J=7.2 Hz, 3H), 4.47 (q, J=7.2 Hz, 2H), 7.73 (dd, J=8.5, 1.0 Hz, 1H), 8.07-8.15 (m, 2H).

Step 2: Preparation of ethyl 3-ethylsulfanyl-6-(trifluoromethyl)benzothiophene-2-carboxylate (Intermediate I-3)

(I-3)

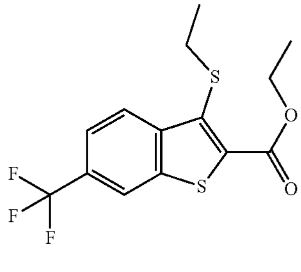

To a solution of ethyl 3-chloro-6-(trifluoromethyl)benzothiophene-2-carboxylate (intermediate I-2 prepared as described above, 76%, 18.8 g, 42.6 mmol) in N,N-dimethylformamide (188 mL) was added sodium ethanethiolate (6.45 g, 76.7 mmol). The reaction mixture was stirred at room temperature for 6 hours, then diluted with water and extracted three times with ethyl acetate. The combined organic layers were dried over sodium sulfate, filtered and concentrated under reduced pressure. Purification of the crude material by flash chromatography over silica gel (100% cyclohexane) afforded the desired product (9.20 g). $^1$H NMR (400 MHz, $CDCl_3$) δ ppm 1.22 (t, 3H), 1.47 (t, 3H), 3.06 (q, 2H), 4.48 (q, 2H), 7.61-7.74 (m, 1H), 8.15 (s, 1H), 8.32 (d, 1H).

Step 3: Preparation of ethyl 3-ethylsulfonyl-6-(trifluoromethyl)benzothiophene-2-carboxylate (Intermediate I-4)

(I-4)

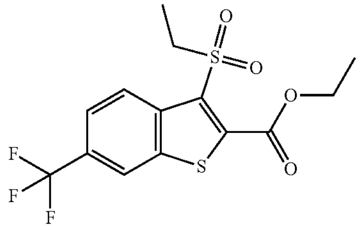

To a solution of ethyl 3-ethylsulfanyl-6-(trifluoromethyl)benzothiophene-2-carboxylate (intermediate I-3 prepared as described above, 9.20 g, 28.0 mmol) in dichloromethane (140 mL) was added 3-chloro-perbenzoic acid (15.0 g, 61.0 mmol) at 0° C. The reaction mixture was stirred at room temperature for 2 hours, then quenched at 0° C. with 2 M sodium hydroxide and extracted two times with ethyl acetate. The combined organic layers were washed with water and brine, dried over sodium sulfate, filtered and concentrated under reduced pressure. Purification of the crude material by flash chromatography over silica gel (gradient ethyl acetate in cyclohexane) afforded the desired product (5.50 g). $^1$H NMR (400 MHz, $CDCl_3$) δ ppm 1.40 (t, 3H), 1.46 (t, 3H), 3.60 (q, J=7.5 Hz, 2H), 4.51 (q, J=7.2 Hz, 2H), 7.77 (dd, J=8.9, 1.3 Hz, 1H), 8.19 (s, 1H), 8.75 (d, J=8.9 Hz, 1H).

Step 4: Preparation of 3-ethylsulfonyl-6-(trifluoromethyl)benzothiophene-2-carboxylic Acid (Intermediate I-5)

(I-5)

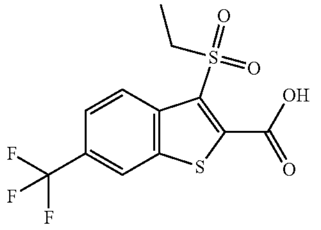

To a solution of ethyl 3-ethylsulfonyl-6-(trifluoromethyl) benzothiophene-2-carboxylate (intermediate I-4 prepared as described above, 5.50 g, 15.0 mmol) in methanol (44 mL) was added a solution of sodium hydroxide (1.20 g, 30.0 mmol) in water (22 mL). The reaction mixture was stirred at room temperature for 6 hours, then acidified with aqueous 2N hydrochloric acid, diluted with water and extracted three times with ethyl acetate. The combined organic layers were washed with brine, dried over sodium sulfate, filtered and concentrated under reduced pressure to afford the desired product (5.20 g), which was used without further purification. $^1$H NMR (400 MHz, DMSO-d6) δ ppm 1.22 (t, J=7.3 Hz, 3H), 3.63 (q, J=7.3 Hz, 2H), 7.93 (dd, J=8.9, 1.6 Hz, 1H), 8.59 (d, J=8.9 Hz, 1H), 8.77 (s, 1H).

Step 5: Preparation of tert-butyl N-[3-ethylsulfonyl-6-(trifluoromethyl)benzothiophen-2-yl]carbamate (Intermediate I-6)

(I-6)

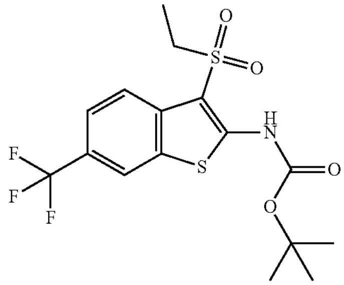

To a solution of 3-ethylsulfonyl-6-(trifluoromethyl)benzothiophene-2-carboxylic acid (intermediate I-5 prepared as described above, 5.20 g, 15.0 mmol) in tert-butanol (100 mL) was added triethylamine (3.50 mL, 25.0 mmol). The reaction mixture was heated to 90° C. and stirred for 10 minutes, before adding diphenylphosphoryl azide (5.40 mL, 25.0 mmol) dropwise over 15 minutes. The resulting reaction mixture was stirred at 90° C. for 1 hour and after cooling to room temperature, it was quenched with water and brine and extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (2.50 g). $^1$H NMR (400 MHz, $CDCl_3$) δ ppm 1.28 (t, 3H), 1.60 (s, 9H), 3.28 (q, J=7.3 Hz, 2H), 7.67 (d, J=8.7 Hz, 1H), 8.02 (s, 1H), 8.14 (d, J=8.7 Hz, 1H), 9.96 (s, 1H).

Step 6: Preparation of 3-ethylsulfonyl-6-(trifluoromethyl)benzothiophen-2-amine (Intermediate I-7)

(I-7)

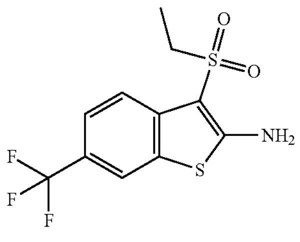

To a solution of tert-butyl N-[3-ethylsulfonyl-6-(trifluoromethyl)benzothiophen-2-yl]carbamate (intermediate I-6 prepared as described above, 2.30 g, 5.60 mmol) in dichloromethane (23 mL) was added 2,2,2-trifluoroacetic acid (5.20 mL, 67.0 mmol) dropwise. The reaction mixture was stirred at room temperature for 16 hours, then concentrated under reduced pressure. The resulting residue was diluted with water, neutralized with sat. aq. sodium bicarbonate and extracted three times with ethyl acetate. The combined organic layers were washed with brine, dried over sodium sulfate, filtered and concentrated under reduced pressure. Purification of the crude material by flash chromatography over silica gel (100% cyclohexane) afforded the desired product (0.600 g). $^1$H NMR (400 MHz, $CDCl_3$) δ ppm 1.34 (t, 3H), 3.22 (q, J=7.3 Hz, 2H), 6.26 (br s, 2H), 7.58 (d, J=8.6 Hz, 1H), 7.82 (s, 1H), 7.93 (d, J=8.6 Hz, 1H).

Step 7: Preparation of methyl 5-[[[3-ethylsulfonyl-6-(trifluoromethyl)benzothiophen-2-yl]amino]methyl]-2-(trifluoromethyl)pyridine-4-carboxylate (Intermediate I-8)

(I-8)

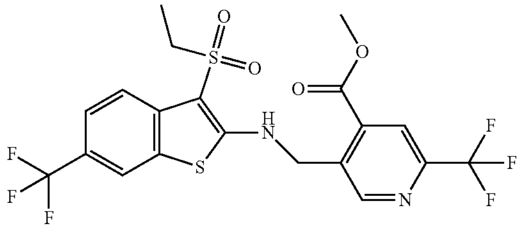

To a solution of 3-ethylsulfonyl-6-(trifluoromethyl)benzothiophen-2-amine (intermediate I-7 prepared as described above, 0.600 g, 1.94 mmol) in N,N-dimethylformamide (15 mL) was added sodium hydride (60%, 0.116 g, 2.91 mmol) at 0° C. and the reaction mixture was stirred at this temperature for 30 minutes. Then a solution of methyl 5-(bromomethyl)-2-(trifluoromethyl)pyridine-4-carboxylate (intermediate IP-6 prepared as described below; 60%, 1.35 g, 2.72 mmol) in N,N-dimethylformamide (6 mL) was added and the reaction mixture further stirred at 0° C. for 2 hours. The mixture was diluted with water and extracted two times with ethyl acetate. The combined organic layers were concentrated under reduced pressure. Purification of the crude material by flash chromatography over silica gel (gradient ethyl acetate in cyclohexane) afforded the desired product (0.910 g). LCMS (method 1): m/z 527 [M+H]+, retention time Rt=1.24 min.

Step 8: Preparation of 5-[[[3-ethylsulfonyl-6-(trifluoromethyl)benzothiophen-2-yl]amino]methyl]-2-(trifluoromethyl)pyridine-4-carboxylic Acid (Intermediate I-9)

(I-9)

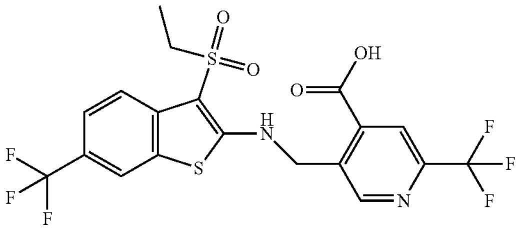

To a suspension of methyl 5-[[[3-ethylsulfonyl-6-(trifluoromethyl)benzothiophen-2-yl]amino]methyl]-2-(trifluoromethyl)pyridine-4-carboxylate (intermediate I-8 prepared as described above, 0.800 g, 1.52 mmol) in methanol (16 mL) was added a solution of dihydroxybarium octahydrate (0.959 g, 3.04 mmol) in water (8 mL) at 0° C. The reaction mixture was stirred at room temperature for 2 hours, then diluted with water, acidified with aqueous 2N hydrochloric acid and extracted three times with ethyl acetate. The combined organic layers were concentrated under reduced pressure. Purification of the crude material by flash chromatography over silica gel (gradient methanol in ethyl acetate) afforded the desired product (0.570 g, 0.779 mmol). LCMS (method 1): m/z 513 [M+H]+, retention time Rt=1.12 min.

Step 9: Preparation of 2-[3-ethylsulfonyl-6-(trifluoromethyl)benzothiophen-2-yl]-6-(trifluoromethyl)-3H-pyrrolo[3,4-c]pyridin-1-one (Title Compound P1)

(P1)

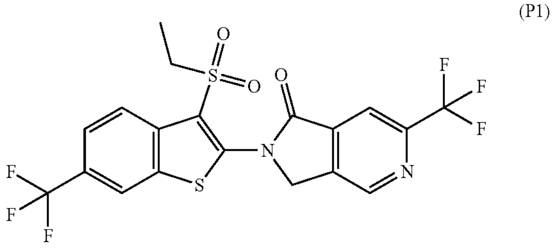 [SMILES: CCS(=O)(=O)c1c(N2Cc3cnc(C(F)(F)F)cc3C2=O)sc2cc(C(F)(F)F)ccc12]

To a solution of 5-[[[3-ethylsulfonyl-6-(trifluoromethyl) benzothiophen-2-yl]amino]methyl]-2-(trifluoromethyl)pyridine-4-carboxylic acid (intermediate I-9 prepared as described above, 0.620 g, 1.21 mmol) in pyridine (3.1 mL) was added phosphorus(V) oxychloride (0.228 mL, 2.42 mmol) at 0° C. The reaction mixture was stirred at 0° C. for 4 hours, then diluted with water, acidified with aqueous 1N hydrochloric acid and extracted three times with ethyl acetate. The combined organic layers were washed with brine, dried over sodium sulfate, filtered and concentrated under reduced pressure. Purification of the crude material by flash chromatography over silica gel (gradient ethyl acetate in cyclohexane) afforded the desired product (80 mg). LCMS (method 1): m/z 495 [M+H]+, retention time Rt=1.16 min. $^1$H NMR (400 MHz, $CDCl_3$) δ ppm 1.42 (t, J=7.5 Hz, 3H), 3.46 (q, J=7.5 Hz, 2H), 5.15 (s, 2H), 7.81 (d, J=8.8 Hz, 1H), 8.21 (m, 2H), 8.52 (d, J=8.8 Hz, 1H), 9.06 (s, 1H).

Example H2: Preparation of 6-[3-ethylsulfonyl-7-(trifluoromethyl)imidazo[1,2-a]pyridin-2-yl]-3-(trifluoromethyl)-7H-pyrrolo[3,4-b]pyridin-5-one (Compound P2)

(P2)

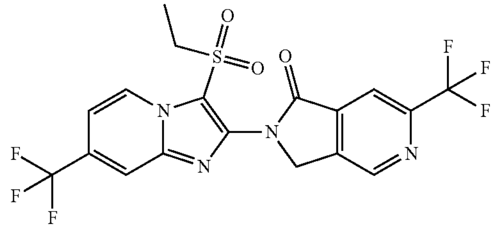

Step 1: Preparation of tert-butyl N-[3-ethylsulfonyl-7-(trifluoromethyl)imidazo[1,2-a]pyridin-2-yl]carbamate (Intermediate II-1)

(II-1)

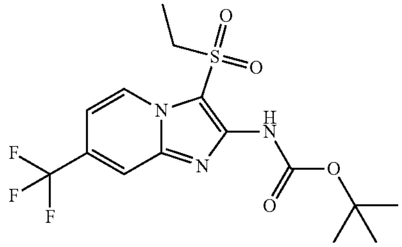

To a solution of 3-ethylsulfonyl-7-(trifluoromethyl)imidazo[1,2-a]pyridine-2-carboxylic acid (CAS 2181821-89-4; 2.50 g, 7.76 mmol) in tert-butanol (50 mL) was added triethylamine (1.75 mL, 12.4 mmol). The reaction mixture was heated to 90° C. and stirred for 10 minutes, before adding diphenylphosphoryl azide (2.73 mL, 12.4 mmol) dropwise over 15 minutes. The resulting reaction mixture was stirred at 90° C. for 40 minutes. After cooling to room temperature, the mixture was quenched with water and brine, and extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (0.850 g). $^1$H NMR (400 MHz, DMSO-d6) δ ppm 1.27 (t, 3H), 1.48 (s, 9H), 3.66 (q, J=7.34 Hz, 2H), 7.47 (dd, J=7.34, 1.96 Hz, 1H), 8.24 (s, 1H), 8.94 (d, J=7.34 Hz, 1H), 9.57 (s, 1H).

Step 2: Preparation of methyl 2-chloro-5-(trifluoromethyl)pyridine-3-carboxylate (Intermediate II-2)

(II-2)

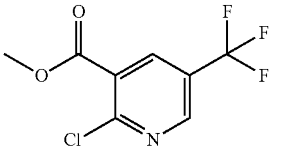

To a solution of 2-chloro-5-(trifluoromethyl)pyridine-3-carboxylic acid (CAS 505084-59-3; 7.00 g, 31.0 mmol) in N,N-dimethylformamide (70 mL) was added cesium carbonate (12.1 g, 37.2 mmol). The reaction mixture was stirred at room temperature for 5 minutes, before addition of iodomethane (2.90 mL, 46.6 mmol). Stirring was continued at room temperature for 1 hour. The reaction mixture was diluted with ice water and extracted three times with ethyl acetate. The combined organic layers were washed with ice water and brine, dried over sodium sulfate, filtered and concentrated under reduced pressure to afford the desired product (7.00 g), which was used without further purification. LCMS (method 1): m/z 240/242 $[M+H]^+$, retention time Rt=1.00 min. $^1$H NMR (400 MHz, $CDCl_3$) δ ppm 4.01 (s, 3H), 8.41 (d, 1H), 8.78 (d, 1H).

Step 3: Preparation of methyl 2-methyl-5-(trifluoromethyl)pyridine-3-carboxylate (Intermediate II-3)

(II-3)

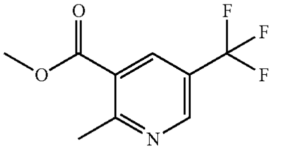

A reaction vessel was charged with methylboronic acid (7.73 g, 125 mmol), potassium phosphate tribasic (26.6 g, 125 mmol), tricyclohexylphosphane (1.17 g, 4.17 mmol), followed by toluene (100 mL) and water (13 mL). The flask was purged with nitrogen for 15 minutes. To the reaction mixture were added methyl 2-chloro-5-(trifluoromethyl) pyridine-3-carboxylate (intermediate II-2 prepared as described above, 10.0 g, 41.7 mmol) and palladium(II) acetate (0.469 g, 2.09 mmol). The reaction mixture was first heated to 100° C. and stirred for 2 hours, then at 90° C. overnight. After cooling to room temperature, the mixture was diluted with water and ethyl acetate, and filtered over a Celite pad. The layers were separated, and the organic layer was dried over sodium sulfate, filtered and concentrated under reduced pressure to afford the desired product (5.00 g), which was used without further purification. LCMS (method 1): m/z 220 $[M+H]^+$, retention time Rt=0.93 min. $^1$H NMR (400 MHz, $CDCl_3$) δ ppm 2.92 (s, 3H), 3.97 (s, 3H), 8.44 (d, 1H), 8.87 (m, 1H).

Step 4: Preparation of methyl 2-(bromomethyl)-5-(trifluoromethyl)pyridine-3-carboxylate (Intermediate II-4)

(II-4)

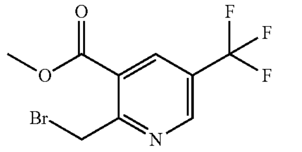

To a solution of methyl 2-methyl-5-(trifluoromethyl)pyridine-3-carboxylate (intermediate II-3 prepared as described above, 3.50 g, 16.0 mmol) in tetrachloromethane (80 mL) were added N-bromosuccinimide (4.00 g, 22.0 mmol) and benzoyl peroxide (70%, 1.40 g, 4.00 mmol). The reaction mixture was heated to 70° C. and stirred for 3 hours. After cooling to room temperature, it was diluted with ice water and extracted three times with dichloromethane. The combined organic layers were washed with brine, dried over sodium sulfate, filtered and concentrated under reduced pressure. Purification of the crude material by flash chromatography over silica gel (gradient ethyl acetate in cyclohexane) afforded the desired product (1.40 g). LCMS (method 1): m/z 298/300 $[M+H]^+$, retention time Rt=1.01 min. $^1$H NMR (400 MHz, $CDCl_3$) δ ppm: 4.03 (s, 3H) 5.08 (s, 2H), 8.53 (d, J=2.01 Hz, 1H), 8.96 (m, 1H).

Similarly, ethyl 2-(bromomethyl)-5-(trifluoromethyl) pyridine-3-carboxylate (II-4-a) can be prepared:

(II-4-a)

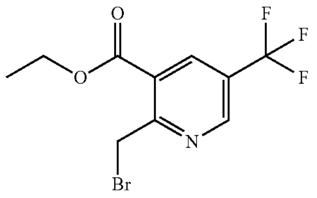

LCMS (method 1): m/z 312/314 $[M+H]^+$, retention time 1.14 min. $^1$H NMR (400 MHz, $CDCl_3$) δ/ppm: 1.47 (t, 3H), 4.49 (q, 2H), 5.07 (s, 2H), 8.51 (s, 1H), 8.95 (s, 1H).

Similarly, methyl 2-(bromomethyl)-5-(trifluoromethyl) benzoate (CAS 875895-66-2; 11-4-b) can be prepared:

(II-4-b)

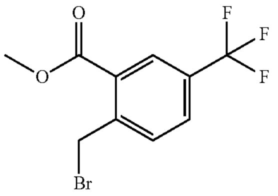

$^1$H NMR (400 MHz, $CDCl_3$) δ/ppm: 3.99 (s, 3H), 4.98 (s, 2H), 7.62 (d, J=8.1 Hz, 1H), 7.76 (dd, J=8.1, 1.5 Hz, 1H), 8.24 (d, J=1.5 Hz, 1H).

Similarly, methyl 2-(bromomethyl)-5-(difluoromethoxy) benzoate (CAS 944718-50-7; 11-4-c) can be prepared from methyl 5-(difluoromethoxy)-2-methyl-benzoate (CAS 1190320-23-0):

(II-4-c)

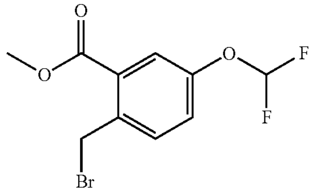

$^1$H NMR (400 MHz, $CDCl_3$) δ/ppm: 3.98 (s, 3H), 4.96 (s, 2H), 6.57 (t, 1H), 7.28 (dd, 1H), 7.50 (d, 1H), 7.74 (d, 1H).

Step 5: Preparation of methyl 2-[[tert-butoxycarbonyl-[3-ethylsulfonyl-7-(trifluoromethyl)imidazo[1,2-a]pyridin-2-yl]amino]methyl]-5-(trifluoromethyl) pyridine-3-carboxylate (Intermediate II-5)

(II-5)

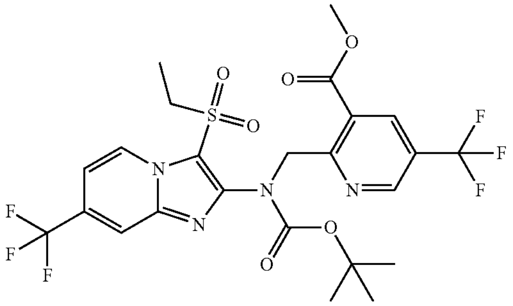

To a solution of tert-butyl N-[3-ethylsulfonyl-7-(trifluoromethyl)imidazo[1,2-a]pyridin-2-yl]carbamate (intermediate II-1 prepared as described above, 0.450 g, 1.14 mmol) in acetonitrile (10 mL) were added methyl 2-(bromomethyl)-5-(trifluoromethyl)pyridine-3-carboxylate (intermediate II-4 prepared as described above, 0.443 g, 1.49 mmol) and cesium carbonate (0.560 g, 1.72 mmol). The reaction mixture was heated to 50° C. and stirred for 2 hours. After cooling to room temperature, it was quenched with ice water and extracted two times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (0.510 g). LCMS (method 1): m/z 611 $[M+H]^+$, retention time Rt=1.25 min. $^1$H NMR (400 MHz, $CDCl_3$) δ ppm 1.37 (s, 9H), 1.47 (t, 3H), 3.71 (br q, 2H), 3.98 (s, 3H), 5.55 (s, 2H), 7.14 (br d, 1H), 7.81 (s, 1H), 8.58 (s, 1H), 8.92 (br d, 1H), 8.97 (s, 1H).

Step 6: Preparation of methyl 2-[[[3-ethylsulfonyl-7-(trifluoromethyl)imidazo[1,2-a]pyridin-2-yl] amino]methyl]-5-(trifluoromethyl)pyridine-3-carboxylate (Intermediate II-6)

(II-6)

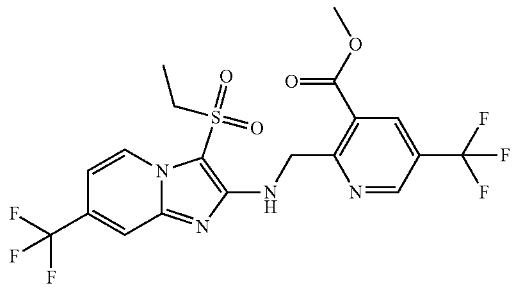

To a solution methyl 2-[[tert-butoxycarbonyl-[3-ethylsulfonyl-7-(trifluoromethyl)imidazo[1,2-a]pyridin-2-yl] amino]methyl]-5-(trifluoromethyl)pyridine-3-carboxylate (intermediate II-5 prepared as described above, 0.510 g, 0.835 mmol) in dichloromethane (10 mL) was added 2,2,2-trifluoroacetic acid (0.673 mL, 8.35 mmol) dropwise at 0° C. The reaction mixture was stirred at room temperature overnight, then quenched with sat. aq. sodium bicarbonate and extracted three times with ethyl acetate. The combined organic layers were washed with brine, dried over sodium sulfate, filtered and concentrated under reduced pressure to afford the desired product (0.400 g), which was used without further purification. LCMS (method 1): m/z 511 $[M+H]^+$, retention time Rt=1.17 min. $^1$H NMR (400 MHz, DMSO-d6) δ ppm 1.19 (t, 3H), 3.43 (q, J=7.34 Hz, 2H), 3.96 (s, 3H), 5.17 (d, J=5.5 Hz, 2H), 7.05 (t, J=5.5 Hz, 1H), 7.31 (dd, J=7.09, 1.83 Hz, 1H), 7.95 (s, 1H), 8.55 (d, J=1.83 Hz, 1H), 8.71 (d, J=7.09 Hz, 1H), 9.14 (s, 1H).

Step 7: Preparation of 2-[[[3-ethylsulfonyl-7-(trifluoromethyl)imidazo[1,2-a]pyridin-2-yl]amino] methyl]-5-(trifluoromethyl)pyridine-3-carboxylic Acid (Intermediate II-7)

(II-7)

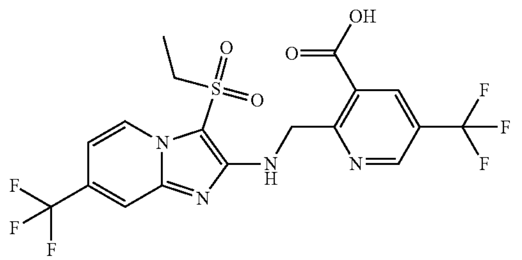

To a solution of methyl 2-[[[3-ethylsulfonyl-7-(trifluoromethyl)imidazo[1,2-a]pyridin-2-yl]amino]methyl]-5-(trifluoromethyl)pyridine-3-carboxylate (intermediate II-6 prepared as described above, 0.400 g, 0.784 mmol) in methanol (8 mL) and water (4 mL) was added dihydroxybarium octahydrate (0.494 g, 1.57 mmol). The reaction mixture was stirred at room temperature for 16 hours, then acidified with aqueous 2N hydrochloric acid and extracted three times with ethyl acetate. The combined organic layers were dried over sodium sulfate, filtered and concentrated under reduced pressure to afford the desired product (0.380 g). LCMS (method 1): m/z 497 $[M+H]^+$, retention time Rt=1.04 min. $^1H$ NMR (400 MHz, DMSO-d6) δ ppm 1.18 (t, 3H), 3.43 (q, 2H), 5.19 (d, J=5.4 Hz, 2H), 7.12 (t, J=5.4 Hz, 1H), 7.31 (dd, J=7.1, 1.9 Hz, 1H), 7.98 (s, 1H), 8.53 (d, J=1.9 Hz, 1H), 8.70 (d, J=7.1 Hz, 1H), 9.12 (s, 1H).

Step 8: Preparation of 6-[3-ethylsulfonyl-7-(trifluoromethyl)imidazo[1,2-a]pyridin-2-yl]-3-(trifluoromethyl)-7H-pyrrolo[3,4-b]pyridin-5-one (Title Compound P2)

(P2)

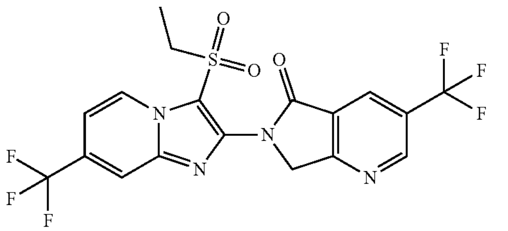

To a solution of 2-[[[3-ethylsulfonyl-7-(trifluoromethyl)imidazo[1,2-a]pyridin-2-yl]amino]methyl]-5-(trifluoromethyl)pyridine-3-carboxylic acid (intermediate II-7 prepared as described above, 0.300 g, 0.604 mmol) in pyridine (6 mL) was added phosphorus(V) oxychloride (0.114 mL, 1.21 mmol) at 0° C. The reaction mixture was slowly allowed to reach room temperature and stirred for 1 hour, then acidified with aqueous 1N hydrochloric acid and extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (0.187 g). LCMS (method 1): m/z 479 $[M+H]^+$, retention time Rt=1.06 min. $^1H$ NMR (400 MHz, $CDCl_3$) δ ppm 1.53 (t, J=7.46 Hz, 3H), 3.84 (q, J=7.46 Hz, 2H), 5.25 (s, 2H), 7.29 (d, J=7.34 Hz, 1H), 8.04 (s, 1H), 8.48 (s, 1H), 9.03 (d, J=7.34 Hz, 1H), 9.13 (s, 1H).

Example H3: Preparation of 2-[3-ethylsulfonyl-7-(2,2,2-trifluoroethoxy)imidazo[1,2-a]pyridin-2-yl]-6-(trifluoromethylsulfonyl)isoindolin-1-one (Compound P33)

(P33)

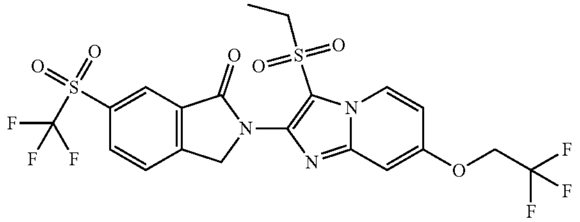

Step 1: Preparation of 4-(2,2,2-trifluoroethoxy)pyridin-2-amine (Intermediate III-1)

(III-1)

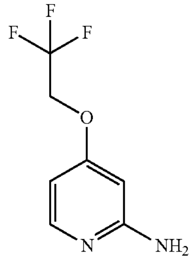

To a solution of 2-aminopyridin-4-ol (15.0 g, 136 mmol) in DMSO (150 mL) were added potassium carbonate (95.5 g, 681 mmol) and 2-iodo-1,1,1-trifluoroethane (72.2 g, 341 mmol) and the reaction mixture was heated to 100° C. and stirred for 12 hours. After cooling to room temperature, the reaction mixture was extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (14.0 g). LCMS (method 1): m/z 193 $[M+H]^+$, retention time Rt=0.19 min. $^1H$ NMR (400 MHz, DMSO-$d_6$) δ ppm: 4.73 (q, 2H), 5.93 (s, 2H), 6.02 (d, 1H), 6.24 (dd, 1H), 7.79 (d, 1H).

Step 2: Preparation of ethyl 7-(2,2,2-trifluoroethoxy)imidazo[1,2-a]pyridine-2-carboxylate (Intermediate III-2)

(III-2)

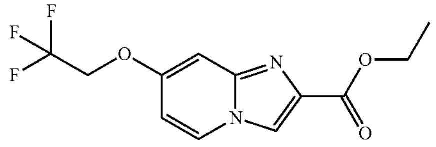

To a solution of 4-(2,2,2-trifluoroethoxy)pyridin-2-amine (intermediate III-1 prepared as described above, 14.0 g, 72.9 mmol) in ethanol (140 mL) were added ethyl 3-bromo-2-oxo-propanoate (17.1 g, 87.4 mmol, 11.0 mL) and sodium bicarbonate (12.2 g, 146 mmol). The reaction mixture was heated to 85° C. and stirred for 7 hours. After cooling to room temperature, the reaction mixture was diluted with water, and extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (11.0 g). LCMS (method 1): m/z 289 $[M+H]^+$, retention time Rt=1.19 min. $^1H$ NMR (400 MHz, DMSO-$d_6$) δ ppm: 1.31 (t, 3H), 4.29 (q, 2H), 6.75 (dd, 1H), 7.02 (d, 1H), 8.07 (d, 1H), 8.11 (s, 1H).

Step 3: Preparation of ethyl 3-chloro-7-(2,2,2-trifluoroethoxy)imidazo[1,2-a]pyridine-2-carboxylate (Intermediate III-3)

(III-3)

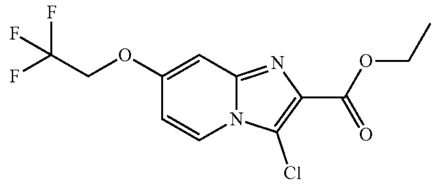

To a solution of ethyl 7-(2,2,2-trifluoroethoxy)imidazo[1,2-a]pyridine-2-carboxylate (intermediate III-2 prepared as described above, 12.0 g, 41.6 mmol) in acetonitrile (120 mL) was added 1-chloropyrrolidine-2,5-dione (6.67 g, 50.0 mmol) and the reaction mixture was stirred at room temperature for 16 hours. Ice cold water was added to the reaction mixture, the precipitated compound was filtered and dried to afford the desired product (10.5 g), which was used without further purification. LCMS (method 2): m/z 323/325 $[M+H]^+$, retention time Rt=2.32 min. $^1H$ NMR (400 MHz, $CDCl_3$) δ ppm: 1.48 (t, 3H), 4.40-4.54 (m, 4H), 6.88 (dd, 1H), 7.01 (d, 1H), 8.08 (d, 1H).

Step 4: Preparation of ethyl 3-ethylsulfanyl-7-(2,2,2-trifluoroethoxy)imidazo[1,2-a]pyridine-2-carboxylate (Intermediate III-4)

(III-4)

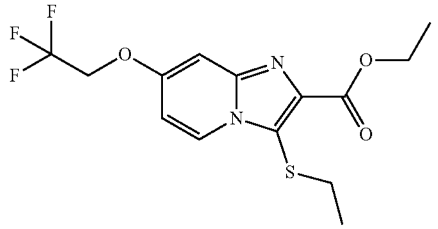

To a solution of ethyl 3-chloro-7-(2,2,2-trifluoroethoxy)imidazo[1,2-a]pyridine-2-carboxylate (intermediate III-3 prepared as described above, 9.60 g, 30.0 mmol) in methylsulfinylmethane (96.0 mL) at 15-20° C. was added sodium ethanethiolate (5.00 g, 60.0 mmol) portionwise, and the reaction mixture was stirred at room temperature for 2 hours. Ice cold water was added to the reaction mixture, the precipitated compound was filtered and dried to afford the desired product (9.60 g), which was used without further purification. LCMS (method 1): m/z 349 $[M+H]^+$, retention time Rt=1.47 min. $^1H$ NMR (400 MHz, DMSO-$d_6$) δ ppm: 1.05 (t, 3H), 1.34 (t, 3H), 2.85 (q, 2H), 4.33 (q, 2H), 4.94 (q, 2H), 6.97 (dd, 1H), 7.28 (d, 1H), 8.56 (d, 1H).

Step 5: Preparation of ethyl 3-ethylsulfonyl-7-(2,2,2-trifluoroethoxy)imidazo[1,2-a]pyridine-2-carboxylate (Intermediate III-5)

(III-5)

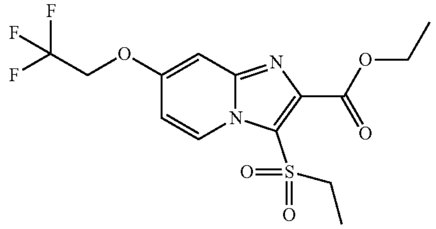

To a solution of ethyl 3-ethylsulfanyl-7-(2,2,2-trifluoroethoxy)imidazo[1,2-a]pyridine-2-carboxylate (intermediate III-4 prepared as described above, 9.60 g, 28.0 mmol) in trifluoromethylbenzene (96.0 mL) was added 3-chlorobenzenecarboperoxoic acid (18.4 g, 74.9 mmol) at 0° C. The reaction mixture was stirred at room temperature for 24 hours, then quenched with water and aqueous 2 M sodium hydroxide, and the product extracted twice with ethyl acetate. The combined organic layers were washed with water and brine, dried over sodium sulfate, filtered and concentrated under reduced pressure. Purification of the crude material by flash chromatography over silica gel (gradient ethyl acetate in cyclohexane) afforded the desired product (8.10 g). LCMS (method 1): m/z 381 $[M+H]^+$, retention time Rt=0.96 min. $^1H$ NMR (400 MHz, $CDCl_3$) δ ppm: 1.36 (t, 3H), 1.48 (t, 3H), 3.73 (q, 2H), 4.42-4.56 (m, 4H), 6.90 (dd, 1H), 7.06 (d, 1H), 9.16 (d, 1H).

Step 6: Preparation of 3-ethylsulfonyl-7-(2,2,2-trifluoroethoxy)imidazo[1,2-a]pyridine-2-carboxylic Acid (Intermediate III-6)

(III-6)

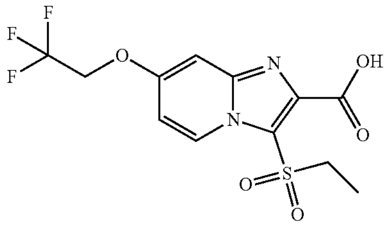

To a solution of ethyl 3-ethylsulfonyl-6-(trifluoromethyl)benzothiophene-2-carboxylate (intermediate III-5 prepared as described above, 8.10 g, 21.0 mmol) in tetrahydrofuran (81 mL) was added a solution of lithium hydroxide (0.77 g, 32.0 mmol) in water (32 mL) at 0-5° C. The reaction mixture was stirred at room temperature for 16 hours, then acidified with aqueous 2N hydrochloric acid. The precipitate formed was filtered and dried to afford the desired product (6.00 g), which was used without further purification. LCMS (method 1): m/z 353 $[M+H]^+$, retention time Rt=0.83 min. $^1H$ NMR (400 MHz, DMSO-$d_6$) δ ppm: 1.21 (t, 3H), 3.64 (q, 3H), 5.00 (q, 2H), 7.15 (dd, 1H), 7.46 (d, 1H), 8.87 (d, 1H).

Step 7: Preparation of tert-butyl N-[3-ethylsulfonyl-7-(2,2,2-trifluoroethoxy)imidazo[1,2-a]pyridin-2-yl] carbamate (Intermediate III-7)

(III-7)

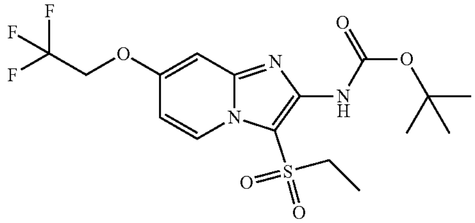

To a solution of 3-ethylsulfonyl-7-(2,2,2-trifluoroethoxy) imidazo[1,2-a]pyridine-2-carboxylic acid (intermediate III-6 prepared as described above, 3.50 g, 9.90 mmol) in tert-butanol (70 mL) was added triethylamine (2.20 mL, 16.0 mmol). The reaction mixture was heated to 90° C. and stirred for 10 minutes before adding diphenylphosphoryl azide (3.50 mL, 16.0 mmol) dropwise over 15 minutes. The resulting reaction mixture was stirred at 90° C. for 30 minutes and after cooling to room temperature, it was quenched with water and brine and the product extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (2.90 g). LCMS (method 1): m/z 424 $[M+H]^+$, retention time Rt=1.03 min. $^1H$ NMR (400 MHz, $CDCl_3$) δ ppm: 1.32 (t, 3H), 1.56 (s, 9H), 3.22 (q, 2H), 4.41 (q, 2H), 6.79 (dd, 1H), 7.05 (d, 1H), 8.16 (s, 1H), 8.51 (d, 1H).

Step 8: Preparation of methyl 2-[[tert-butoxycarbonyl-[3-ethylsulfonyl-7-(2,2,2-trifluoroethoxy) imidazo[1,2-a]pyridin-2-yl]amino]methyl]-5-(trifluoromethylsulfonyl)benzoate (Intermediate III-8)

(III-8)

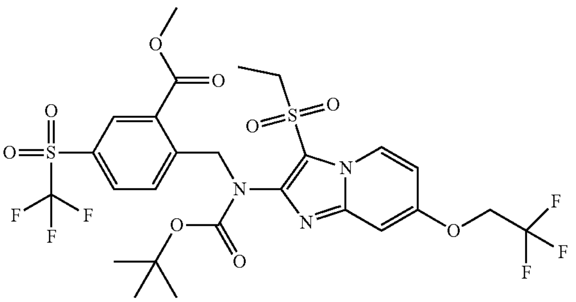

To a solution of tert-butyl N-[3-ethylsulfonyl-7-(2,2,2-trifluoroethoxy)imidazo[1,2-a]pyridin-2-yl]carbamate (intermediate III-7 prepared as described above, 1.00 g, 2.4 mmol) in acetonitrile (15 mL) were added cesium carbonate (1.20 g, 3.50 mmol), then a solution of methyl 2-(bromomethyl)-5-(trifluoromethylsulfonyl)benzoate (prepared according to WO 20/174,094, 1.80 g, 3.50 mmol) in acetonitrile (2 mL) dropwise. The reaction mixture was heated to 50° C. and stirred for 2 hours. After cooling to room temperature, it was diluted with water and the product extracted three times with ethyl acetate. The combined organic layers were washed with water and brine, dried over sodium sulfate, filtered and concentrated under reduced pressure. Purification of the crude material by flash chromatography over silica gel (gradient ethyl acetate in cyclohexane) afforded the desired product (2.10 g). LCMS (method 2): m/z 704 $[M+H]^+$, retention time Rt=1.68 min.

Step 9: Preparation of methyl 2-[[[3-ethylsulfonyl-7-(2,2,2-trifluoroethoxy)imidazo[1,2-a]pyridin-2-yl] amino]methyl]-5-(trifluoromethylsulfonyl)benzoate (Intermediate III-9)

(III-9)

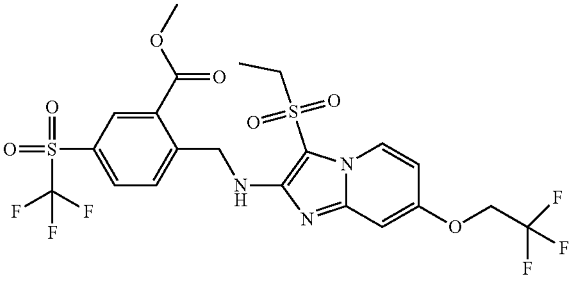

To a solution of methyl 2-[[tert-butoxycarbonyl-[3-ethylsulfonyl-7-(2,2,2-trifluoroethoxy)imidazo[1,2-a]pyridin-2-yl]amino]methyl]-5-(trifluoromethylsulfonyl)benzoate (intermediate III-8 prepared as described above, 2.70 g, 3.80 mmol) in benzotrifluoride (14.0 mL) was added 2,2,2-trifluoroacetic acid (5.90 mL, 77.0 mmol). The reaction mixture was stirred at room temperature for 4 hours, then diluted with water and the product extracted with ethyl acetate. The combined organic layers were washed with saturated aqueous sodium bicarbonate, dried over sodium sulfate, filtered and concentrated under reduced pressure. Purification of the crude material by flash chromatography over silica gel (gradient ethyl acetate in cyclohexane) afforded the desired product (1.30 g). LCMS (method 2): m/z 604 $[M+H]^+$, retention time Rt=1.60 min.

Step 10: Preparation of 2-[[[3-ethylsulfonyl-7-(2,2,2-trifluoroethoxy)imidazo[1,2-a]pyridin-2-yl]amino] methyl]-5-(trifluoromethylsulfonyl)benzoic Acid (Intermediate III-10)

(III-10)

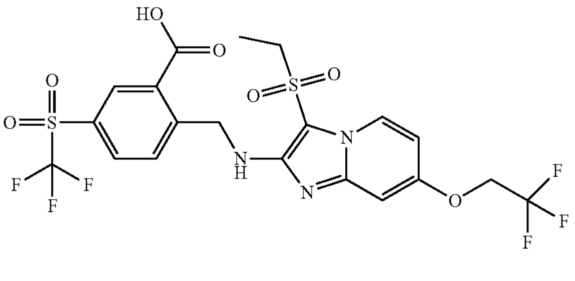

To a solution of methyl 2-[[[3-ethylsulfonyl-7-(2,2,2-trifluoroethoxy)imidazo[1,2-a]pyridin-2-yl]amino]methyl]-5-(trifluoromethylsulfonyl)benzoate (intermediate III-9 prepared as described above, 0.70 g, 1.16 mmol) in NMP (14.0 mL) was added lithium chloride (0.34 g, 8.12 mmol) and the reaction mixture was stirred in the microwave at 150° for 1.5 hour. The mixture was diluted with water, then acidified with aqueous 2N hydrochloric acid. The formed precipitate was filtered and dried to afford the desired product (0.35 g), which was used without further purification. LCMS (method 2): m/z 590 $[M+H]^+$, retention time Rt=1.51 min.

Step 11: Preparation of 2-[3-ethylsulfonyl-7-(2,2,2-trifluoroethoxy)imidazo[1,2-a]pyridin-2-yl]-6-(trifluoromethylsulfonyl)isoindolin-1-one (Compound P33)

(P33)

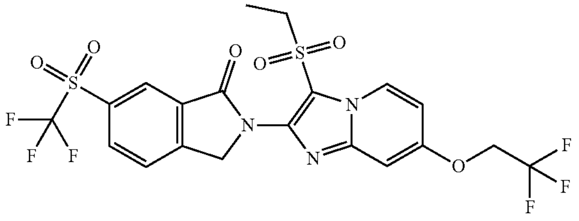

To a solution of 2-[[[3-ethylsulfonyl-7-(2,2,2-trifluoroethoxy)imidazo[1,2-a]pyridin-2-yl]amino]methyl]-5-(trifluoromethylsulfonyl)benzoic acid (intermediate III-10 prepared as described above, 0.80 g, 1.36 mmol) in pyridine (4.00 mL) was added phosphorus oxychloride (0.26 mL, 2.71 mmol) at 0° C. and the reaction mixture was stirred at room temperature for 10 minutes. The mixture was diluted with water, then acidified with aqueous 1N hydrochloric acid, and the product extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (0.29 g). LCMS (method 2): m/z 572 $[M+H]^+$, retention time Rt=1.53 min. $^1H$ NMR (400 MHz, $CDCl_3$) δ ppm: 1.50 (t, 3H), 3.79 (q, 2H), 4.48 (q, 2H), 5.21 (s, 2H), 6.90 (dd, 1H), 6.97 (d, 1H), 7.88 (d, 1H), 8.31 (dd, 1H), 8.63 (s, 1H), 8.78 (d, 1H).

Example H4: Preparation of N-[3-ethylsulfonyl-2-[5-oxo-3-(trifluoromethyl)-7H-pyrrolo[3,4-b]pyridin-6-yl]imidazo[1,2-a]pyridin-6-yl]acetamide (Compound P36)

(P36)

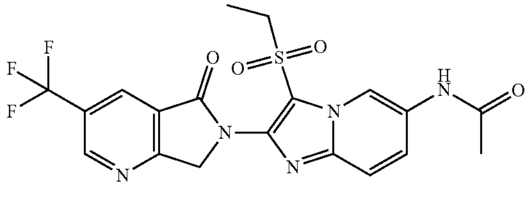

Step 1: Preparation of ethyl 2-[[(6-bromo-3-ethylsulfonyl-imidazo[1,2-a]pyridin-2-yl)-tert-butoxycarbonyl-amino]methyl]-5-(trifluoromethyl)pyridine-3-carboxylate (Intermediate IV-1)

(IV-1)

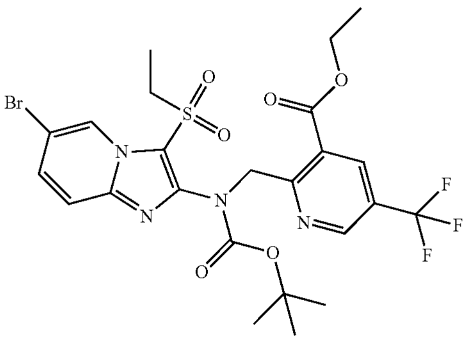

To a solution of tert-butyl N-(6-bromo-3-ethylsulfonyl-imidazo[1,2-a]pyridin-2-yl)carbamate (intermediate IQ-8 prepared in analogy to intermediate III-7 described above, 0.84 g, 2.08 mmol) in acetonitrile (13.0 mL) was added cesium carbonate (1.02 g, 3.12 mmol). The reaction mixture was stirred at room temperature for 5 minutes, then a solution of ethyl 2-(bromomethyl)-5-(trifluoromethyl)pyridine-3-carboxylate (intermediate II-4-a prepared in analogy to intermediate II-4 described above, 0.84 g, 2.70 mmol) in acetonitrile (8.4 mL) was added dropwise and the resulting mixture stirred at 50° C. for 2 hours. After cooling to room temperature, ice cold water was added and the product extracted twice with ethyl acetate. The combined organic layers were washed with water and brine, dried over sodium sulfate, filtered and concentrated under reduce pressure. The crude residue was purified by chromatography over silica gel (gradient ethyl acetate in cyclohexane) to afford the desired product (0.95 g). LCMS (method 1): m/z 635/637 $[M+H]^+$, retention time 1.26 min. $^1H$ NMR (400 MHz, DMSO-$d_6$) δ ppm: 9.15 (s, 1H), 8.88 (s, 1H), 8.57 (br s, 1H), 7.72 (br d, 1 h), 7.64 (br d, 1H), 5.38 (br s, 2H), 4.36 (q, 2H), 3.68-3.80 (m, 2H), 1.29-1.40 (t, 6H), 1.27 (s, 9H).

Step 2: Preparation of ethyl 2-[[(6-bromo-3-ethylsulfonyl-imidazo[1,2-a]pyridin-2-yl)amino]methyl]-5-(trifluoromethyl)pyridine-3-carboxylate (Intermediate IV-2)

(IV-2)

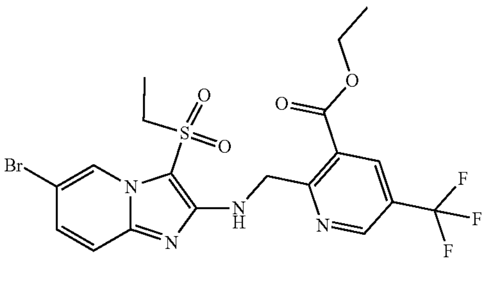

To a solution of ethyl 2-[[(6-bromo-3-ethylsulfonyl-imidazo[1,2-a]pyridin-2-yl)-tert-butoxycarbonyl-amino]methyl]-5-(trifluoromethyl)pyridine-3-carboxylate (intermediate IV-1 prepared as described above, 0.95 g, 1.50 mmol) in benzotrifluoride (4.8 mL) was added 2,2,2-trifluoroacetic acid (2.29 mL, 29.9 mmol). The reaction mixture was stirred at room temperature for 4 hours, then diluted with water and extracted with ethyl acetate. The organic phase was washed with an aqueous sodium bicarbonate solution, dried over sodium sulfate, filtered and concentrated under reduced pressure. The crude residue was purified by chromatography over silica gel (gradient ethyl acetate in cyclohexane) to afford the desired product (0.75 g). LCMS (method 1): m/z 535/537 $[M+H]^+$, retention time 1.18 min. $^1H$ NMR (400 MHz, DMSO-$d_6$) δ ppm: 9.14 (d, 1H), 8.60 (d, 1H), 8.52 (d, 1H), 7.61 (dd, 1H), 7.44 (d, 1H), 6.90 (br s, 1H), 5.13 (s, 2H), 4.41 (q, 2H), 3.43 (d, 2H), 1.39 (t, 3H), 1.13-1.23 (t, 3H).

Step 3: Preparation of 2-[[(6-bromo-3-ethylsulfonyl-imidazo[1,2-a]pyridin-2-yl)amino]methyl]-5-(trifluoromethyl)pyridine-3-carboxylic Acid (Intermediate IV-3)

(IV-3)

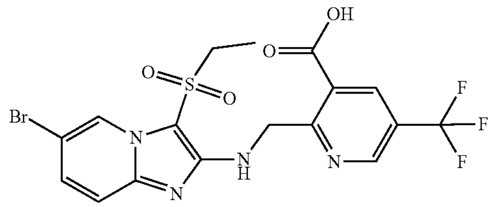

To a suspension of ethyl 2-[[(6-bromo-3-ethylsulfonyl-imidazo[1,2-a]pyridin-2-yl)amino]methyl]-5-(trifluoromethyl)pyridine-3-carboxylate (intermediate IV-2 prepared as described above, 0.90 g, 1.68 mmol) in methanol (18 mL) was added dihydroxybarium octahydrate (1.33 g, 4.20 mmol) in water (9 mL). The reaction mixture was stirred at room temperature for 18 hours, then concentrated under reduce pressure. To the residue was added water and the mixture was acidified with aqueous 2N hydrochloric acid. The formed precipitate was filtered and dried under reduce pressure to afford the desired product which was used without further purification (0.68 g). LCMS (method 1): m/z 507/509 $[M+H]^+$, retention time 1.01 min.

Step 4: Preparation of 6-(6-bromo-3-ethylsulfonyl-imidazo[1,2-a]pyridin-2-yl)-3-(trifluoromethyl)-7H-pyrrolo[3,4-b]pyridin-5-one (Compound P21)

(P21)

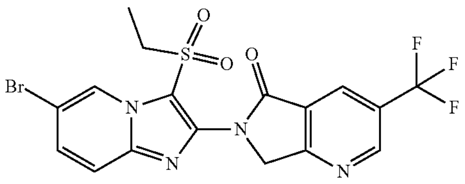

To a solution of 2-[[(6-bromo-3-ethylsulfonyl-imidazo[1,2-a]pyridin-2-yl)amino]methyl]-5-(trifluoromethyl)pyridine-3-carboxylic acid (intermediate IV-3 prepared as described above, 4.3 g, 8.5 mmol) in pyridine (22 mL) was added phosphorus oxychloride (1.6 mL, 17 mmol) at 0° C., and the mixture stirred at room temperature for 10 minutes. To the reaction mixture was added water, it was acidified with aqueous 1N hydrochloric acid, and the product extracted three times with ethyl acetate. The combined organic phases were dried on sodium sulfate, filtered and concentrated under reduced pressure. The crude residue was purified by chromatography over silica gel (gradient ethyl acetate in cyclohexane). The purified product was dissolved in acetonitrile and water was added. The precipitate formed was filtered and dried to afford the desired product (2.6 g). LCMS (method 1): m/z 489/491 $[M+H]^+$, retention time 1.11 min. $^1H$ NMR (400 MHz, DMSO-$d_6$) δ ppm: 9.32 (d, 1H), 8.97 (t, 1H), 8.74 (d, 1H), 7.87 (d, 2H), 5.26 (s, 2H), 3.89 (q, 2H), 1.35 (t, 3H).

Step 5: Preparation of tert-butyl N-[3-ethylsulfonyl-2-[5-oxo-3-(trifluoromethyl)-7H-pyrrolo[3,4-b]pyridin-6-yl]imidazo[1,2-a]pyridin-6-yl]carbamate (Intermediate IV-4)

(IV-4)

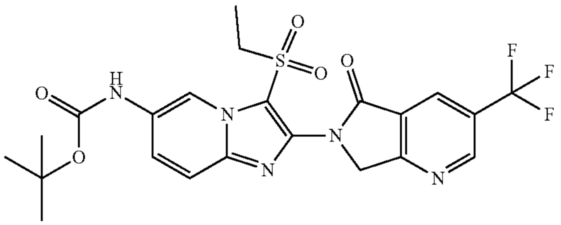

To a solution of 6-(6-bromo-3-ethylsulfonyl-imidazo[1,2-a]pyridin-2-yl)-3-(trifluoromethyl)-7H-pyrrolo[3,4-b]pyridin-5-one (compound P21 prepared as described above, 0.5 g, 1.02 mmol) in toluene (5 mL) were added tert-butyl carbamate (0.14 g, 1.23 mmol) and dicyclohexyl-[2-(2,4,6-triisopropylphenyl)phenyl]phosphane (0.58 g, 1.23 mmol). The mixture was degassed with argon, then cesium carbonate (0.54 g, 1.64 mmol) and palladium diacetate (23 mg, 0.10 mmol) were added. The reaction mixture was stirred at 110° C. for 2 hours. After cooling, the reaction mixture was poured into water and the product extracted three times with ethyl acetate. The combined organic layers were dried over sodium sulfate, filtered through a pad of Celite, and the filtrate concentrated under reduced pressure. The crude residue was purified by chromatography over silica gel (gradient ethyl acetate in cyclohexane) to afford the desired product (0.12 g). LCMS (method 1): m/z 526 $[M+H]^+$, retention time 1.10 min.

Step 6: Preparation of 6-(6-amino-3-ethylsulfonyl-imidazo[1,2-a]pyridin-2-yl)-3-(trifluoromethyl)-7H-pyrrolo[3,4-b]pyridin-5-one (Intermediate IV-5)

(IV-5)

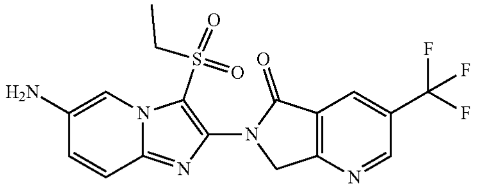

To a solution of tert-butyl N-[3-ethylsulfonyl-2-[5-oxo-3-(trifluoromethyl)-7H-pyrrolo[3,4-b]pyridin-6-yl]imidazo[1,2-a]pyridin-6-yl]carbamate (intermediate IV-4 prepared as described above, 0.12 g, 0.23 mmol) in benzotrifluoride (0.6 mL) was added 2,2,2-trifluoroacetic acid (0.35 mL, 4.57 mmol). The reaction mixture was stirred at room temperature for 16 hours, then diluted with water and the product extracted with ethyl acetate. The organic phase was washed with aqueous sodium bicarbonate solution, dried over sodium sulfate, filtered and concentrated under reduced pressure to afford the desired product (23 mg), which was used without further purification. LCMS (method 1): m/z 426 $[M+H]^+$, retention time 0.95 min.

Step 7: Preparation of N-[3-ethylsulfonyl-2-[5-oxo-3-(trifluoromethyl)-7H-pyrrolo[3,4-b]pyridin-6-yl]imidazo[1,2-a]pyridin-6-yl]acetamide (P36)

(P36)

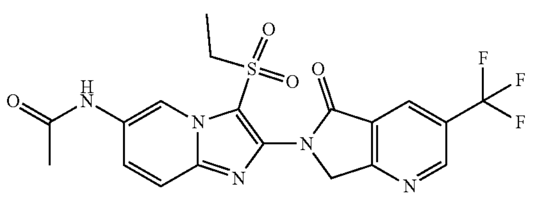

To a solution of 6-(6-amino-3-ethylsulfonyl-imidazo[1,2-a]pyridin-2-yl)-3-(trifluoromethyl)-7H-pyrrolo[3,4-b]pyridin-5-one (intermediate IV-5 prepared as described above, 23 mg, 0.054 mmol) in acetonitrile (0.23 mL) was added triethylamine (0.023 mL, 0.16 mmol). The solution was cooled to 0-5° C., then acetyl chloride (0.004 mL, 0.054 mmol) was added dropwise. The reaction mixture was stirred at 25° C. for 1 hour, diluted with water, and the product extracted with ethyl acetate. The organic phase was dried over sodium sulfate, filtered and concentrated under reduce pressure. The crude was purified by chromatography over silica gel (gradient ethyl acetate in cyclohexane) to afford the desired product (13 mg). LCMS (method 2): m/z 468 $[M+H]^+$, retention time 1.25 min. $^1H$ NMR (400 MHz, $CDCl_3$) δ ppm: 9.49 (s, 1H), 9.11 (s, 1H), 8.47 (s, 1H), 7.64 (d, 1H), 7.43-7.49 (m, 2H), 5.2 (s, 2H), 3.76 (q, 2H), 2.26 (s, 3H), 1.53 (t, 3H).

Example H5: Preparation of 2-[3-ethylsulfonyl-2-[1-oxo-6-(trifluoromethoxy)isoindolin-2-yl]imidazo[1,2-a]pyridin-6-yl]oxy-2-methyl-propanenitrile (Compound P26)

(P26)

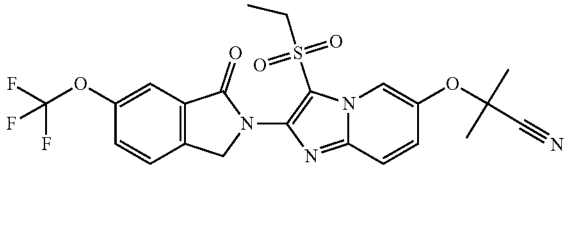

Step 1: Preparation of methyl 2-[[tert-butoxycarbonyl-(3-ethylsulfonyl-6-methoxy-imidazo[1,2-a]pyridin-2-yl)amino]methyl]-5-(trifluoromethoxy)benzoate (Intermediate V-1)

(V-1)

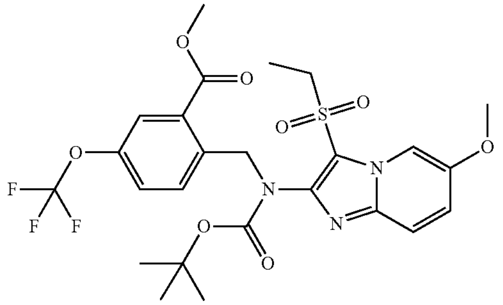

To a solution of tert-butyl N-(3-ethylsulfonyl-6-methoxy-imidazo[1,2-a]pyridin-2-yl)carbamate (intermediate IQ-5 prepared in analogy to intermediate III-7 described above, 1.0 g, 2.8 mmol) in acetonitrile (15.0 mL) was added cesium carbonate (1.4 g, 4.2 mmol). The reaction mixture was stirred at room temperature for 5 minutes, then a solution of methyl 2-(bromomethyl)-5-(trifluoromethoxy)-benzoate (prepared according to WO 20/174,094, 1.3 g, 4.2 mmol) in acetonitrile (2 mL) was added dropwise. The reaction mixture was stirred at 50° C. for 2 hours, allowed to cool, diluted with ice cold water, and the product was extracted twice with ethyl acetate. The combined organic layers were washed with water and brine, dried over sodium sulfate, filtered and concentrated under reduce pressure. The crude residue was purified by chromatography over silica gel (gradient ethyl acetate in cyclohexane) to afford the desired product (1.9 g). LCMS (method 1): m/z 588 $[M+H]^+$, retention time 1.24 min.

Step 2: Preparation of methyl 2-[[(3-ethylsulfonyl-6-methoxy-imidazo[1,2-a]pyridin-2-yl)amino]methyl]-5-(trifluoromethoxy)benzoate (Intermediate V-2)

(V-2)

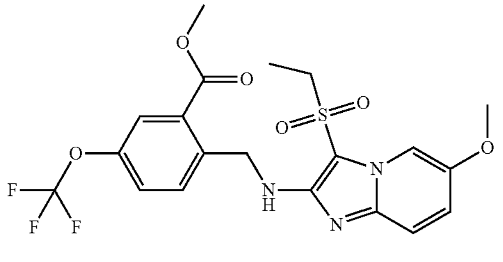

To a solution of methyl 2-[[tert-butoxycarbonyl-(3-ethylsulfonyl-6-methoxy-imidazo[1,2-a]pyridin-2-yl)amino]methyl]-5-(trifluoromethoxy)benzoate (intermediate V-1 prepared as described above, 1.9 g, 3.2 mmol) in benzotrifluoride (9.5 mL) was added 2,2,2-trifluoroacetic acid (4.9 mL, 65 mmol). The reaction mixture was stirred at room temperature for 4 hours, then diluted with water and extracted with ethyl acetate. The organic phase was washed with an aqueous sodium bicarbonate solution, dried over sodium sulfate, filtered and concentrated under reduced pressure. The crude residue was purified by chromatography over silica gel (gradient ethyl acetate in cyclohexane) to afford the desired product (0.75 g). LCMS (method 1): m/z 488 $[M+H]^+$, retention time 1.15 min. $^1H$ NMR (400 MHz, DMSO-$d_6$) δ ppm: 8.06 (d, 1H), 7.73-7.8 (m, 1H), 7.65 (d, 1H), 7.59 (br d, 1H), 7.39 (d, 1H), 7.27 (dd, 1H), 6.61 (br t, 1H), 4.85 (br d, 2H), 3.91 (s, 3H), 3.83 (m, 3H), 3.30-3.42 (m, 2H), 1.09 (t, 3H).

Step 3: Preparation of 2-[[(3-ethylsulfonyl-6-methoxy-imidazo[1,2-a]pyridin-2-yl)amino]methyl]-5-(trifluoromethoxy)benzoic Acid (Intermediate V-3)

(V-3)

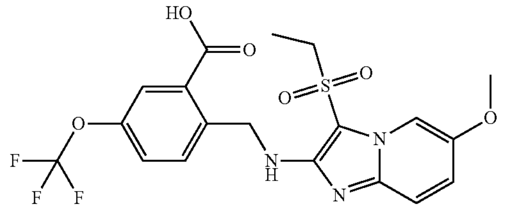

To a suspension of methyl 2-[[(3-ethylsulfonyl-6-methoxy-imidazo[1,2-a]pyridin-2-yl)amino]methyl]-5-(trifluoromethoxy)benzoate (intermediate V-2 prepared as described above, 1.0 g, 2.1 mmol) in methanol (20 mL) was added dihydroxybarium octahydrate (1.6 g, 5.1 mmol) in water (10 mL). The reaction mixture was stirred at room temperature for 18 hours, then concentrated under reduce pressure. To the residue was added water, then the mixture was acidified with aqueous 2N hydrochloric acid, and the formed precipitate filtered and dried under reduce pressure to afford the desired product which was used without further purification (0.84 g). LCMS (method 1): m/z 474 $[M+H]^+$, retention time 1.10 min.

Step 4: Preparation of 2-(3-ethylsulfonyl-6-methoxy-imidazo[1,2-a]pyridin-2-yl)-6-(trifluoromethoxy)isoindolin-1-one (Intermediate V-4)

(V-4)

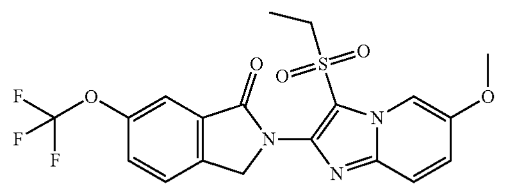

To a solution of 2-[[(3-ethylsulfonyl-6-methoxy-imidazo[1,2-a]pyridin-2-yl)amino]methyl]-5-(trifluoromethoxy)benzoic acid (intermediate V-3 prepared as described above, 0.9 g, 1.90 mmol) in pyridine (4.5 mL) was added phosphorus oxychloride (0.36 mL, 3.8 mmol, 2 equiv.) at 0° C. The mixture was stirred at room temperature for 10 minutes, quenched by addition of water, acidified with aqueous 1N hydrochloric acid, and the product extracted three times with ethyl acetate. The combined organic phases were dried on sodium sulfate, filtered and concentrated under reduced pressure. The crude residue was purified by chromatography over silica gel (gradient ethyl acetate in cyclohexane). The purified product was dissolved in acetonitrile and water was added. The precipitate formed was filtered and dried to afford the desired product (0.7 g). LCMS (method 2): m/z 456 $[M+H]^+$, retention time 1.48 min. $^1H$ NMR (400 MHz, DMSO-$d_6$) δ ppm: 8.35 (d, 1H), 7.87 (d, 1H), 7.74-7.82 (m, 3H), 7.52 (dd, 1H), 5.08 (s, 2H), 3.90 (s, 3H), 3.82 (q, 2H), 1.34 (t, 3H).

Step 5: Preparation of 2-(3-ethylsulfonyl-6-hydroxy-imidazo[1,2-a]pyridin-2-yl)-6-(trifluoromethoxy)isoindolin-1-one (Intermediate V-5)

(V-5)

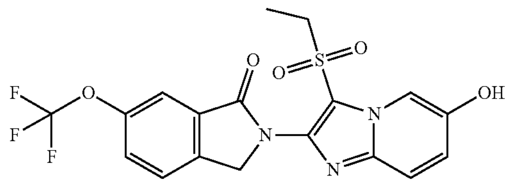

To 2-(3-ethylsulfonyl-6-methoxy-imidazo[1,2-a]pyridin-2-yl)-6-(trifluoromethoxy)isoindolin-1-one (intermediate V-4 prepared as described above, 0.65 g, 1.43 mmol) was added a solution of tribromoborane 1 M in dichloromethane (14.3 mL, 14.3 mmol) at 0° C. and the reaction mixture was stirred at room temperature for 2 hours. The mixture was slowly poured into ice and extracted with ethyl acetate twice. The combined organic layers were washed with brine, dried over sodium sulfate, filtered and concentrated under reduce pressure. The crude residue was purified by chromatography over silica gel (gradient ethyl acetate in cyclohexane) to afford the desired product (0.59 g). LCMS (method 2): m/z 442 $[M+H]^+$, retention time 1.43 min. $^1H$ NMR (400 MHz, DMSO-$d_6$) δ ppm: 10.22 (s, 1H), 8.4 (d, 1H), 7.86 (d, 1H), 7.70-7.80 (m, 3H), 7.37 (dd, 1H), 5.05 (s, 2H), 3.73 (q, 2H), 1.32 (t, 3H).

Similarly, 6-(3-ethylsulfonyl-6-hydroxy-imidazo[1,2-a]pyridin-2-yl)-3-(trifluoromethyl)-7H-pyrrolo[3,4-b]pyridin-5-one (V-5-a) can be prepared:

(V-5-a)

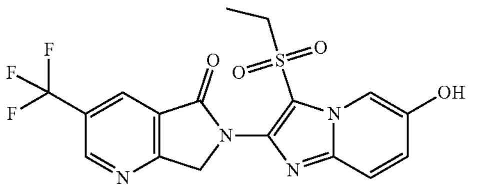

LCMS (method 1): m/z 427 $[M+H]^+$, retention time 0.99 min. $^1H$ NMR (400 MHz, $CDCl_3$) δ/ppm: 1.31 (t, 3H), 3.72 (q, 2H), 5.19 (s, 2H), 7.38 (dd, 1H), 7.74 (d, 1H), 8.39 (d, 1H), 8.71 (d, 1H), 9.32 (d, 1H), 10.26 (s, 1H).

Step 6: Preparation of 2-[3-ethylsulfonyl-2-[1-oxo-6-(trifluoromethoxy)isoindolin-2-yl]imidazo[1,2-a]pyridin-6-yl]ox-2-methyl-propanamide (Intermediate V-6)

(V-6)

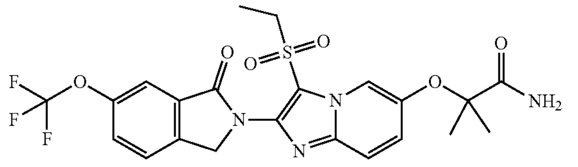

To a solution of 2-(3-ethylsulfonyl-6-hydroxy-imidazo[1,2-a]pyridin-2-yl)-6-(trifluoromethoxy)isoindolin-1-one (intermediate V-5 prepared as described above, 0.58 g, 1.31 mmol) in acetonitrile (12.0 mL) was added cesium carbonate (0.86 g, 2.63 mmol). The reaction mixture was stirred at room temperature for 5 minutes, then 2-bromo-2-methyl-propanamide (0.44 g, 2.63 mmol) was added, and stirring continued at 60° C. for 12 hours. The mixture was concentrated under reduce pressure and taken up with water and ethyl acetate. The organic layer was washed with brine, dried over sodium sulfate, filtered and concentrated under reduce pressure. The crude residue was purified by chromatography over silica gel (gradient ethyl acetate in cyclohexane) to afford the desired product (0.32 g). LCMS (method 2): m/z 527 $[M+H]^+$, retention time 1.40 min. $^1H$ NMR (400 MHz, DMSO-$d_6$) δ ppm: 8.51 (d, 1H), 7.87 (d, 1H), 7.76-7.83 (m, 3H), 7.73 (s, 1H), 7.51 (dd, 1H), 7.42 (s, 1H), 5.09 (s, 2H), 3.76 (q, 2H), 1.49 (s, 6H), 1.34 (t, 3H).

Similarly, 2-[3-ethylsulfonyl-2-[5-oxo-3-(trifluoromethyl)-7H-pyrrolo[3,4-b]pyridin-6-yl]imidazo[1,2-a]pyridin-6-yl]oxy-2-methyl-propanamide (V-6-a) can be prepared:

(V-6-a)

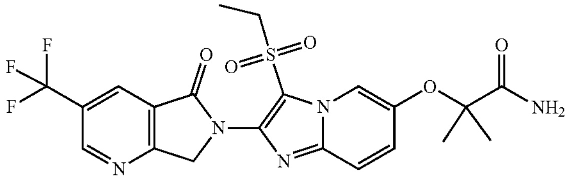

LCMS (method 1): m/z 512 $[M+H]^+$, retention time 1.02 min.

Step 7: Preparation of 2-[3-ethylsulfonyl-2-[1-oxo-6-(trifluoromethoxy)isoindolin-2-yl]imidazo[1,2-a]pyridin-6-yl]oxy-2-methyl-propanenitrile (Compound P26)

(P26)

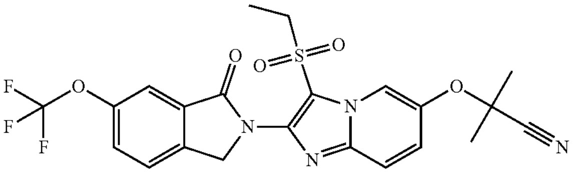

To a solution of 2-[3-ethylsulfonyl-2-[1-oxo-6-(trifluoromethoxy)isoindolin-2-yl]imidazo[1,2-a]pyridin-6-yl]oxy-2-methyl-propanamide (intermediate V-6 prepared as described above, 0.32 g, 0.61 mmol) in tetrahydrofuran was added triethylamine (2.43 mmol, 4 equiv.) at 0° C., followed by trifluoroacetic anhydride (2.43 mmol, 4 equiv.) dropwise, at 0° C. The reaction mixture was stirred at room temperature for 3 hours, then carefully quenched and basified with an aqueous sodium bicarbonate solution. The aqueous phase was extracted with ethyl acetate twice. The combined organic layers were washed with brine, dried over sodium sulfate, filtered and concentrated under reduce pressure. The crude residue was purified by chromatography over silica gel (gradient ethyl acetate in cyclohexane) to afford the desired product (0.25 g). LCMS (method 2): m/z 509 $[M+H]^+$, retention time 1.52 min. $^1H$ NMR (400 MHz, $CDCl_3$) δ ppm: 8.89 (s, 1H), 7.82 (s, 1H), 7.70 (d, 1H), 7.61 (d, 1H), 7.51 (br d, 2H), 5.10 (s, 2H), 3.83 (q, 2H), 1.82 (s, 6H), 1.52 (t, 3H).

Example H6: Preparation of 2-[3-ethylsulfonyl-2-[5-oxo-3-(trifluoromethyl)-7H-pyrrolo[3,4-b]pyridin-6-yl]imidazo[1,2-a]pyridin-6-yl]-2-methyl-propanenitrile (Compound P35)

(P35)

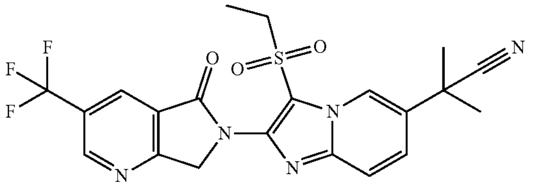

Step 1: Preparation of 2-(6-chloro-3-pyridyl)-2-methyl-propanenitrile (Intermediate VI-1)

(VI-1)

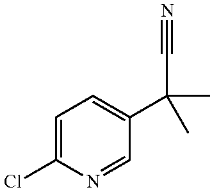

To a solution of 2-(6-chloro-3-pyridyl)acetonitrile (5.00 g, 33.0 mmol) in tetrahydrofuran (50 mL) was added sodium hydride (60% mass in oil) (3.30 g, 82.0 mmol) at 0° C. The reaction mixture was stirred at 0° C. for 15 minutes, then iodomethane (5.10 mL, 82 mmol) was added at 0° C. The reaction mixture stirred at room temperature for 2 hours, diluted with ice cold water and the product extracted three times with ethyl acetate. The combined organic layers were dried over sodium sulfate, filtered and concentrated under reduced pressure. The crude residue was used without further purification. This reaction was done on 6 batches to afford the desired product (35.0 g). LCMS (method 1): m/z 180 $[M+H]^+$, retention time 0.99 min. $^1H$ NMR (400 MHz, $CDCl_3$) δ ppm: 1.77 (s, 6H), 7.38 (d, 1H), 7.78 (dd, 1H), 8.52 (d, 1H).

Step 2: Preparation of 2-(6-chloro-3-pyridyl)-2-methyl-propanenitrile tert-butyl N-[5-(1-cyano-1-methyl-ethyl)-2-pyridyl]carbamate (Intermediate VI-2)

(VI-2)

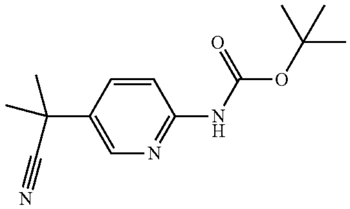

To a solution of 2-(6-chloro-3-pyridyl)-2-methyl-propanenitrile (intermediate VI-1 prepared as described above, 20.0 g, 110 mmol) in 1,4-dioxane (400 mL) were added tert-butyl carbamate (19.5 g, 166 mmol) and cesium carbonate (54.2 g, 166 mmol). The reaction mixture was purged with argon for 15 minutes, then 2-dicyclohexylphosphino-2',4',6'-triisopropylbiphenyl (X-Phos, 16.2 g, 33.2 mmol) and palladium(II) acetate (3.73 g, 16.7 mmol) were added and the reaction mixture was stirred at 110° C. for 3 hours. After cooling to room temperature, the mixture was diluted with cold water and the product extracted three times with ethyl acetate. The combined organic layers were dried over sodium sulfate, filtered and concentrated under reduced pressure. The crude residue was used without further purification (30.0 g). LCMS (method 1): m/z 262 $[M+H]^+$, retention time 1.08 min.

Step 3: Preparation 2-(6-amino-3-pyridyl)-2-methyl-propanenitrile (Intermediate VI-3)

(VI-3)

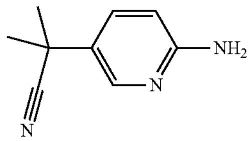

To a solution of tert-butyl N-[5-(1-cyano-1-methyl-ethyl)-2-pyridyl]carbamate (intermediate VI-2 prepared as described above, 28.0 g, 107 mmol) in benzotrifluoride (140 mL) was added 2,2,2-trifluoroacetic acid (164 mL, 2143 mmol). The reaction mixture was stirred at room temperature for 16 hours, then diluted with water and the product extracted with ethyl acetate. The organic phase was washed with an aqueous sodium bicarbonate solution, dried over sodium sulfate, filtered and concentrated under reduced pressure. The crude residue was purified by chromatography over silica gel (gradient ethyl acetate in cyclohexane) to afford the desired product (21.0 g). LCMS (method 1): m/z 162 $[M+H]^+$, retention time 0.17 min. $^1H$ NMR (400 MHz, $CDCl_3$) δ ppm: 1.72 (s, 6H), 6.92 (d, 1H), 7.80 (d, 1H), 7.88 (dd, 1H).

Step 4: Preparation ethyl 6-(1-cyano-1-methyl-ethyl)imidazo[1,2-a]pyridine-2-carboxylate (Intermediate VI-4)

(VI-4)

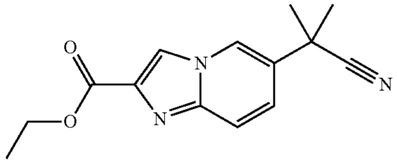

To a solution of 2-(6-amino-3-pyridyl)-2-methyl-propanenitrile (intermediate VI-3 prepared as described above, 15.0 g, 93.1 mmol) in ethanol (150 mL) were added $NaHCO_3$ (15.6 g, 186 mmol) and ethyl 3-bromo-pyruvate (40.3 g, 186 mmol). The reaction mixture was stirred at 85° C. for 4 hours, then allowed to cool to room temperature. The mixture was diluted with cold water and the product extracted with ethyl acetate. The organic phase was washed with an aqueous sodium bicarbonate solution, dried over sodium sulfate, filtered and concentrated under reduced pressure. The crude residue was purified by chromatography over silica gel (gradient ethyl acetate in cyclohexane) to afford the desired product (13.2 g). LCMS (method 1): m/z 258 $[M+H]^+$, retention time 1.08 min. $^1H$ NMR (400 MHz, $CDCl_3$) δ ppm: 1.43 (t, 3H), 1.78 (s, 6H), 4.46 (q, 2H), 7.24-7.31 (m, 1H), 7.72 (d, 1H), 8.21 (s, 1H), 8.30-8.33 (m, 1H).

Step 5: Preparation ethyl 3-chloro-6-(1-cyano-1-methyl-ethyl)imidazo[1,2-a]pyridine-2-carboxylate (Intermediate VI-5)

(VI-5)

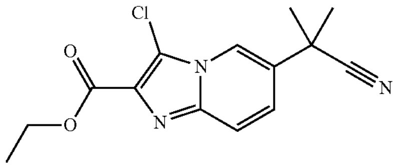

To a solution of ethyl 6-(1-cyano-1-methyl-ethyl)imidazo[1,2-a]pyridine-2-carboxylate (intermediate VI-4 prepared as described above, 13.2 g, 51.3 mmol) in acetonitrile (264 mL) was added N-chlorosuccinimide (8.22 g, 61.6 mmol). The reaction mixture was stirred at 50° C. for 4 hours. The reaction mixture was diluted with cold water and extracted with ethyl acetate. The organic phase was washed with an aqueous sodium bicarbonate solution, dried over sodium sulfate, filtered and concentrated under reduced pressure. The crude residue was used without further purification (11.0 g). LCMS (method 1): m/z 292 $[M+H]^+$, retention time 1.31 min. $^1H$ NMR (400 MHz, $CDCl_3$) δ ppm: 1.48 (t, 3H), 1.84 (s, 6H), 4.52 (q, 2H), 7.50 (dd, 1H), 7.90 (d, 1H), 8.31 (m, 1H).

Step 6: Preparation ethyl 6-(1-cyano-1-methyl-ethyl)-3-ethylsulfanyl-imidazo[1,2-a]pyridine-2-carboxylate (Intermediate VI-6)

(VI-6)

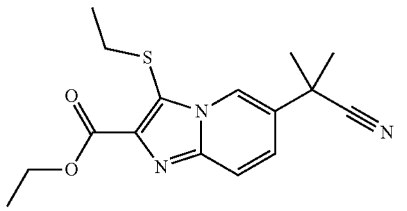

To a solution of ethyl 3-chloro-6-(1-cyano-1-methyl-ethyl)imidazo[1,2-a]pyridine-2-carboxylate (intermediate VI-5 prepared as described above, 11.0 g, 37.7 mmol) in dimethylsulfoxide (110 mL) was added sodium ethanethiolate (6.34 g, 75.4 mmol) portionwise. The reaction mixture was stirred at room temperature for 1 hour, then it was diluted with cold water and the formed precipitate filtered and dried to afford the desired product (8.00 g). LCMS (method 1): m/z 318 $[M+H]^+$, retention time 1.07 min. $^1H$ NMR (400 MHz, $CDCl_3$) δ ppm: 1.21 (t, 3H), 1.47 (t, 3H), 1.82 (s, 6H), 2.97 (q, 2H), 4.50 (q, 2H), 7.40 (s, 1H), 7.74 (d, 1H), 8.69 (d, 1H). LCMS (method 1): m/z 318 $[M+H]^+$, retention time 1.07 min.

Step 7: Preparation of ethyl 6-(1-cyano-1-methyl-ethyl)-3-ethylsulfonyl-imidazo[1,2-a]pyridine-2-carboxylate (Intermediate VI-7)

(VI-7)

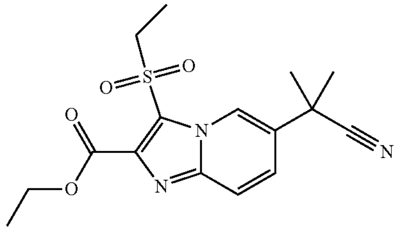

To a solution of ethyl 6-(1-cyano-1-methyl-ethyl)-3-ethylsulfanyl-imidazo[1,2-a]pyridine-2-carboxylate (intermediate VI-6 prepared as described above, 8.00 g, 25.0 mmol) in trifluoromethylbenzene (120 mL) was added 3-chlorobenzenecarboperoxoic acid (16.0 g, 63.0 mmol) portionwise. The reaction mixture was stirred at room temperature for 24 hours. After dilution with an aqueous saturated sodium bicarbonate solution, the formed precipitate was filtered and dried. The crude residue was purified by chromatography over silica gel (gradient ethyl acetate in cyclohexane) to afford the desired product (6.70 g). LCMS (method 1): m/z 350 $[M+H]^+$, retention time 1.01 min. $^1H$ NMR (400 MHz, $CDCl_3$) δ ppm: 1.40 (t, 3H), 1.49 (t, 3H), 1.83 (s, 6H), 3.76 (q, 2H), 4.54 (q, 2H), 7.66 (dd, 1H), 7.89 (d, 1H), 9.41 (d, 1H).

Step 8: Preparation of 6-(1-cyano-1-methyl-ethyl)-3-ethylsulfonyl-imidazo[1,2-a]pyridine-2-carboxylic Acid (Intermediate VI-8)

(VI-8)

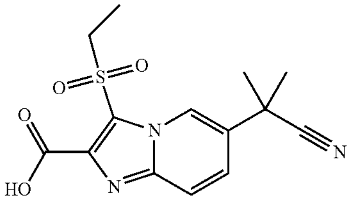

To a solution of ethyl 6-(1-cyano-1-methyl-ethyl)-3-ethylsulfonyl-imidazo[1,2-a]pyridine-2-carboxylate (intermediate VI-7 prepared as described above, 6.7 g, 19.0 mmol) in tetrahydrofuran (67 mL) and water (27 mL) was added lithium hydroxide (1.60 g, 38.0 mmol) in water (32 mL) portionwise at 0-5° C. The reaction mixture was stirred at room temperature for 5 hours, then acidified with aqueous 2N hydrochloric acid, diluted with water and the product extracted with ethyl acetate. The organic phase was dried over sodium sulfate, filtered and concentrated under reduced pressure. The crude residue was used without further purification (5.30 g). LCMS (method 1): m/z 322 $[M+H]^+$, retention time 0.89 min. $^1H$ NMR (400 MHz, DMSO-$d_6$) δ ppm: 1.25 (t, 3H), 1.78 (s, 6H), 3.72 (q, 2H), 7.89 (dd, 1H), 7.96 (d, 1H), 9.12 (s, 1H), 13.79-14.02 (m, 1H).

Step 9: Preparation of tert-butyl N-[6-(1-cyano-1-methyl-ethyl)-3-ethylsulfonyl-imidazo[1,2-a]pyridin-2-yl]carbamate (Intermediate VI-9)

(VI-9)

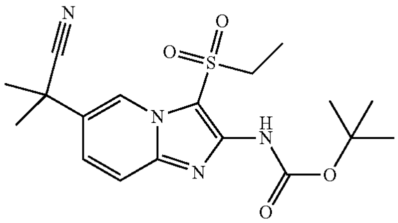

To a solution of 6-(1-cyano-1-methyl-ethyl)-3-ethylsulfonyl-imidazo[1,2-a]pyridine-2-carboxylic acid (intermediate VI-8 prepared as described above, 5.30 g, 16.0 mmol) in tert-butanol (27 mL) and toluene (53 mL) were added triethylamine (3.00 mL, 21.0 mmol), followed by diphenylphosphoryl azide (4.70 mL, 21.0 mmol) dropwise. The reaction mixture was stirred at 80° C. for 30 minutes, then cooled to room temperature. The mixture was diluted with ice and the product extracted with ethyl acetate, the organic phase dried over sodium sulfate, filtered and concentrated under reduced pressure. The crude residue was purified by chromatography over silica gel (gradient ethyl acetate in cyclohexane) to afford the desired product (1.80 g). LCMS (method 1): m/z 393 $[M+H]^+$, retention time 1.04 min. $^1H$ NMR (400 MHz, DMSO-$d_6$) δ ppm: 1.26 (t, 3H), 1.47 (s, 9H), 1.77 (s, 6H), 3.65 (q, 2H), 7.77-7.84 (m, 2H), 8.79 (s, 1H), 9.40 (s, 1H).

Step 10: Preparation of ethyl 2-[[tert-butoxycarbonyl-[6-(1-cyano-1-methyl-ethyl)-3-ethylsulfonyl-imidazo[1,2-a]pyridin-2-yl]amino]methyl]-5-(trifluoromethyl)pyridine-3-carboxylate (Intermediate VI-10)

(VI-10)

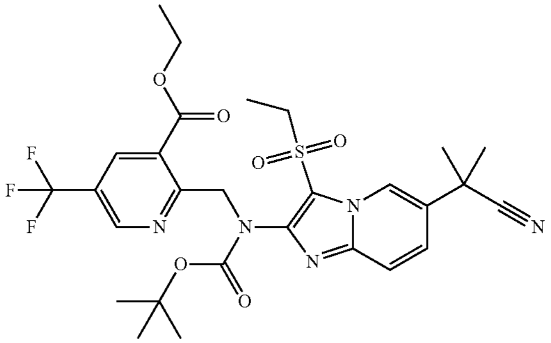

To a solution of tert-butyl N-[6-(1-cyano-1-methyl-ethyl)-3-ethylsulfonyl-imidazo[1,2-a]pyridin-2-yl]carbamate (intermediate VI-9 prepared as described above, 0.50 g, 1.27 mmol) in acetonitrile (7.50 mL) were added cesium carbonate (0.63 g, 1.91 mmol), followed by a solution of ethyl 2-(bromomethyl)-5-(trifluoromethyl)pyridine-3-carboxylate (intermediate II-4-a prepared in analogy to intermediate II-4 described above, 0.52 g, 1.66 mmol) in acetonitrile (7.50 mL) dropwise. The reaction mixture was heated to 50° C. and stirred for 2 hours. After cooling to room temperature, it was diluted with water and the product extracted three times with ethyl acetate. The combined organic layers were washed with water and brine, dried over sodium sulfate, filtered and concentrated under reduced pressure. The crude residue was used without further purification (0.60 g). LCMS (method 1): m/z 624 $[M+H]^+$, retention time 1.52 min.

Step 11: Preparation of ethyl 2-[[[6-(1-cyano-1-methyl-ethyl)-3-ethylsulfonyl-imidazo[1,2-a]pyridin-2-yl]amino]methyl]-5-(trifluoromethyl)pyridine-3-carboxylate (Intermediate VI-11)

(VI-11)

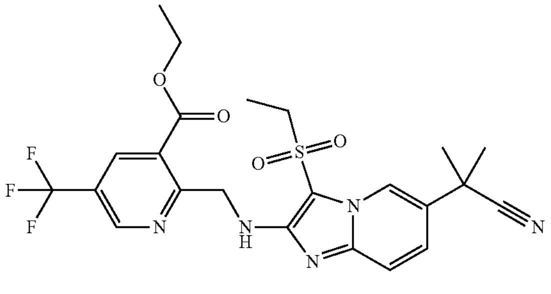

To a solution of ethyl 2-[[tert-butoxycarbonyl-[6-(1-cyano-1-methyl-ethyl)-3-ethylsulfonyl-imidazo[1,2-a]pyridin-2-yl]amino]methyl]-5-(trifluoromethyl)pyridine-3-carboxylate (intermediate VI-10 prepared as described above, 0.60 g, 0.96 mmol) in benzotrifluoride (3.00 mL) was added 2,2,2-trifluoroacetic acid (1.47 mL, 19.2 mmol). The reaction mixture was stirred at room temperature for 16 hours, then diluted with water and the product extracted with ethyl acetate. The combined organic layers were washed with an aqueous saturated sodium bicarbonate solution, dried over sodium sulfate, filtered and concentrated under reduced pressure. The crude residue was used without further purification (0.48 g). LCMS (method 1): m/z 524 $[M+H]^+$, retention time 1.12 min. $^1H$ NMR (400 MHz, DMSO-$d_6$) δ ppm: 1.18 (t, 3H), 1.39 (t, 3H), 1.74 (s, 6H), 3.41 (q, 2H), 4.42 (q, 2H), 5.14 (br d, 2H), 6.90 (br t, 1H), 7.53 (d, 1H), 7.67 (dd, 1H), 8.53 (d, 1H), 8.56 (d, 1H), 9.13 (m, 1H).

Step 12: Preparation of 2-[[[6-(1-cyano-1-methyl-ethyl)-3-ethylsulfonyl-imidazo[1,2-a]pyridin-2-yl]amino]methyl]-5-(trifluoromethyl)pyridine-3-carboxylic Acid (Intermediate VI-12)

(VI-12)

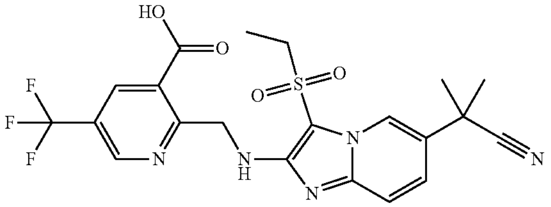

To a solution of ethyl 2-[[[6-(1-cyano-1-methyl-ethyl)-3-ethylsulfonyl-imidazo[1,2-a]pyridin-2-yl]amino]methyl]-5-(trifluoromethyl)pyridine-3-carboxylate (intermediate VI-11 prepared as described above, 0.48 g, 0.92 mmol) in methanol (9.60 mL) was added dihydroxybarium octahydrate (0.72 g, 2.29 mmol) dissolved in water (4.8 mL). The reaction mixture was stirred at room temperature for 4 hours, then the volatiles were removed under reduced pressure. The residue was acidified with aqueous 2N hydrochloric acid, the formed precipitate filtered and dried to afford the desired product (0.41 g). LCMS (method 1): m/z 496 $[M+H]^+$, retention time 1.02 min. $^1H$ NMR (400 MHz, DMSO-$d_6$) δ ppm: 1.18 (t, 3H), 1.74 (s, 6H), 3.42 (q, 2H), 5.16 (br d, 2H), 6.98 (t, 1H), 7.55 (d, 1H), 7.67 (dd, 1H), 8.52 (d, 1H), 8.57 (s, 1H), 9.11-9.13 (m, 1H).

Step 13: Preparation of 2-[3-ethylsulfonyl-2-[5-oxo-3-(trifluoromethyl)-7H-pyrrolo[3,4-b]pyridin-6-yl]imidazo[1,2-a]pyridin-6-yl]-2-methyl-propanenitrile (P35)

(P35)

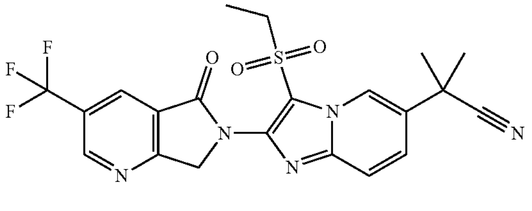

To a solution of 2-[[[6-(1-cyano-1-methyl-ethyl)-3-ethylsulfonyl-imidazo[1,2-a]pyridin-2-yl]amino]methyl]-5-(trifluoromethyl)pyridine-3-carboxylic acid (intermediate VI-12 prepared as described above, 0.40 g, 0.81 mmol) in pyridine (2.00 mL) was added phosphorus oxychloride (0.15 mL, 1.65 mmol) at 0° C. The reaction mixture was stirred at room temperature for 10 minutes, then diluted with water, acidified with aqueous 1N hydrochloric acid, and the product extracted three times with ethyl acetate. The combined organic layers were dried over sodium sulfate, filtered and concentrated under reduced pressure. Purification of the crude material by flash chromatography over silica gel (gradient ethyl acetate in cyclohexane) afforded the desired product (0.25 g). LCMS (method 1): m/z 478 $[M+H]^+$, retention time 1.04 min. $^1H$ NMR (400 MHz, $CDCl_3$) δ ppm: 1.55 (t, 3H), 1.86 (s, 6H), 3.83 (q, 2H), 5.23 (s, 2H), 7.66 (dd, 1H), 7.79 (d, 1H), 8.49 (s, 1H), 9.04 (s, 1H), 9.13 (s, 1H).

Example H7: Preparation of 6-[6-(2,2-difluoroethoxy)-3-ethylsulfonyl-imidazo[1,2-a]pyridin-2-yl]-3-(trifluoromethyl)-7H-pyrrolo[3,4-b]pyridin-5-one (Compound P19)

(P19)

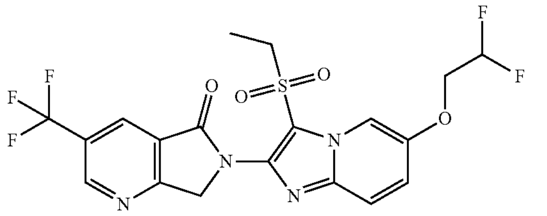

To a solution of 6-(3-ethylsulfonyl-6-hydroxy-imidazo[1,2-a]pyridin-2-yl)-3-(trifluoromethyl)-7H-pyrrolo[3,4-b]pyridin-5-one (intermediate V-5-a prepared as described above) (40 mg, 0.094 mmol) in acetonitrile (0.8 mL) were added potassium carbonate (3 equiv., 0.281 mmol) and 2,2-difluoroethyl trifluoromethanesulfonate (1.3 equiv., 0.122 mmol) at room temperature. The reaction mixture was stirred at room temperature overnight, then added to water (10 mL) and the product extracted twice with ethyl acetate (2×8 mL). The combined organic layers were washed with brine (10 mL), dried over sodium sulfate, filtered and concentrated under vacuum. The crude residue was purified by combiflash chromatography (50-60% ethyl acetate in cyclohexane) to afford the desired product (32 mg). LCMS (method 1): m/z 491 $[M+H]^+$, retention time 1.09 min.

Example H8: Preparation of 6-[6-(difluoromethoxy)-3-ethylsulfonyl-imidazo[1,2-a]pyridin-2-yl]-3-(trifluoromethyl)-7H-pyrrolo[3,4-b]pyridin-5-one (Compound P10)

(P10)

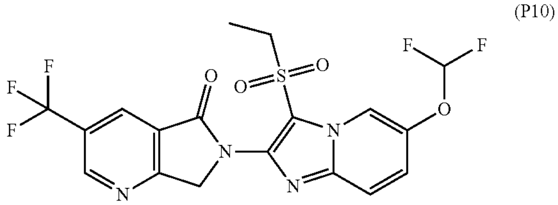 [SMILES: CCS(=O)(=O)c1c(N2Cc3ncc(C(F)(F)F)cc3C2=O)nc2ccc(OC(F)F)cn12]

To a solution of 6-(3-ethylsulfonyl-6-hydroxy-imidazo[1,2-a]pyridin-2-yl)-3-(trifluoromethyl)-7H-pyrrolo[3,4-b]pyridin-5-one (intermediate V-5-a prepared as described above) (0.1 g, 0.235 mmol) and potassium carbonate (1.5 equiv., 0.352 mmol) in N,N-dimethylformamide (3 mL) was added sodium 2-chloro-2,2-difluoro-acetate (2.0 equiv., 0.469 mmol). The reaction mixture was stirred at 60° C. for 5 hours, then diluted with water (20 mL) and the product extracted with ethyl acetate (3×10 mL). The combined organic layers were dried over sodium sulfate, filtered and concentrated under reduced pressure. The crude was purified by combiflash (silica gel, 30% ethyl acetate in cyclohexane) to afford the desired product (26 mg). LCMS (method 1): m/z 477 $[M+H]^+$, retention time 1.00 min.

Example H9: Preparation of 6-(7-cyclopropyl-3-ethylsulfonyl-imidazo[1,2-a]pyridin-2-yl)-3-(trifluoromethyl)-7H-pyrrolo[3,4-b]pyridin-5-one (Compound P24)

(P24)

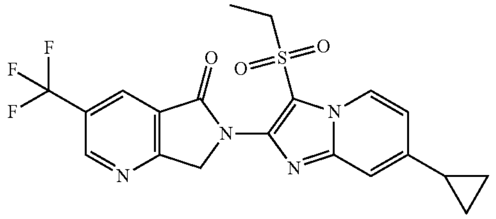

To 6-(7-bromo-3-ethylsulfonyl-imidazo[1,2-a]pyridin-2-yl)-3-(trifluoromethyl)-7H-pyrrolo[3,4-b]pyridin-5-one (compound P22) (240 mg, 0.40 mmol) in toluene (4 mL) and water (0.8 mL) were added potassium carbonate (3 equiv.), cyclopropylboronic acid (2 equiv.) and the solution was flushed with nitrogen for 10 minutes. 1,1'-Bis(diphenylphosphino)ferrocene-palladium(II)dichloride dichloromethane complex (0.05 equiv.) was added and the solution further flushed with nitrogen for 5 minutes, then heated in the microwave at 110° for 1.5 hours. After cooling to room temperature, the mixture was diluted with water and the product extracted three times with ethyl acetate. The combined organic layers were washed with brine, dried over sodium sulfate, filtered and concentrated under reduced pressure. The residue was purified by combiflash column chromatography (0-30% ethyl acetate in cyclohexane) to afford the desired product (133 mg) as a solid. LCMS (method 2): m/z 451 $[M+H]^+$, retention time 1.48 min.

TABLE P

Examples of compounds of formula (I)

| No. | IUPAC name | Structures | LCMS $R_t$ (min) | LCMS $[M + H]^+$ (measured) | LCMS Method | Mp (° C.) |
|---|---|---|---|---|---|---|
| P1 | 2-[3-ethylsulfonyl-6-(trifluoromethyl) benzothiophen-2-yl]-6-(trifluoromethyl)-3H-pyrrolo[3,4-c] pyridin-1-one | 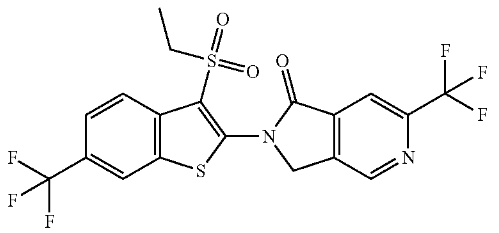 [SMILES: CCS(=O)(=O)c1c(N2Cc3cnc(C(F)(F)F)cc3C2=O)sc2cc(C(F)(F)F)ccc12] | 1.16 | 495 | 1 | — |
| P2 | 6-[3-ethylsulfonyl-7-(trifluoromethyl) imidazo[1,2-a] pyridin-2-yl]-3-(trifluoromethyl)-7H-pyrrolo[3,4-b] pyridin-5-one | 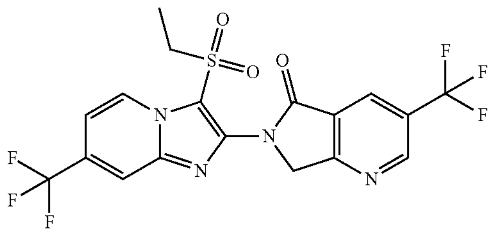 [SMILES: CCS(=O)(=O)c1c(N2Cc3ncc(C(F)(F)F)cc3C2=O)nc2cc(C(F)(F)F)ccn12] | 1.06 | 479 | 1 | 207-209 |
| P3 | 1-[3-ethylsulfonyl-2-[5-oxo-3-(trifluoromethyl)-7H-pyrrolo[3,4-b] pyridin-6-yl]imidazo [1,2-a]pyridin-7-yl] cyclopropane-carbonitrile | 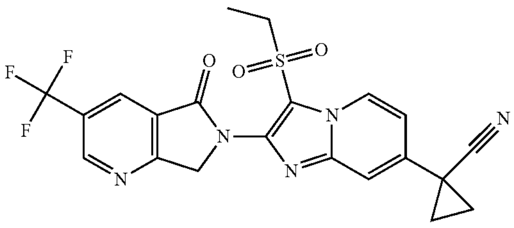 [SMILES: CCS(=O)(=O)c1c(N2Cc3ncc(C(F)(F)F)cc3C2=O)nc2cc(C3(C#N)CC3)ccn12] | 0.99 | 476 | 1 | 211-213 |
| P4 | 6-[3-ethylsulfonyl-6-(trifluoromethyl) imidazo[1,2-a] pyridin-2-yl]-3-(trifluoromethyl)-7H-pyrrolo[3,4-b] pyridin-5-one | 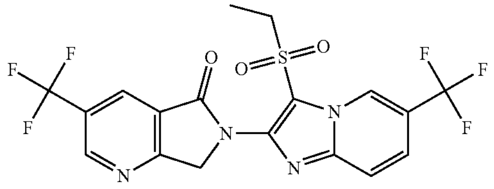 [SMILES: CCS(=O)(=O)c1c(N2Cc3ncc(C(F)(F)F)cc3C2=O)nc2ccc(C(F)(F)F)cn12] | 1.05 | 479 | 1 | 195-197 |
| P5 | 1-[3-ethylsulfonyl-2-[1-oxo-6-(trifluoromethoxy) isoindolin-2-yl] imidazo[1,2-a] pyridin-7-yl] cyclopropane-carbonitrile | 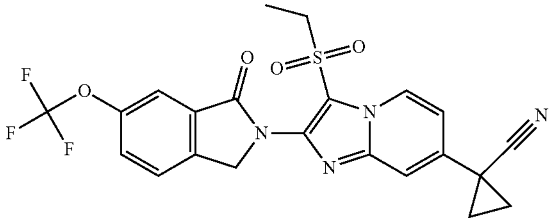 [SMILES: CCS(=O)(=O)c1c(N2Cc3ccc(OC(F)(F)F)cc3C2=O)nc2cc(C3(C#N)CC3)ccn12] | 1.06 | 491 | 1 | 189-191 |
| P6 | 2-[3-ethylsulfonyl-6-(trifluoromethyl) imidazo[1,2-a] pyridin-2-yl]-6-(trifluoromethoxy) isoindolin-1-one | 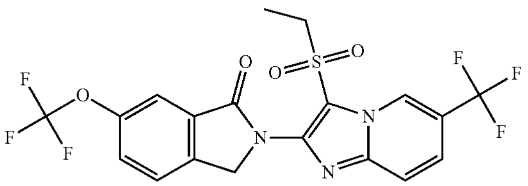 [SMILES: CCS(=O)(=O)c1c(N2Cc3ccc(OC(F)(F)F)cc3C2=O)nc2ccc(C(F)(F)F)cn12] | 1.12 | 494 | 1 | 158-160 |

TABLE P-continued

Examples of compounds of formula (I)

| No. | IUPAC name | Structures | LCMS $R_t$ (min) | LCMS $[M + H]^+$ (measured) | LCMS Method | Mp (° C.) |
|---|---|---|---|---|---|---|
| P7 | 2-[3-ethylsulfonyl-7-(trifluoromethyl) imidazo[1,2-a] pyridin-2-yl]-6-(trifluoromethoxy) isoindolin-1-one | 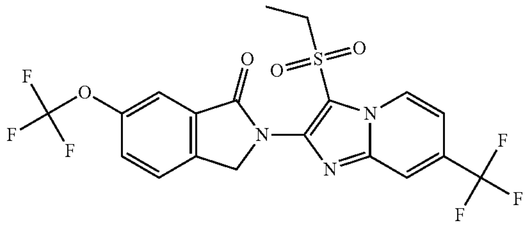 [SMILES: CCS(=O)(=O)c1c(N2Cc3ccc(OC(F)(F)F)cc3C2=O)nc2cc(C(F)(F)F)ccn12] | 1.13 | 494 | 1 | 198-200 |
| P8 | 6-(3-ethylsulfonyl-6-methoxy-imidazo [1,2-a]pyridin-2-yl)-3-(trifluoromethyl)-7H-pyrrolo[3,4-b] pyridin-5-one | 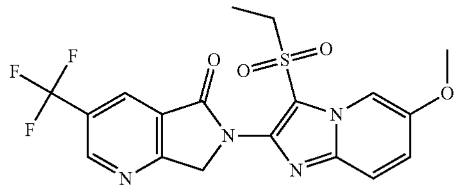 [SMILES: CCS(=O)(=O)c1c(N2Cc3ncc(C(F)(F)F)cc3C2=O)nc2ccc(OC)cn12] | 1.06 | 441 | 1 | 214-216 |
| P9 | 6-(3-ethylsulfonyl-6-isopropoxy-imidazo [1,2-a]pyridin-2-yl)-3-(trifluoromethyl)-7H-pyrrolo[3,4-b] pyridin-5-one | 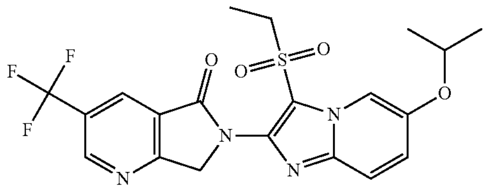 [SMILES: CCS(=O)(=O)c1c(N2Cc3ncc(C(F)(F)F)cc3C2=O)nc2ccc(OC(C)C)cn12] | 1.05 | 469 | 1 | 185-187 |
| P10 | 6-[6-(difluoromethoxy)-3-ethylsulfonyl-imidazo[1,2-a] pyridin-2-yl]-3-(trifluoromethyl)-7H-pyrrolo[3,4-b] pyridin-5-one | 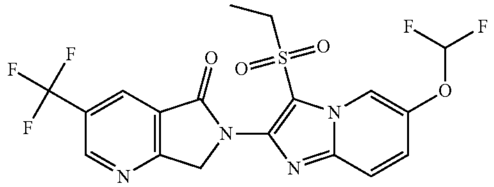 [SMILES: CCS(=O)(=O)c1c(N2Cc3ncc(C(F)(F)F)cc3C2=O)nc2ccc(OC(F)F)cn12] | 1.00 | 477 | 1 | 196-198 |
| P11 | 6-[3-ethylsulfonyl-6-(2,2,2-trifluoroethoxy) imidazo[1,2-a]pyridin-2-yl]-3-(trifluoromethyl)-7H-pyrrolo[3,4-b]pyridin-5-one | 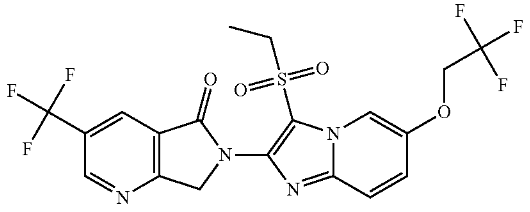 [SMILES: CCS(=O)(=O)c1c(N2Cc3ncc(C(F)(F)F)cc3C2=O)nc2ccc(OCC(F)(F)F)cn12] | 1.04 | 509 | 1 | 188-190 |
| P12 | 6-[3-ethylsulfonyl-7-(2,2,2-trifluoroethoxy) imidazo[1,2-a]pyridin-2-yl]-3-(trifluoromethyl)-7H-pyrrolo[3,4-b]pyridin-5-one | 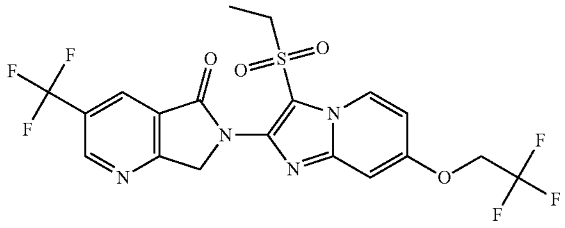 | 1.03 | 509 | 1 | 120-122 |
| P13 | 6-(3-ethylsulfonyl-7-methoxy-imidazo [1,2-a]pyridin-2-yl)-3-(trifluoromethyl)-7H-pyrrolo[3,4-b] pyridin-5-one | 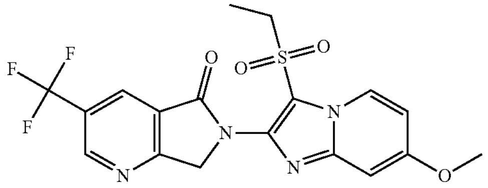 [SMILES: CCS(=O)(=O)c1c(N2Cc3ncc(C(F)(F)F)cc3C2=O)nc2cc(OC)ccn12] | 1.31 | 441 | 2 | 106-109 |

TABLE P-continued

Examples of compounds of formula (I)

| | | | LCMS | | | |
|---|---|---|---|---|---|---|
| No. | IUPAC name | Structures | $R_t$ (min) | $[M + H]^+$ (measured) | Method | Mp (° C.) |
| P14 | 1-[3-ethylsulfonyl-2-[1-oxo-6-(trifluoromethoxy)isoindolin-2-yl]imidazo[1,2-a]pyridin-6-yl]cyclopropane-carbonitrile | 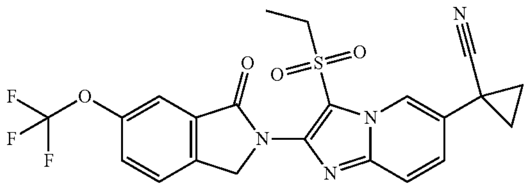 [SMILES: CCS(=O)(=O)c1c(N2Cc3ccc(OC(F)(F)F)cc3C2=O)nc2ccc(C3(C#N)CC3)cn12] | 1.04 | 491 | 1 | 90-92 |
| P15 | 1-[3-ethylsulfonyl-2-[5-oxo-3-(trifluoromethyl)-7H-pyrrolo[3,4-b]pyridin-6-yl]imidazo[1,2-a]pyridin-6-yl]cyclopropane-carbonitrile | 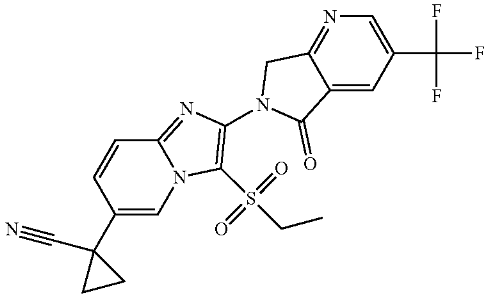 [SMILES: CCS(=O)(=O)c1c(N2Cc3ncc(C(F)(F)F)cc3C2=O)nc2ccc(C3(C#N)CC3)cn12] | 0.98 | 476 | 1 | 224-226 |
| P16 | 1-[3-ethylsulfonyl-2-[1-oxo-6-(trifluoromethyl)isoindolin-2-yl]imidazo[1,2-a]pyridin-6-yl]cyclopropane-carbonitrile | 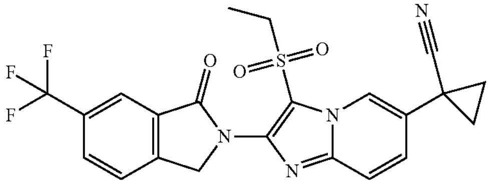 [SMILES: CCS(=O)(=O)c1c(N2Cc3ccc(C(F)(F)F)cc3C2=O)nc2ccc(C3(C#N)CC3)cn12] | 1.03 | 475 | 1 | 212-214 |
| P17 | 2-[6-(1,1-difluoroethyl)-3-ethylsulfonyl-imidazo[1,2-a]pyridin-2-yl]-6-(trifluoromethoxy)isoindolin-1-one | 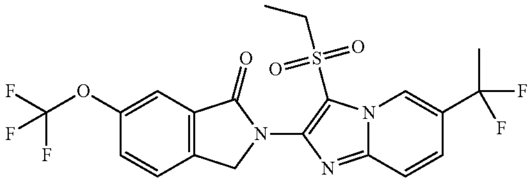 [SMILES: CCS(=O)(=O)c1c(N2Cc3ccc(OC(F)(F)F)cc3C2=O)nc2ccc(C(C)(F)F)cn12] | 1.09 | 490 | 1 | 164-166 |
| P18 | 6-[6-(1,1-difluoroethyl)-3-ethylsulfonyl-imidazo[1,2-a]pyridin-2-yl]-3-(trifluoromethyl)-7H-pyrrolo[3,4-b]pyridin-5-one | 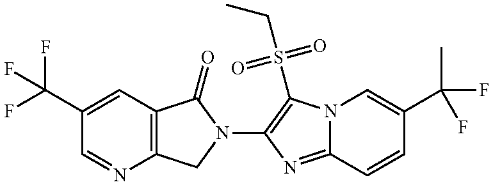 [SMILES: CCS(=O)(=O)c1c(N2Cc3ncc(C(F)(F)F)cc3C2=O)nc2ccc(C(C)(F)F)cn12] | 1.10 | 475 | 1 | 187-190 |
| P19 | 6-[6-(2,2-difluoroethoxy)-3-ethylsulfonyl-imidazo[1,2-a]pyridin-2-yl]-3-(trifluoromethyl)-7H-pyrrolo[3,4-b]pyridin-5-one | 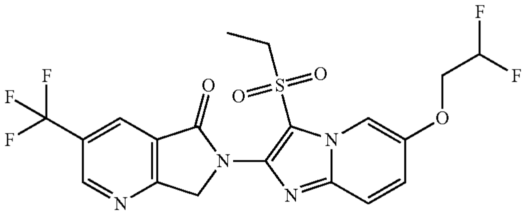 [SMILES: CCS(=O)(=O)c1c(N2Cc3ncc(C(F)(F)F)cc3C2=O)nc2ccc(OCC(F)F)cn12] | 1.09 | 491 | 1 | 188-190 |

TABLE P-continued

Examples of compounds of formula (I)

| No. | IUPAC name | Structures | LCMS $R_t$ (min) | LCMS [M + H]$^+$ (measured) | LCMS Method | Mp (° C.) |
|---|---|---|---|---|---|---|
| P20 | 2-[3-ethylsulfonyl-2-[5-oxo-3-(trifluoromethyl)-7H-pyrrolo[3,4-b]pyridin-6-yl]imidazo[1,2-a]pyridin-6-yl]oxy-2-methyl-propanenitrile | 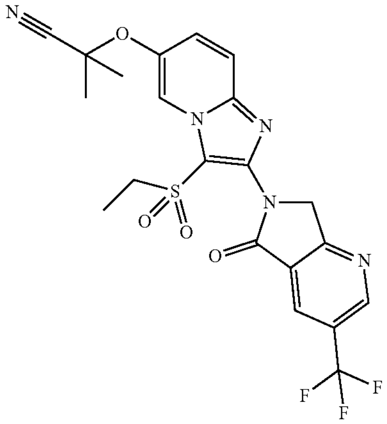 [SMILES: CCS(=O)(=O)c1c(N2Cc3ncc(C(F)(F)F)cc3C2=O)nc2ccc(OC(C)(C)C#N)cn12] | 1.10 | 494 | 1 | 149-151 |
| P21 | 6-(6-bromo-3-ethylsulfonyl-imidazo[1,2-a]pyridin-2-yl)-3-(trifluoromethyl)-7H-pyrrolo[3,4-b]pyridin-5-one | 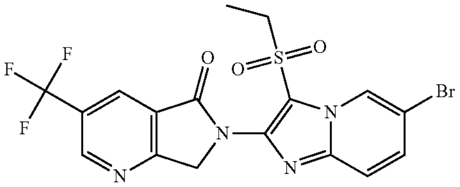 [SMILES: CCS(=O)(=O)c1c(N2Cc3ncc(C(F)(F)F)cc3C2=O)nc2ccc(Br)cn12] | 1.11 | 489/491 | 1 | 218-220 |
| P22 | 6-(7-bromo-3-ethylsulfonyl-imidazo[1,2-a]pyridin-2-yl)-3-(trifluoromethyl)-7H-pyrrolo[3,4-b]pyridin-5-one | 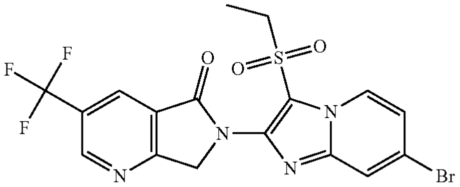 [SMILES: CCS(=O)(=O)c1c(N2Cc3ncc(C(F)(F)F)cc3C2=O)nc2cc(Br)ccn12] | 1.05 | 489/491 | 1 | 225-227 |
| P23 | 6-(3-ethylsulfonyl-7-methyl-imidazo[1,2-a]pyridin-2-yl)-3-(trifluoromethyl)-7H-pyrrolo[3,4-b]pyridin-5-one | 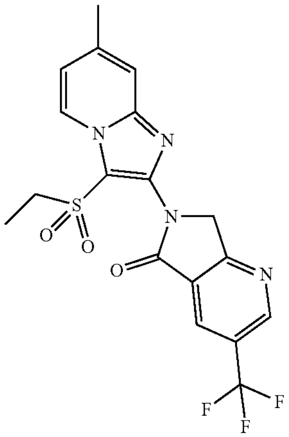 [SMILES: CCS(=O)(=O)c1c(N2Cc3ncc(C(F)(F)F)cc3C2=O)nc2cc(C)ccn12] | 1.43 | 425 | 2 | 166-168 |

TABLE P-continued

Examples of compounds of formula (I)

| No. | IUPAC name | Structures | LCMS $R_t$ (min) | LCMS $[M + H]^+$ (measured) | Method | Mp (° C.) |
|---|---|---|---|---|---|---|
| P24 | 6-(7-cyclopropyl-3-ethylsulfonyl-imidazo[1,2-a]pyridin-2-yl)-3-(trifluoromethyl)-7H-pyrrolo[3,4-b]pyridin-5-one | 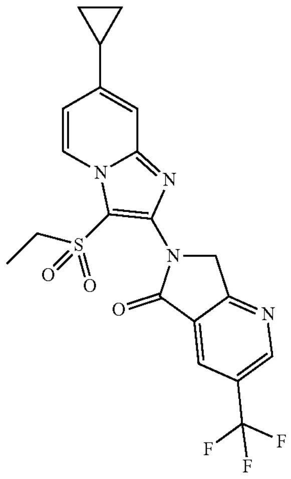 [SMILES: CCS(=O)(=O)c1c(N2Cc3ncc(C(F)(F)F)cc3C2=O)nc2cc(C3CC3)ccn12] | 1.48 | 451 | 2 | 190-192 |
| P25 | 6-[7-(1,1-difluoroethyl)-3-ethylsulfonyl-imidazo[1,2-a]pyridin-2-yl]-3-(trifluoromethyl)-7H-pyrrolo[3,4-b]pyridin-5-one | 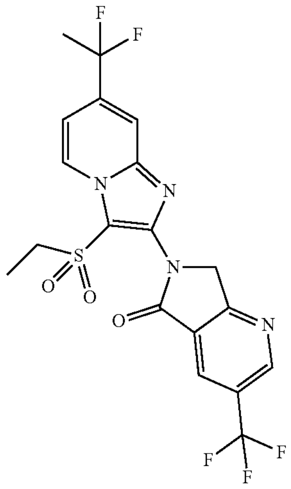 [SMILES: CCS(=O)(=O)c1c(N2Cc3ncc(C(F)(F)F)cc3C2=O)nc2cc(C(C)(F)F)ccn12] | 1.11 | 475 | 1 | 215-217 |
| P26 | 2-[3-ethylsulfonyl-2-[1-oxo-6-(trifluoromethoxy)isoindolin-2-yl]imidazo[1,2-a]pyridin-6-yl]oxy-2-methyl-propanenitrile | 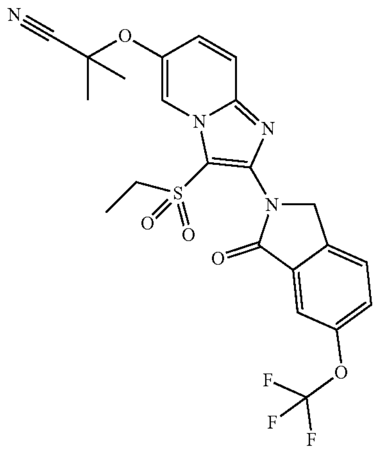 [SMILES: CCS(=O)(=O)c1c(N2Cc3ccc(OC(F)(F)F)cc3C2=O)nc2ccc(OC(C)(C)C#N)cn12] | 1.52 | 509 | 2 | 186-188 |

TABLE P-continued

Examples of compounds of formula (I)

| No. | IUPAC name | Structures | LCMS R$_t$ (min) | LCMS [M + H]$^+$ (measured) | LCMS Method | Mp (° C.) |
|---|---|---|---|---|---|---|
| P27 | 6-(6-cyclopropyl-3-ethylsulfonyl-imidazo[1,2-a]pyridin-2-yl)-3-(trifluoromethyl)-7H-pyrrolo[3,4-b]pyridin-5-one | 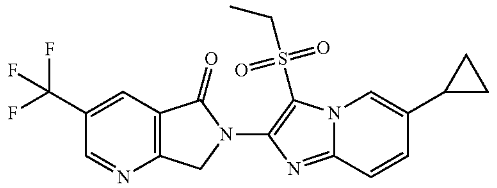 [SMILES: CCS(=O)(=O)c1c(N2Cc3ncc(C(F)(F)F)cc3C2=O)nc2ccc(C3CC3)cn12] | 1.05 | 451 | 1 | 210-212 |
| P28 | 2-[3-ethylsulfonyl-7-(2,2,2-trifluoroethoxy)imidazo[1,2-a]pyridin-2-yl]-6-(trifluoromethoxy)isoindolin-1-one | 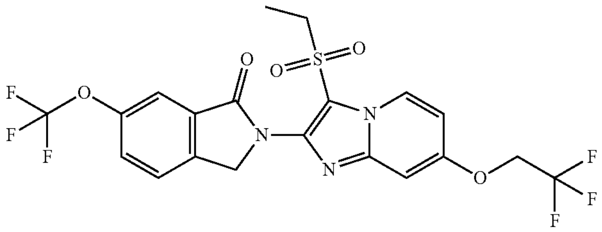 [SMILES: CCS(=O)(=O)c1c(N2Cc3ccc(OC(F)(F)F)cc3C2=O)nc2cc(OCC(F)(F)F)ccn12] | 1.45 | 524 | 2 | 208-210 |
| P29 | 2-(6-bromo-3-ethylsulfonyl-imidazo[1,2-a]pyridin-2-yl)-6-(trifluoromethoxy)isoindolin-1-one | 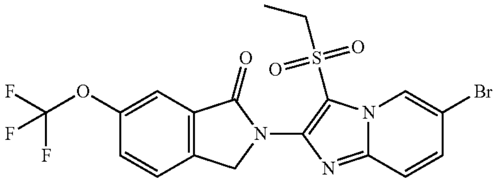 [SMILES: CCS(=O)(=O)c1c(N2Cc3ccc(OC(F)(F)F)cc3C2=O)nc2ccc(Br)cn12] | 1.15 | 504/506 | 1 | 217-219 |
| P30 | 2-(6-bromo-3-ethylsulfonyl-imidazo[1,2-a]pyridin-2-yl)-6-(trifluoromethyl-sulfonyl)isoindolin-1-one | 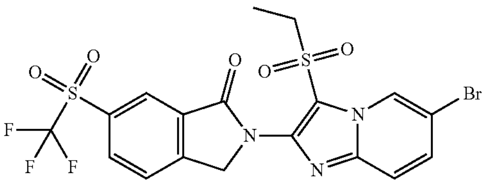 [SMILES: CCS(=O)(=O)c1c(N2Cc3ccc(S(=O)(=O)C(F)(F)F)cc3C2=O)nc2ccc(Br)cn12] | 1.14 | 552/554 | 1 | 251-253 |
| P31 | 1-[[3-ethylsulfonyl-2-[5-oxo-3-(trifluoromethyl)-7H-pyrrolo[3,4-b]pyridin-6-yl]imidazo[1,2-a]pyridin-6-yl]oxymethyl]cyclopropane-carbonitrile | 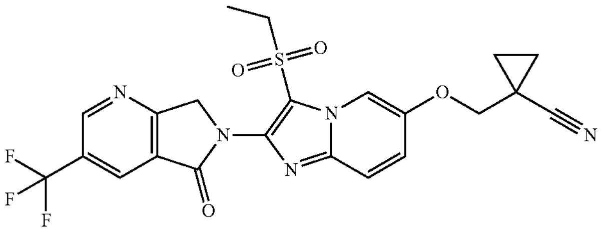 [SMILES: CCS(=O)(=O)c1c(N2Cc3ncc(C(F)(F)F)cc3C2=O)nc2ccc(OCC3(C#N)CC3)cn12] | 1.06 | 506 | 1 | 238-240 |
| P32 | 2-[3-ethylsulfonyl-6-(trifluoromethyl)imidazo[1,2-a]pyridin-2-yl]-6-(trifluoromethyl-sulfonyl)isoindolin-1-one | 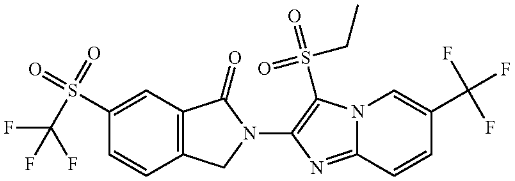 [SMILES: CCS(=O)(=O)c1c(N2Cc3ccc(S(=O)(=O)C(F)(F)F)cc3C2=O)nc2ccc(C(F)(F)F)cn12] | 1.13 | 542 | 1 | 264-266 |
| P33 | 2-[3-ethylsulfonyl-7-(2,2,2-trifluoroethoxy)imidazo[1,2-a]pyridin-2-yl]-6-(trifluoromethyl-sulfonyl)isoindolin-1-one | 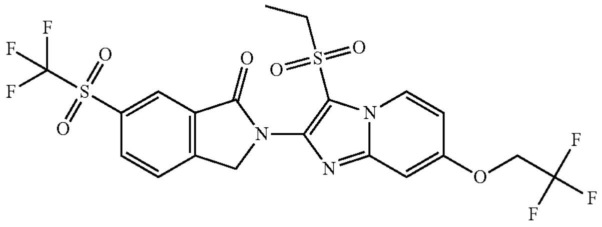 [SMILES: CCS(=O)(=O)c1c(N2Cc3ccc(S(=O)(=O)C(F)(F)F)cc3C2=O)nc2cc(OCC(F)(F)F)ccn12] | 1.53 | 572 | 2 | 215-217 |

TABLE P-continued

| Examples of compounds of formula (I) | | | | | | |
|---|---|---|---|---|---|---|
| | | | LCMS | | | |
| No. | IUPAC name | Structures | $R_t$ (min) | [M + H]+ (measured) | Method | Mp (° C.) |
| P34 | 6-(difluoromethoxy)-2-[3-ethylsulfonyl-6-(trifluoromethyl) imidazo[1,2-a]pyridin-2-yl]isoindolin-1-one | 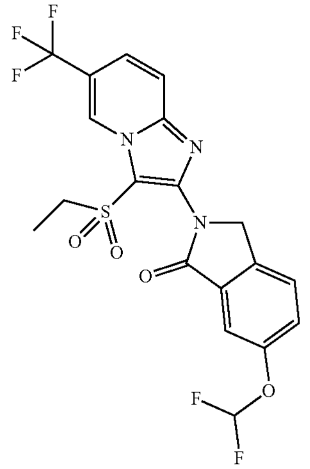 [SMILES: CCS(=O)(=O)c1c(N2Cc3ccc(OC(F)F)cc3C2=O)nc2ccc(C(F)(F)F)cn12] | 1.09 | 476 | 1 | 169-171 |
| P35 | 2-[3-ethylsulfonyl-2-[5-oxo-3-(trifluoromethyl)-7H-pyrrolo[3,4-b]pyridin-6-yl]imidazo[1,2-a] pyridin-6-yl]-2-methyl-propanenitrile | 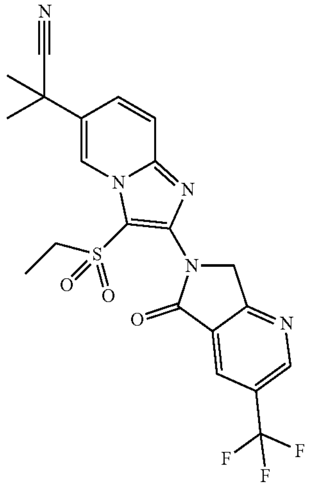 [SMILES: CCS(=O)(=O)c1c(N2Cc3ncc(C(F)(F)F)cc3C2=O)nc2ccc(C(C)(C)C#N)cn12] | 1.04 | 478 | 1 | 209-211 |
| P36 | N-[3-ethylsulfonyl-2-[5-oxo-3-(trifluoromethyl)-7H-pyrrolo[3,4-b]pyridin-6-yl]imidazo[1,2-a] pyridin-6-yl]acetamide | 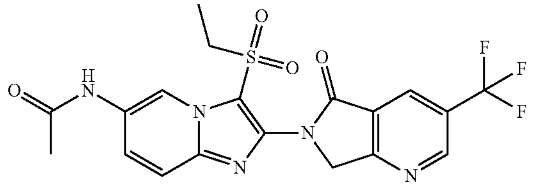 [SMILES: CCS(=O)(=O)c1c(N2Cc3ncc(C(F)(F)F)cc3C2=O)nc2ccc(NC(C)=O)cn12] | 1.25 | 468 | 2 | 248-250 |
| P37 | 2-[3-ethylsulfonyl-7-(trifluoromethyl) imidazo[1,2-a] pyridin-2-yl]-6-(trifluoromethyl-sulfonyl) isoindolin-1-one | 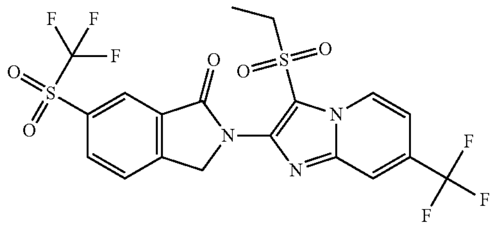 [SMILES: CCS(=O)(=O)c1c(N2Cc3ccc(S(=O)(=O)C(F)(F)F)cc3C2=O)nc2cc(C(F)(F)F)ccn12] | 1.15 | 542 | 1 | 114-116 |

TABLE P-continued

Examples of compounds of formula (I)

| No. | IUPAC name | Structures | LCMS $R_t$ (min) | LCMS $[M + H]^+$ (measured) | LCMS Method | Mp (° C.) |
|---|---|---|---|---|---|---|
| P38 | 6-[7-(2,2-difluoroethoxy)-3-ethylsulfonyl-imidazo[1,2-a]pyridin-2-yl]-3-(trifluoromethyl)-7H-pyrrolo[3,4-b]pyridin-5-one | 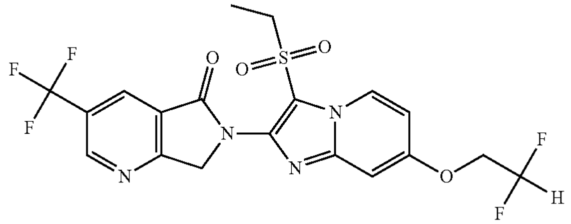 [SMILES: CCS(=O)(=O)c1c(N2Cc3ncc(C(F)(F)F)cc3C2=O)nc2cc(OCC(F)F)ccn12] | 1.06 | 491 | 1 | 188-190 |

Intermediate Preparation

Example I1: Preparation of ethyl 5-(bromomethyl)-2-(trifluoromethyl)pyridine-4-carboxylate (Intermediate IP-5)

(IP-5)

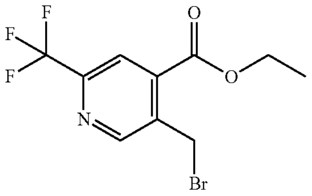

Step A1: Preparation of 5-chloro-2-(trifluoromethyl) pyridine-4-carboxylic acid (Intermediate IP-1) and 2,2,6,6-tetramethylpiperidin-1-ium 5-chloro-2-(trifluormethyl)pyridine-4-carboxylate (Intermediate IP-2)

(IP-1)

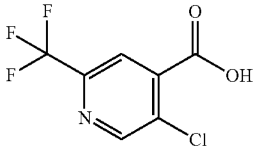

(IP-2)

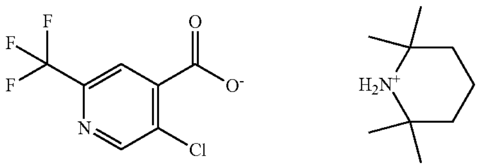

A 2.0 M butyllithium solution in tetrahydrofuran (165 mL, 330 mmol, 4.00 equiv.) was added dropwise to a −78° C. cooled solution of 2,2,6,6-tetramethylpiperidine (35.0 g, 248 mmol, 3.00 equiv.) in tetrahydrofuran (500 mL). After complete addition, the reaction mixture was stirred for 30 min at −50° C. and cooled again to −78° C. before adding a solution of 5-chloro-2-(trifluoromethyl)pyridine (15.0 g, 82.6 mmol) in tetrahydrofuran (100 mL). The reaction mixture was stirred for 30 min at −78° C. before being added via cannula to a $CO_2$ saturated solution of tetrahydrofuran cooled at −78° C. Once the addition was complete, the reaction mixture was warmed up to room temperature, and quenched by addition of a saturated ammonium chloride aqueous solution (200 mL). The aqueous phase was extracted twice with ethyl acetate (200 mL), the combined organic phases were dried over sodium sulfate, filtered and concentrated under reduced pressure to give 2,2,6,6-tetramethylpiperidin-1-ium 5-chloro-2-(trifluoromethyl)pyridine-4-carboxylate (intermediate IP-2). The aqueous phase was acidified to pH 3 by addition of a 2 M hydrochloric acid aqueous solution and extracted twice with a 90/10 mixture of dichloromethane/methanol (200 mL). The combined organic phases were dried over sodium sulfate, filtered and concentrated under reduced pressure to give 5-chloro-2-(trifluoromethyl)pyridine-4-carboxylic acid (intermediate IP-1). Both crude materials were used in the next step without further purification. LCMS (method 1): m/z 226 $[M+H]^+$, retention time 0.67 min. $^1H$ NMR (400 MHz, DMSO-d6) δ/ppm: 8.18 (s, 1H), 8.98 (s, 1H) for 5-chloro-2-(trifluoromethyl)pyridine-4-carboxylic acid (IP-1).

Step A2: Preparation of ethyl 5-chloro-2-(trifluoromethyl)pyridine-4-carboxylate (Intermediate IP-3)

(IP-3)

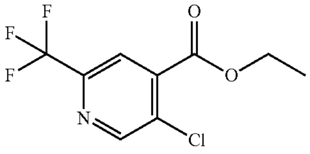

A mixture of 5-chloro-2-(trifluoromethyl)pyridine-4-carboxylic acid (intermediate IP-1) prepared as described above) (1.00 g, 4.43 mmol) and concentrated sulfuric acid (1.00 mL) in ethanol (30 mL) was heated at reflux overnight. After cooling to room temperature, the reaction mixture was concentrated and the residue was diluted with iced water (50 mL). The aqueous phase was extracted twice with ethyl acetate (2×30 mL), the combined organic phases were washed with brine (30 mL), dried over sodium sulfate, filtered and concentrated. The crude material was purified by flash chromatography over silica gel (ethyl acetate in cyclohexane) to give the desired compound as a yellow liquid. LCMS (method 1): m/z 254 $[M+H]^+$, retention time 1.10 min. $^1H$ NMR (400 MHz, $CDCl_3$) δ/ppm: 1.45 (t, J=7.12 Hz, 3H), 4.49 (q, J=7.12 Hz, 2H), 8.04 (s, 1H), 8.82 (s, 1H).

Step A3: Preparation of ethyl 5-methyl-2-(trifluoromethyl)pyridine-4-carboxylate (Intermediate IP-4)

(IP-4)

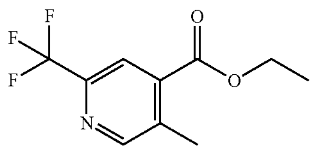

Tripotassium phosphate (4.5 g, 21.3 mmol, 3.0 equiv.) and tricyclohexylphosphine (0.2 g, 0.71 mmol, 0.10 equiv.) were added to a mixture of ethyl 5-chloro-2-(trifluoromethyl) pyridine-4-carboxylate (intermediate IP-3 prepared as described above) (1.8 g, 7.1 mmol) and methyl-boronic acid (1.3 g, 21.3 mmol, 3.0 equiv.) in toluene (50 mL) and water (5.0 mL). The mixture was purged with nitrogen for 10 min before adding palladium acetate (0.08 g, 0.035 mmol, 0.05 equiv.). Purging was continued for 10 min and the reaction mixture was heated at 100° C. for 2 hours. After cooling down to room temperature, the mixture was diluted with water (50 mL) and ethyl acetate (50 mL), and filtered over Celite (washed with ethyl acetate). The phases were separated, the aqueous phase was extracted with ethyl acetate, the combined organic phases were dried over sodium sulfate, filtered and concentrated. Purification of the crude material by flash chromatography over silica gel (ethyl acetate in cyclohexane) afforded the desired compound as a pale yellow liquid. LCMS (method 1): m/z 234 $[M+H]^+$, retention time 1.08 min. $^1H$ NMR (400 MHz, $CDCl_3$) δ/ppm: 1.44 (t, J=7.16 Hz, 3H), 2.66 (s, 3H), 4.44 (q, J=7.16 Hz, 2H), 8.08 (s, 1H), 8.68 (s, 1H).

Step A4: Preparation of ethyl 5-(bromomethyl)-2-(trifluoromethyl)pyridine-4-carboxylate (Intermediate IP-5)

(IP-5)

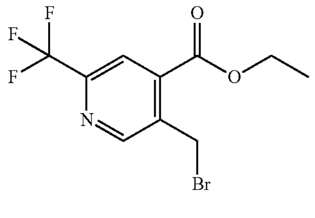

N-bromosuccinimide (1.40 g, 7.80 mmol, 1.40 equiv.) and benzoyl peroxide (0.42 g, 1.70 mmol, 0.30 equiv.) were added to a solution of ethyl 5-methyl-2-(trifluoromethyl) pyridine-4-carboxylate (intermediate IP-4 prepared as described above) (1.30 g, 5.60 mmol) in tetrachloromethane (45 mL). The reaction mixture was heated at 70° C. overnight. After cooling down to room temperature, the reaction mixture was diluted with iced water (20 mL), and the aqueous phase was extracted twice with ethyl acetate (10 mL). The combined organic phases were dried over sodium sulfate, filtered and concentrated. The crude material was purified by flash chromatography over silica gel (ethyl acetate in cyclohexane) to give the desired product. LCMS (method 1): m/z 312/314 $[M+H]^+$, retention time 1.12 min. $^1H$ NMR (400 MHz, $CDCl_3$) δ/ppm: 1.44 (t, J=7.15 Hz, 3H), 4.50 (q, J=7.15 Hz, 2H), 4.94 (s, 2H), 7.27 (s, 1H), 8.14 (s, 1H), 8.85 (s, 1H).

Similarly, methyl 5-(bromomethyl)-2-(trifluoromethyl) pyridine-4-carboxylate (IP-6) can be prepared:

(IP-6)

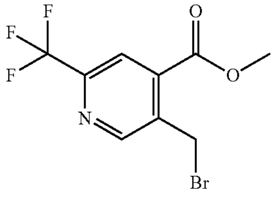

LCMS (method 1): m/z 298/300 $[M+H]^+$, retention time 1.06 min. $^1H$ NMR (400 MHz, $CDCl_3$) δ/ppm: 4.04 (s, 3H), 4.95 (s, 2H), 8.15 (s, 1H), 8.87 (s, 1H).

Example 12: Preparation of tert-butyl N-[6-(1,1-difluoroethyl)-3-ethylsulfonyl-imidazo[1,2-a]pyridin-2-yl]carbamate (Intermediate IQ-7)

(IQ-7)

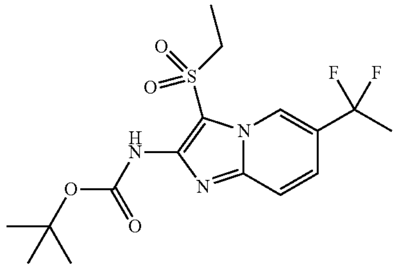

Step 1: Preparation of ethyl 6-bromo-3-ethylsulfonyl-imidazo[1,2-a]pyridine-2-carboxylate (Intermediate IP-7)

(IP-7)

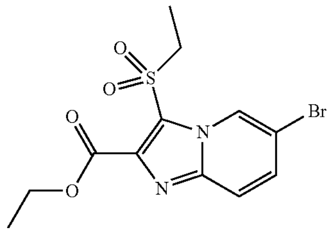

Obtained from ethyl 6-bromo-3-ethylsulfanyl-imidazo[1,2-a]pyridine-2-carboxylate (CAS 2093460-48-9) by following procedure Example H3/step 5. LCMS (method 1): m/z 361/363 $[M+H]^+$, retention time Rt=0.93 min.

Step 2: Preparation of ethyl 6-(1-ethoxyvinyl)-3-ethylsulfonyl-imidazo[1,2-a]pyridine-2-carboxylate (Intermediate IP-8)

(IP-8)

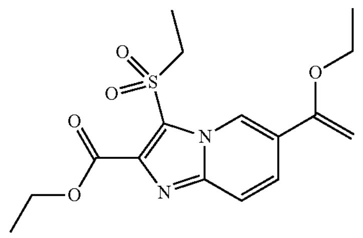

To a solution of ethyl 6-bromo-3-ethylsulfonyl-imidazo[1,2-a]pyridine-2-carboxylate (intermediate IP-7 prepared as described above) (5 g, 13.15 mmol) in N,N-dimethylformamide (52.6 mL) was added tributyl(1-ethoxyvinyl)tin (6.0 g, 15.78 mmol, 5.61 mL). The reaction mixture was flushed with nitrogen for 15 minutes, then bis(triphenylphosphine)palladium(II) dichloride (0.466 g, 0.657 mmol) was added. The resulting mixture was heated at 80° C. for 3 hours, then cooled to room temperature and used directly in the next step.

Step 3: Preparation of ethyl 6-acetyl-3-ethylsulfonyl-imidazo[1,2-a]pyridine-2-carboxylate (Intermediate IP-9)

(IP-9)

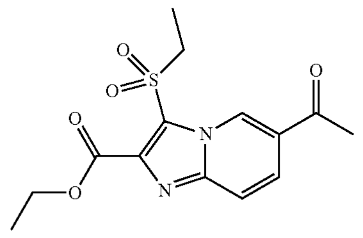

To the crude solution of ethyl 6-(1-ethoxyvinyl)-3-ethylsulfonyl-imidazo[1,2-a]pyridine-2-carboxylate (intermediate IP-8) obtained above was added an aqueous 2N hydrochloric acid solution (20 mL) and stirring continued at room temperature for 60 minutes. The mixture was diluted with water (100 mL) and the product extracted with ethyl acetate (100 mL). The organic layer was filtered through Celite, the Celite bed washed using ethyl acetate (20 mL), the combined organic layers washed with brine (10 mL), dried over sodium sulfate, filtered and concentrated under vacuum. The crude material was purified by combiflash (silicagel, 30-60% ethyl acetate in cyclohexane) to afford the desired product. LCMS (method 1): m/z 325 $[M+H]^+$, retention time Rt=0.96 min.

Step 4: Preparation of ethyl 6-(1,1-difluoroethyl)-3-ethylsulfonyl-imidazo[1,2-a]pyridine-2-carboxylate (Intermediate IP-10)

(IP-10)

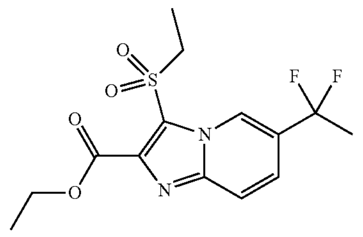

To a solution of ethyl 6-acetyl-3-ethylsulfonyl-imidazo[1,2-a]pyridine-2-carboxylate (intermediate IP-9 prepared as described above) (2.6 g, 7.6 mmol) in toluene (26 mL) under nitrogen was added bis(2-methoxyethyl)aminosulfur trifluoride (13 g, 30 mmol, 11 mL) dropwise. The reaction mixture was stirred at 80° C. for 12 hours, cooled and quenched carefully by adding an aqueous saturated sodium carbonate solution. After further dilution with ice-cold water (100 mL), the product was extracted with ethyl acetate (3×75 mL), the combined organic phases dried over sodium sulfate, filtered and concentrated under reduced pressure. The residue was purified by combiflash (20-50% ethyl acetate in cyclohexane) to afford the desired product. LCMS (method 1): m/z 347 $[M+H]^+$, retention time Rt=1.04 min.

Step 5: Preparation of 6-(1,1-difluoroethyl)-3-ethylsulfonyl-imidazo[1,2-a]pyridine-2-carboxylic Acid (Intermediate IP-11)

(IP-11)

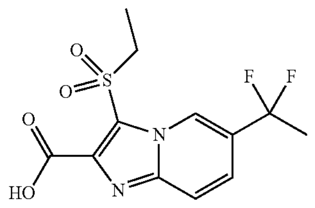

Obtained from ethyl 6-(1,1-difluoroethyl)-3-ethylsulfonyl-imidazo[1,2-a]pyridine-2-carboxylate (intermediate IP-10) by following procedure Example H3/step 6. LCMS (method 1): m/z 319 $[M+H]^+$, retention time Rt=0.92 min.

Step 6: Preparation of tert-butyl N-[6-(1,1-difluoroethyl)-3-ethylsulfonyl-imidazo[1,2-a]pyridin-2-yl]carbamate (Intermediate IQ-7)

(IQ-7)

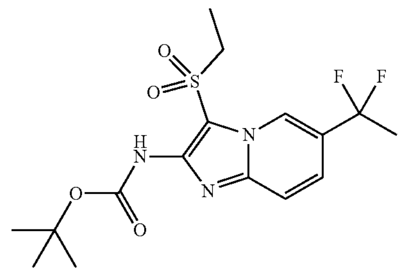

Obtained from 6-(1,1-difluoroethyl)-3-ethylsulfonyl-imidazo[1,2-a]pyridine-2-carboxylic acid (intermediate IP-11) by following procedure Example H3/step 7. $^1$H NMR (400 MHz, DMSO-$d_6$) δ ppm 9.47 (s, 1H), 8.85 (d, 1H), 7.84 (d, 1H), 7.77 (dd, 1H), 3.68 (q, 2H), 2.08 (t, J=19.07 Hz, 3H), 1.48 (s, 9H), 1.26 (t, 3H).

TABLE Q

Examples of intermediate compounds of formula (XIX-Qa-1)

(XIX-Qa-1)

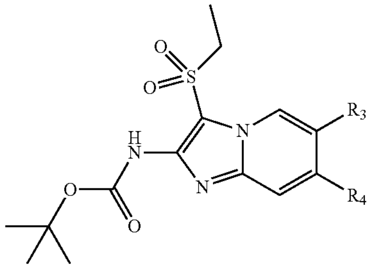

| No. | $R_3$ | $R_4$ | $^1$H NMR |
|---|---|---|---|
| IQ-1 | $CF_3$ | H | $^1$H NMR (400 MHz, $CDCl_3$) δ ppm 1.36 (t, 3 H) 1.56 (s, 9 H) 3.28 (q, 2 H) 7.59-7.64 (m, 1 H) 7.85 (d, 1 H) 8.24 (s, 1 H) 8.97 (s, 1 H). |
| II-1 | H | $CF_3$ | $^1$H NMR (400 MHz, DMSO-d6) δ ppm 1.27 (t, 3 H) 1.48 (s, 9 H) 3.66 (q, 2 H) 7.47 (dd, 1 H) 8.24 (s, 1 H) 8.94 (d, 1 H) 9.57 (s, 1 H). |
| IQ-2 | H | 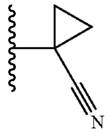 | $^1$H NMR (400 MHz, $CDCl_3$) δ ppm 1.33 (t, 3 H) 1.50-1.55 (m, 2 H) 1.56 (s, 9 H) 1.87-1.96 (m, 2 H) 3.24 (q, 2 H) 7.05 (dd, 1 H) 7.55 (s, 1 H) 8.19 (s, 1 H) 8.61 (dd, 1 H). |
| IQ-3 | 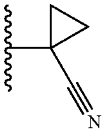 | H | $^1$H NMR (400 MHz, $CDCl_3$) δ ppm 1.36 (t, 3 H) 1.44-1.50 (m, 2 H) 1.57 (s, 9 H) 1.80-1.85 (m, 2 H) 3.24-3.31 (m, 2 H) 7.42 (dd, 1 H) 7.75 (d, 1 H) 8.23 (s, 1 H) 8.65 (s, 1 H). |
| IQ-4 | H | $OCH_3$ | $^1$H NMR (400 MHz, DMSO-d6) δ ppm 1.21 (t, 3 H) 1.47 (s, 9 H) 3.54 (q, 2 H) 3.89 (s, 3 H) 6.89 (dd, 1 H) 7.12 (d, 1 H) 8.55 (d, 1 H) 9.24 (s, 1 H). |
| IQ-5 | $OCH_3$ | H | $^1$H NMR (400 MHz, $CDCl_3$) δ ppm 1.34 (t, 3 H) 1.56 (s, 9 H) 3.24 (q, 2 H) 3.88 (s, 3 H) 7.23 (dd, 1 H) 7.64 (d, 1 H) 8.16 (s, 1 H) 8.20 (d, 1 H). |
| IQ-6 | H | Br | $^1$H NMR (400 MHz, $CDCl_3$) δ ppm 1.32 (t, 3 H) 1.55 (s, 9 H) 3.23 (q, 2 H) 7.13 (dd, 1 H) 7.91 (dd, 1 H) 8.19 (s, 1 H) 8.48 (dd, 1 H). |
| IQ-7 | $CF_2CH_3$ | H | $^1$H NMR (400 MHz, DMSO-$d_6$) δ ppm 9.47 (s, 1H), 8.85 (d, 1H), 7.84 (d, 1H), 7.77 (dd, 1H), 3.68 (q, 2H), 2.08 (t, J = 19.07 Hz, 3H), 1.48 (s, 9H), 1.26 (t, 3H). |
| III-7 | H | $OCH_2CF_3$ | $^1$H NMR (400 MHz, $CDCl_3$) δ ppm 1.32 (t, 3 H) 1.56 (s, 9 H) 3.22 (q, 2 H) 4.41 (q, 2 H) 6.79 (dd, 1 H) 7.05 (d, 1 H) 8.16 (s, 1 H) 8.51 (d, 1 H). |
| IQ-8 | Br | H | $^1$H NMR (400 MHz, $CDCl_3$) δ ppm 1.25 (t, 3 H) 1.46 (s, 9 H) 3.66 (q, 2 H) 7.70 (d, 1 H) 7.74 (d, 1 H) 8.83 (s, 1 H) 9.43 (s, 1 H). |
| VI-9 | 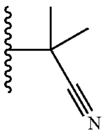 | H | $^1$H NMR (400 MHz, DMSO-d6) δ ppm 1.26 (t, 3 H) 1.47 (s, 9 H) 1.77 (s, 6 H) 3.65 (q, 2 H) 7.77-7.84 (m, 2H) 8.79 (s, 1 H) 9.40 (s, 1 H). |
| IQ-9 | H | $CF_2CH_3$ | $^1$H NMR (400 MHz, DMSO-d6) δ ppm 1.25 (t, 3 H) 1.48 (s, 9 H) 1.98-2.12 (m, 3 H) 3.63 (q, 2 H) 7.36 (dd, 1 H) 7.92 (s, 1 H) 8.85 (d, 1 H) 9.48 (s, 1 H). |
| IQ-10 | 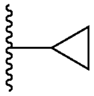 [SMILES: *C1CC1] | H | $^1$H NMR (400 MHz, $CDCl_3$) δ ppm 0.69-0.80 (m, 2 H) 1.01-1.10 (m, 2 H) 1.33 (t, 3 H) 1.56 (s, 9 H) 1.92-2.00 (m, 1 H) 3.24 (q, 2 H) 7.15 (dd, 1 H) 7.64 (d, 1 H) 8.23 (s, 1 H) 8.42 (s, 1 H). |

TABLE R

Examples of intermediate compounds of formula (X-Qa-1)

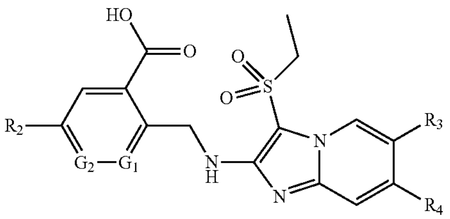

(X-Qa-1)

| No. | $R_3$ | $R_4$ | $G_1$ | $G_2$ | $R_2$ | LCMS $R_t$ (min) | LCMS $[M-H]^-$ (measured) | LCMS Method |
|---|---|---|---|---|---|---|---|---|
| IR-1 (II-7) | H | $CF_3$ | N | CH | $CF_3$ | 1.04 | 495 | 1 |
| IR-2 | H | 1-CNCyPr | N | CH | $CF_3$ | 0.96 | 492 | 1 |
| IR-3 | $CF_3$ | H | N | CH | $CF_3$ | 1.51 | 495 | 2 |
| IR-4 | H | 1-CNCyPr | CH | CH | $OCF_3$ | 1.04 | 507 | 1 |
| IR-5 | $CF_3$ | H | CH | CH | $OCF_3$ | 1.10 | 510 | 1 |
| IR-6 | H | $CF_3$ | CH | CH | $OCF_3$ | 1.11 | 510 | 1 |
| IR-7 | $OCH_3$ | H | N | CH | $CF_3$ | 0.94 | 457 | 1 |
| IR-8 | $OCH(CH_3)_2$ | H | N | CH | $CF_3$ | — | — | — |
| IR-9 | $OCHF_2$ | H | N | CH | $CF_3$ | — | — | — |
| IR-10 | $OCH_2CF_3$ | H | N | CH | $CF_3$ | — | — | |
| IR-11 | H | $OCH_2CF_3$ | N | CH | $CF_3$ | 1.02 | 525 | 1 |
| IR-12 | H | $OCH_3$ | N | CH | $CF_3$ | 0.93 | 457 | 1 |
| IR-13 | 1-CNCyPr | H | CH | CH | $OCF_3$ | 1.01 | 507 | 1 |
| IR-14 | 1-CNCyPr | H | N | CH | $CF_3$ | 0.95 | 492 | 1 |
| IR-15 | 1-CNCyPr | H | CH | CH | $CF_3$ | 1.00 | 491 | 1 |
| IR-16 | $CF_2CH_3$ | H | CH | CH | $OCF_3$ | 1.06 | 506 | 1 |
| IR-17 | $CF_2CH_3$ | H | N | CH | $CF_3$ | 1.09 | 491 | 1 |
| IR-18 | $OCH_2CHF_2$ | H | N | CH | $CF_3$ | — | — | — |
| IR-19 | $OC(CH_3)_2(CN)$ | H | N | CH | $CF_3$ | — | — | — |
| IR-20 (IV-3) | Br | H | N | CH | $CF_3$ | 1.01 | 505/507 | 1 |
| IR-21 | H | Br | N | CH | $CF_3$ | 1.48 | 505/507 | 2 |
| IR-22 | H | $CH_3$ | N | CH | $CF_3$ | — | — | — |
| IR-23 | H | CyPr | N | CH | $CF_3$ | — | — | — |
| IR-24 | H | $CF_2CH_3$ | N | CH | $CF_3$ | 1.09 | 491 | 1 |
| IR-25 | $OC(CH_3)_2(CN)$ | H | CH | CH | $OCF_3$ | — | — | — |
| IR-26 | CyPr | H | N | CH | $CF_3$ | — | — | — |
| IR-27 | H | $OCH_2CF_3$ | CH | CH | $OCF_3$ | 1.09 | 540 | 1 |
| IR-28 | Br | H | CH | CH | $OCF_3$ | 1.14 | 520/522 | 1 |
| IR-29 | Br | H | CH | CH | $S(O_2)CF_3$ | 1.10 | 568/570 | 1 |
| IR-30 | $OCH_2$(1-CNCyPr) | H | N | CH | $CF_3$ | — | — | — |
| IR-31 | $CF_3$ | H | CH | CH | $S(O_2)CF_3$ | 1.10 | 558 | 1 |
| IR-32 (III-10) | H | $OCH_2CF_3$ | CH | CH | $S(O_2)CF_3$ | 1.51 | 588 | 2 |
| IR-33 | $CF_3$ | H | CH | CH | $OCHF_2$ | 1.09 | 492 | 1 |
| IR-34 (VI-12) | $C(CH_3)_2CN$ | H | N | CH | $CF_3$ | 1.02 | 494 | 1 |
| IR-35 | $NH(CO)CH_3$ | H | N | CH | $CF_3$ | — | — | — |
| IR-36 | H | $CF_3$ | CH | CH | $S(O_2)CF_3$ | 1.13 | 558 | 1 |
| IR-37 (V-3) | $OCH_3$ | H | CH | CH | $OCF_3$ | 1.09 | 472 | 1 |

wherein CyPr = cyclopropyl and 1-CNCyPr = 1-cyanocyclopropyl

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables A-1 to A-12, B-1 to B-12, C-1 to C-18, D-1 to D-18, E-1 to E-12, F-1 to F-12, G-1 to G-18, and H-1 to H-18, and Table P of the present invention"):

an adjuvant selected from the group of substances consisting of petroleum oils (alternative name) (628)+TX; an insect control active substance selected from Abamectin+TX, Acequinocyl+TX, Acetamiprid+TX, Acetoprole+TX, Acrinathrin+TX, Acynonapyr+TX, Afidopyropen+TX, Afoxolaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Beta-cypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2246757-58-2 (or 2249718-27-0)+TX, CAS number: 907187-07-9+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cyclobutrifluram+TX, Cycloprothrin+TX, Cycloxaprid+TX, Cycloxaprid+TX, Cyenopyrafen+TX, Cyetpyrafen+TX, Cyflumetofen+TX, Cyfluthrin+TX, Cyhalodiamide+TX, Cyhalothrin+TX, Cypermethrin+TX, Cyphenothrin+TX, Cyproflanilide+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin (or Emamectin Benzoate)+TX, Empenthrin+TX, Epsilon-momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupentiofenox+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halfenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nicofluprole+TX; Nitenpyram+TX, Nithiazine+TX, Omethoate+TX, Oxamyl+TX, Oxazosulfyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Pirimiphos-methyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyriminostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachlorantraniliprole+TX, Tetradiphon+TX, Tetramethrin+TX, Tetramethylfluthrin+TX, Tetranactin+TX, Tetraniliprole+TX, Theta-cypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, Azadirachtin+TX, *Bacillus aizawai*+TX, *Bacillus* chitinosporus AQ746 (NRRL Accession No B-21 618)+TX, *Bacillus firmus*+TX, *Bacillus* kurstaki+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. kurstaki BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paeci-*

*lomyces lilacinus*+TX, *Pasteuria nishizawae*+TX, *Pasteuria penetrans*+TX, *Pasteuria ramosa*+TX, *Pasteuria thornei*+TX, *Pasteuria* usgae+TX, P-cymene+TX, *Plutella xylostella* Granulosis virus+TX, *Plutella xylostella* Nucleopolyhedrovirus+TX, Polyhedrosis virus+TX, pyrethrum+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp.;

an algaecide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, Cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX; a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. japonensis (scientific name) (51)+TX, *Bacillus thuringiensis* subsp. kurstaki (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, Neodiprion sertifer NPV and *N. lecontei* NPV (alternative name) (575)+TX, Orius spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, Steinernema bibionis (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+

TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX;

an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX;

a molluscicide selected from the group of substances consisting of bis(tributyltin) oxide (IUPAC name) (913)+TX, bromoacetamide [CCN]+TX, calcium arsenate [CCN]+TX, chloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX;

a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, Cyclobutrifluram+TX, cytokinins (alternative name) (210)+TX, dazomet (216)+TX, DBCP (1045)+TX, DClP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S- methyl (6)+TX, probenazole (658) and *Reynoutria sachalinensis* extract (alternative name) (720)+TX;

a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX;

a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX;

a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, Neodiprion sertifer NPV and *N. lecontei* NPV+TX, Orius spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquinbutyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl) aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, 2-fluoro-N-(3-methoxyphenyl)-9H-purin-6-amine+TX, benclothiaz+TX, cytokinins+TX, DClP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, –sodium fluoroacetate+TX, thallium sulfate+TX, warfarin+TX, –2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, chloroinconazide+TX, mercuric oxide+TX, thiophanate-methyl+TX, azaconazole+TX, bitertanol+TX, bromuconazole+TX, cyproconazole+TX, difenoconazole+TX, diniconazole –+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, –simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, –metalaxyl –+TX, Rmetalaxyl+TX, ofurace+TX, oxadixyl+TX, carbendazim+TX, debacarb+TX, fuberidazole –+TX, thiabendazole+TX, chlozolinate+TX, dichlozoline+TX, myclozoline-+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb –+TX, chloro-thalonil+TX, cyflufenamid+TX, cymoxanil+TX, cyclobutrifluram+TX, diclocymet+TX, diclomezine –+TX, dicloran+TX, diethofencarb+TX, dimethomorph –+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, –fenhexamid+TX, fosetyl-aluminium –+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl]methanesulfonate+TX, but-3-ynyl N-[6-[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl)pyridine-3-carboxamide+TX, 4-[[6-[2-(2,4-difluoro-phenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1,1,3-trimethylindan-4-yl)pyridine-3-carboxamide+TX, α-(1,1-dimethylethyl)-α-[4'-(trifluoromethoxy)[1,1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, N-octyl-N'-[2-(octylamino)ethyl]ethane-1,2-diamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifuoromethyl)tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl)methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3- dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7 (2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N-[(Z)-methoxyiminomethyl]-4-[5-(trifluoromethyl)-1,2,4-oxadiazol-3-yl]benzamide+TX, N-[N-methoxy-C-methyl-carbonimidoyl]-4-[5-(trifluoromethyl)-1,2,4-oxadiazol-3-yl]benzamide+TX (these compounds may be prepared from the methods described in WO 2018/202428); microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus sphaericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1 Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea* dravisae+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces lilacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aerofaciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomonas fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rahnella aquatilis*+TX, *Rahnella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis nucleopolyhedrovirus* (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); pheromones including: blackheaded fireworm pheromone (3 M Sprayable Blackheaded Fireworm Pheromone®)+TX, Codling Moth Pheromone (Paramount dispenser-(CM)/Isomate C-Plus®)+TX, Grape Berry Moth Pheromone (3 M MEC-GBM Sprayable Pheromone®)+TX, Leafroller pheromone (3 M MEC-LR Sprayable Pheromone®)+TX, Muscamone (Snip7 Fly Bait®+TX, Starbar Premium Fly Bait®)+TX, Oriental Fruit Moth Pheromone (3 M oriental fruit moth sprayable Pheromone®)+TX, Peachtree Borer Pheromone (Isomate-P®)+TX, Tomato Pinworm Pheromone (3 M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cynocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus bal-*

*teatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesidiocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rhodiola cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline SF®+TX, Scia-Rid®+TX, Entonem®)+TX, *Steinernema kraussei* (Nemasys L®+TX, BioNem L®+TX, Exhibitline SRB®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, Microctonus hyperodae+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables A-1 to A-12, B-1 to B-12, C-1 to C-18, D-1 to D-18, E-1 to E-12, F-1 to F-12, G-1 to G-18, and H-1 to H-18, and Table P with active ingredients described above comprises a compound selected from Tables A-1 to A-12, B-1 to B-12, C-1 to C-18, D-1 to D-18, E-1 to E-12, F-1 to F-12, G-1 to G-18, and H-1 to H-18, and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables A-1 to A-12, B-1 to B-12, C-1 to C-18, D-1 to D-18, E-1 to E-12, F-1 to F-12, G-1 to G-18, and H-1 to H-18, and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables A-1 to A-12, B-1 to B-12, C-1 to C-18, D-1 to D-18, E-1 to E-12, F-1 to F-12, G-1 to G-18, and H-1 to H-18, and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematicides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Example B1: Activity Against *Bemisia tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm: P1, P3, P4, P5, P6, P7, P10, P14, P15, P16, P17, P20, P26, P33, P35, P37.

Example B2: Activity Against *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P3, P4, P5, P6, P7, P8, P10, P11, P12, P13, P14, P15, P16, P17, P19, P20, P21, P22, P23, P24, P26, P27, P29, P30, P31, P32, P33, P34, P35, P36, P37.

Example B3: Activity Against *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P3, P4, P5, P6, P8, P10, P12, P14, P15, P16, P17, P19, P21, P24, P27, P33, P35, P37.

Example B4: Activity Against *Frankliniella occidentalis* (Western Flower *Thrips*)

Sunflower leaf discs were placed on agar in 24-well microtiter plates and sprayed with aqueous test solutions prepared from 10,000 ppm DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P3, P5, P10, P14, P15, P17, P27, P33, P35, P37.

Example B5: Activity Against *Plutella xylostella* (Diamond Back Moth)

24-well microtiter plates with artificial diet were treated with aqueous test solutions prepared from 10,000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm: P1, P2, P3, P4, P5, P6, P7, P8, P10, P11, P12, P13, P14, P15, P16, P17, P19, P20, P21, P22, P23, P24, P26, P27, P29, P30, P31, P32, P33, P34, P35, P36.

Example B6: Activity Against *Myzus persicae* (Green Peach Aphid) Feeding/Contact Activity Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P1, P2, P3, P4, P5, P6, P7, P10, P11, P12, P13, P14, P15, P16, P17, P19, P20, P21, P22, P23, P24, P26, P27, P29, P33, P34, P35, P36, P37.

Example B7: Activity Against *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P1, P2, P3, P4, P5, P6, P7, P8, P9, P10, P11, P12, P13, P14, P15, P16, P17, P19, P20, P21, P22, P23, P24, P26, P27, P29, P30, P31, P32, P33, P34, P35, P36, P37.

Example B8: Activity Against *Myzus persicae* (Green Peach Aphid) Systemic Activity Roots of pea seedlings infested with an aphid population of mixed ages were placed directly into aqueous test solutions prepared from 10,000 ppm DMSO stock solutions. The samples were assessed for mortality 6 days after placing seedlings into test solutions.

The following compounds resulted in at least 80% mortality at a test rate of 24 ppm: P13, P23, P36.

Example B9: Activity Against *Tetranychus urticae* (Two-Spotted Spider Mite)

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: P10, P14, P15, P16, P17, P35.

Example B10: Activity Against *Chilo suppressalis* (Striped Rice Stemborer)

24-well microtiter plates with artificial diet were treated with aqueous test solutions prepared from 10,000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control at an application rate of 200 ppm: P10, P11, P12, P17, P19, P20, P21, P22, P23, P24, P26, P27, P29, P30, P31, P32, P33, P34, P35, P36, P37.

Example B11: Activity Against *Carpocapsa* (*Cydia*) Pomonella (Codling Moth)

Diet cubes coated with paraffin were sprayed with diluted test solutions in an application chamber. After drying off the treated cubes (10 replicates) were infested with 1 L1 larvae. Samples were incubated at 26-27° C. and checked 14 days after infestation for mortality and growth inhibition. The following compounds gave an effect of at least 80% in at least one of the two categories (mortality or growth inhibition) at an application rate of 12.5 ppm: P1, P2, P3, P4, P5, P6, P10, P11, P12, P14, P15, P16, P17, P19, P20, P21, P22, P24, P27, P29, P30, P33, P34, P35.

Example B12: Activity Against *Diabrotica Balteata* (Corn Root Worm)

Three corn seedlings were placed on wetted filter paper in plastic cups, and 3 ml of diluted test solutions were pipetted onto them. The cups were infested with 10 L2 larva and checked for mortality and growth regulation 5 days after treatment.

The following compounds gave an effect of at least 80% in at least one of the two categories (mortality or growth inhibition) at an application rate of 3 ppm: P1, P2, P3, P4, P5, P6, P7, P10, P11, P12, P14, P15, P16, P17, P18, P19, P20, P21, P22, P24, P26, P27, P28, P29, P30, P32, P33, P34, P35, P37.

The invention claimed is:

1. A compound of formula (I)

(I)

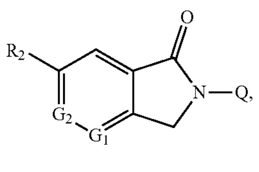

wherein $G_1$ and $G_2$ are, independently from each other, CH or N;

$R_2$ is $C_1$-$C_6$haloalkyl, $C_1$-$C_4$haloalkylsulfanyl, $C_1$-$C_4$haloalkylsulfinyl, $C_1$-$C_4$haloalkylsulfonyl, $C_1$-$C_6$haloalkoxy or $C_1$-$C_4$haloalkylsulfonyloxy;

Q is a radical of formula Qa

Qa

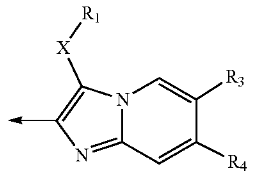

wherein the arrow denotes the point of attachment to the nitrogen atom of the bicyclic ring;

and wherein,

X is S, SO, or $SO_2$;

$R_1$ is $C_1$-$C_4$alkyl or $C_3$-$C_6$cycloalkyl-$C_1$-$C_4$alkyl;

$R_3$, and $R_4$, are, independently from each other, hydrogen, halogen, $C_1$-$C_4$alkyl, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$cyanoalkoxy, $C_3$-$C_6$cyanocycloalkyl$C_1$-$C_4$alkoxy, cyano, $C_1$-$C_4$alkoxy, $C_1$-$C_6$haloalkoxy, —$N(R_7)_2$, or —$N(R_7)C(=O)R_8$; and $R_7$ and $R_8$ are, independently from each other, hydrogen, $C_1$-$C_4$alkyl, $C_1$-$C_6$haloalkyl, or $C_3$-$C_6$cycloalkyl;

or an agrochemically acceptable salt, stereoisomer, enantiomer, tautomer or N-oxide of a compound of formula I.

2. A compound of formula I according to claim 1, represented by the compounds of formula (I-1)

(I-1)

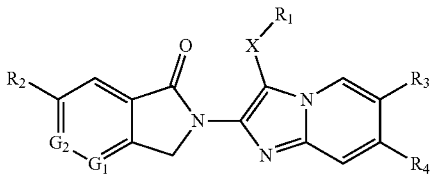

wherein $R_2$, $G_1$, $G_2$, X, $R_1$, $R_3$, $R_4$, $R_7$ and $R_8$ are as defined under formula I in claim 1, or an agrochemically acceptable salt, stereoisomer, enantiomer, tautomer or N-oxide thereof.

3. A compound according to claim 1, wherein either $G_1$ is N and $G_2$ is CH, or $G_1$ is CH and $G_2$ is N.

4. A compound according to claim 1, wherein either both $G_1$ and $G_2$ are N, or both $G_1$ and $G_2$ are CH.

5. A compound of formula I according to claim 1, represented by the compounds of formula (I-3)

(I-3)

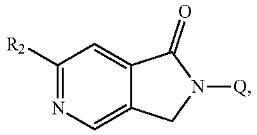

wherein Q is a radical of formula Qa

Qa

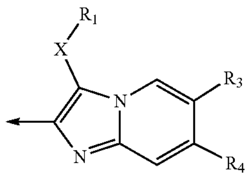

wherein the arrow denotes the point of attachment to the nitrogen atom of the bicyclic ring; and $R_2$, X, $R_1$, $R_3$, $R_4$, $R_7$ and $R_8$ are as defined under formula I in claim 1, or an agrochemically acceptable salt, stereoisomer, enantiomer, tautomer or N-oxide thereof.

6. A compound of formula I according to claim 1, represented by the compounds of formula (I-4)

(I-4)

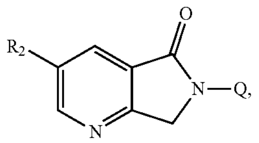

wherein Q is a radical of formula Qa

Qa

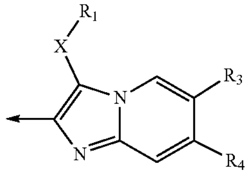

wherein the arrow denotes the point of attachment to the nitrogen atom of the bicyclic ring; and $R_2$, X, $R_1$, $R_3$, $R_4$, $R_7$ and $R_8$ are as defined under formula I in claim 1, or an agrochemically acceptable salt, stereoisomer, enantiomer, tautomer or N-oxide thereof.

7. A compound of formula I according to claim 1, represented by the compounds of formula (I-5)

(I-5)

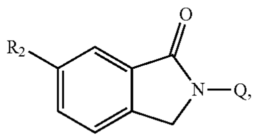

wherein Q is a radical of formula Qa

Qa

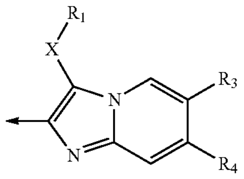

wherein the arrow denotes the point of attachment to the nitrogen atom of the bicyclic ring; and $R_2$, X, $R_1$, $R_3$, $R_4$, $R_7$ and $R_8$ are as defined under formula I in claim 1, or an agrochemically acceptable salt, stereoisomer, enantiomer, tautomer or N-oxide thereof.

8. A compound of formula I according to claim 1, represented by the compounds of formula (I-6)

(I-6)

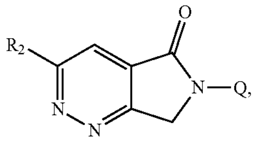

wherein Q is a radical of formula Qa

Qa

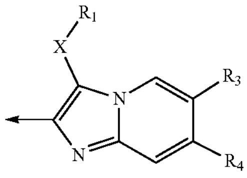

wherein the arrow denotes the point of attachment to the nitrogen atom of the bicyclic ring; and $R_2$, X, $R_1$, $R_3$, $R_4$, $R_7$ and $R_8$ are as defined under formula I in claim 1, or an agrochemically acceptable salt, stereoisomer, enantiomer, tautomer or N-oxide thereof.

9. A compound according to claim 1, wherein:

X is S or $SO_2$; and $R_1$ is $C_1$-$C_4$alkyl or cyclopropyl-$C_1$-$C_4$alkyl.

10. A compound according to claim 1, wherein:

$R_2$ is $C_1$-$C_2$haloalkyl, $C_1$-$C_2$haloalkylsulfanyl, $C_1$-$C_2$haloalkylsulfinyl, $C_1$-$C_2$haloalkylsulfonyl, $C_1$-$C_2$haloalkoxy or $C_1$-$C_2$haloalkylsulfonyloxy.

11. A compound according to claim 10, wherein $R_2$ is —$CF_3$, —$OCHF_2$, —$OCF_3$ or —$SO_2CF_3$.

12. A compound according to claim 1, wherein:

Q is Qa; and $R_4$ is hydrogen and $R_3$ is hydrogen, bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$; or $R_3$ is hydrogen and $R_4$ is bromo, methyl, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or —NHC(O)$CH_3$.

13. A compound of formula I according to claim 1, selected from the group consisting of:

6-[3-ethylsulfonyl-7-(trifluoromethyl)imidazo[1,2-a]pyridin-2-yl]-3-(trifluoromethyl)-7H-pyrrolo[3,4-b]pyridin-5-one (compound P2);

1-[3-ethylsulfonyl-2-[5-oxo-3-(trifluoromethyl)-7H-pyrrolo[3,4-b]pyridin-6-yl]imidazo[1,2-a]pyridin-7-yl]cyclopropanecarbonitrile (compound P3);

6-[3-ethylsulfonyl-6-(trifluoromethyl)imidazo[1,2-a]pyridin-2-yl]-3-(trifluoromethyl)-7H-pyrrolo[3,4-b]pyridin-5-one (compound P4);

1-[3-ethylsulfonyl-2-[1-oxo-6-(trifluoromethoxy)isoindolin-2-yl]imidazo[1,2-a]pyridin-7-yl]cyclopropanecarbonitrile (compound P5);

2-[3-ethylsulfonyl-6-(trifluoromethyl)imidazo[1,2-a]pyridin-2-yl]-6-(trifluoromethoxy)isoindolin-1-one (compound P6);

2-[3-ethylsulfonyl-7-(trifluoromethyl)imidazo[1,2-a]pyridin-2-yl]-6-(trifluoromethoxy)isoindolin-1-one (compound P7);

6-(3-ethylsulfonyl-6-methoxy-imidazo[1,2-a]pyridin-2-yl)-3-(trifluoromethyl)-7H-pyrrolo[3,4-b]pyridin-5-one (compound P8);

6-(3-ethylsulfonyl-6-isopropoxy-imidazo[1,2-a]pyridin-2-yl)-3-(trifluoromethyl)-7H-pyrrolo[3,4-b]pyridin-5-one (compound P9);

6-[6-(difluoromethoxy)-3-ethylsulfonyl-imidazo[1,2-a]pyridin-2-yl]-3-(trifluoromethyl)-7H-pyrrolo[3,4-b]pyridin-5-one (compound P10);

6-[3-ethylsulfonyl-6-(2,2,2-trifluoroethoxy)imidazo[1,2-a]pyridin-2-yl]-3-(trifluoromethyl)-7H-pyrrolo[3,4-b]pyridin-5-one (compound P11);

6-[3-ethylsulfonyl-7-(2,2,2-trifluoroethoxy)imidazo[1,2-a]pyridin-2-yl]-3-(trifluoromethyl)-7H-pyrrolo[3,4-b]pyridin-5-one (compound P12);

6-(3-ethylsulfonyl-7-methoxy-imidazo[1,2-a]pyridin-2-yl)-3-(trifluoromethyl)-7H-pyrrolo[3,4-b]pyridin-5-one (compound P13);

1-[3-ethylsulfonyl-2-[1-oxo-6-(trifluoromethoxy)isoindolin-2-yl]imidazo[1,2-a]pyridin-6-yl]cyclopropanecarbonitrile (compound P14);

1-[3-ethylsulfonyl-2-[5-oxo-3-(trifluoromethyl)-7H-pyrrolo[3,4-b]pyridin-6-yl]imidazo[1,2-a]pyridin-6-yl]cyclopropanecarbonitrile (compound P15);

1-[3-ethylsulfonyl-2-[1-oxo-6-(trifluoromethyl)isoindolin-2-yl]imidazo[1,2-a]pyridin-6-yl]cyclopropanecarbonitrile (compound P16);

2-[6-(1,1-difluoroethyl)-3-ethylsulfonyl-imidazo[1,2-a]pyridin-2-yl]-6-(trifluoromethoxy)isoindolin-1-one (compound P17);

6-[6-(1,1-difluoroethyl)-3-ethylsulfonyl-imidazo[1,2-a]pyridin-2-yl]-3-(trifluoromethyl)-7H-pyrrolo[3,4-b]pyridin-5-one (compound P18);

6-[6-(2,2-difluoroethoxy)-3-ethylsulfonyl-imidazo[1,2-a]pyridin-2-yl]-3-(trifluoromethyl)-7H-pyrrolo[3,4-b]pyridin-5-one (compound P19);

2-[3-ethylsulfonyl-2-[5-oxo-3-(trifluoromethyl)-7H-pyrrolo[3,4-b]pyridin-6-yl]imidazo[1,2-a]pyridin-6-yl]oxy-2-methyl-propanenitrile (compound P20);

6-(6-bromo-3-ethylsulfonyl-imidazo[1,2-a]pyridin-2-yl)-3-(trifluoromethyl)-7H-pyrrolo[3,4-b]pyridin-5-one (compound P21);

6-(7-bromo-3-ethylsulfonyl-imidazo[1,2-a]pyridin-2-yl)-3-(trifluoromethyl)-7H-pyrrolo[3,4-b]pyridin-5-one (compound P22);

6-(3-ethylsulfonyl-7-methyl-imidazo[1,2-a]pyridin-2-yl)-3-(trifluoromethyl)-7H-pyrrolo[3,4-b]pyridin-5-one (compound P23);

6-(7-cyclopropyl-3-ethylsulfonyl-imidazo[1,2-a]pyridin-2-yl)-3-(trifluoromethyl)-7H-pyrrolo[3,4-b]pyridin-5-one (compound P24);

6-[7-(1,1-difluoroethyl)-3-ethylsulfonyl-imidazo[1,2-a]pyridin-2-yl]-3-(trifluoromethyl)-7H-pyrrolo[3,4-b]pyridin-5-one (compound P25);

2-[3-ethylsulfonyl-2-[1-oxo-6-(trifluoromethoxy)isoindolin-2-yl]imidazo[1,2-a]pyridin-6-yl]oxy-2-methyl-propanenitrile (compound P26);

6-(6-cyclopropyl-3-ethylsulfonyl-imidazo[1,2-a]pyridin-2-yl)-3-(trifluoromethyl)-7H-pyrrolo[3,4-b]pyridin-5-one (compound P27);

2-[3-ethylsulfonyl-7-(2,2,2-trifluoroethoxy)imidazo[1,2-a]pyridin-2-yl]-6-(trifluoromethoxy)isoindolin-1-one (compound P28);

2-(6-bromo-3-ethylsulfonyl-imidazo[1,2-a]pyridin-2-yl)-6-(trifluoromethoxy)isoindolin-1-one (compound P29);

2-(6-bromo-3-ethylsulfonyl-imidazo[1,2-a]pyridin-2-yl)-6-(trifluoromethylsulfonyl)isoindolin-1-one (compound P30);

1-[[3-ethylsulfonyl-2-[5-oxo-3-(trifluoromethyl)-7H-pyrrolo[3,4-b]pyridin-6-yl]imidazo[1,2-a]pyridin-6-yl]oxymethyl]cyclopropanecarbonitrile (compound P31);

2-[3-ethylsulfonyl-6-(trifluoromethyl)imidazo[1,2-a]pyridin-2-yl]-6-(trifluoromethylsulfonyl)isoindolin-1-one (compound P32);

2-[3-ethylsulfonyl-7-(2,2,2-trifluoroethoxy)imidazo[1,2-a]pyridin-2-yl]-6-(trifluoromethylsulfonyl)isoindolin-1-one (compound P33);

6-(difluoromethoxy)-2-[3-ethylsulfonyl-6-(trifluoromethyl)imidazo[1,2-a]pyridin-2-yl]isoindolin-1-one (compound P34);

2-[3-ethylsulfonyl-2-[5-oxo-3-(trifluoromethyl)-7H-pyrrolo[3,4-b]pyridin-6-yl]imidazo[1,2-a]pyridin-6-yl]-2-methyl-propanenitrile (compound P35);

N-[3-ethylsulfonyl-2-[5-oxo-3-(trifluoromethyl)-7H-pyrrolo[3,4-b]pyridin-6-yl]imidazo[1,2-a]pyridin-6-yl]acetamide (compound P36);

2-[3-ethylsulfonyl-7-(trifluoromethyl)imidazo[1,2-a]pyridin-2-yl]-6-(trifluoromethylsulfonyl)isoindolin-1-one (compound P37); and 6-[7-(2,2-difluoroethoxy)-3-ethylsulfonyl-imidazo[1,2-a]pyridin-2-yl]-3-(trifluoromethyl)-7H-pyrrolo[3,4-b]pyridin-5-one (compound P38).

14. A composition comprising an insecticidally, acaricidally, nematicidally or molluscicidally effective amount of a compound of formula (I), or an agrochemically acceptable salt, stereoisomer, enantiomer, tautomer or N-oxide thereof, as defined in claim 1 and, optionally, an auxiliary or diluent.

15. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in claim 1.

16. A method for the protection of plant propagation material from the attack by insects, acarines, nematodes or molluscs, which comprises treating the propagation material or the site, where the propagation material is planted, with a composition according to claim 14.

17. A method of combating and controlling insects, acarines, nematodes or molluscs which comprises applying to a pest, to a locus of a pest, or to a plant susceptible to attack by a pest in insecticidally, acaricidally, nematicidally or molluscicidally effective amount of a compound of formula (I), or an agrochemically acceptable salt, stereoisomer, enantiomer, tautomer or N-oxide thereof, as defined in claim 1, or a composition thereof.

18. The compound according to claim 3, wherein $G_1$ is N and $G_2$ is CH.

19. The compound according to claim 9, wherein:

X is S02; and $R_1$ is ethyl or cyclopropylmethyl.

20. The compound according to claim 10, wherein $R_2$ is $-CF_3$, $-CF_2CF_3$, $-SCF_3$, $-SOCF_3$, $-SO_2CF_3$, $-OCHF_2$, $-OCF_3$ or $-OSO_2CF_3$.

21. The compound according to claim 12, wherein:

$R_4$ is hydrogen and $R_3$ is bromo, trifluoromethyl, 1,1-difluoroethyl, cyclopropyl, 1-cyanocyclopropyl, 1-cyano-1-methyl-ethyl, 1-cyano-1-methyl-ethoxy, methoxy, isopropoxy, difluoromethoxy, 2,2,2-trifluoroethoxy, 2,2-difluoroethoxy, or $-NHC(O)CH_3$; or $R_3$ is hydrogen and $R_4$ bromo, methyl, trifluoromethyl, 1,1-difluoroethyl, cyclopropyl, 1-cyanocyclopropyl, methoxy, or 2,2,2-trifluoroethoxy.

* * * * *